(12) United States Patent
Oja et al.

(10) Patent No.: US 10,287,565 B2
(45) Date of Patent: May 14, 2019

(54) ISOPRENE SYNTHASE AND METHOD OF PREPARING ISOPRENE USING THEREOF

(71) Applicant: SK Innovation Co., Ltd., Seoul (KR)

(72) Inventors: Merja Oja, Espoo (FI); Anne Huuskonen, Helsinki (FI); Marja Iimen, Helsinki (FI); Laura Ruohonen, Helsinki (FI); Outi Koivistoinen, Espoo (FI); Simon Moon Geun Jung, Daejeon (KR); Jae Hoon Jo, Seoul (KR); Sang Min Lee, Seoul (KR)

(73) Assignee: SK Innovation Co., Ltd., Seoul (KR)

(*) Notice: Subject to any disclaimer, the term of this patent is extended or adjusted under 35 U.S.C. 154(b) by 0 days.

(21) Appl. No.: 15/329,343

(22) PCT Filed: Jul. 28, 2015

(86) PCT No.: PCT/KR2015/007851
§ 371 (c)(1),
(2) Date: Jan. 26, 2017

(87) PCT Pub. No.: WO2016/018036
PCT Pub. Date: Feb. 4, 2016

(65) Prior Publication Data
US 2017/0211056 A1    Jul. 27, 2017

(30) Foreign Application Priority Data
Jul. 28, 2014 (KR) .................. 10-2014-0095972

(51) Int. Cl.
C12N 9/88 (2006.01)
C12P 5/00 (2006.01)
C12P 5/02 (2006.01)
C12N 15/74 (2006.01)

(52) U.S. Cl.
CPC .............. *C12N 9/88* (2013.01); *C12N 15/74* (2013.01); *C12P 5/007* (2013.01); *C12P 5/026* (2013.01); *C12Y 402/03027* (2013.01)

(58) Field of Classification Search
None
See application file for complete search history.

(56) References Cited

U.S. PATENT DOCUMENTS

| | | | |
|---|---|---|---|
| 4,186,183 A | 1/1980 | Steck et al. | |
| 4,217,344 A | 8/1980 | Vanlerberghe et al. | |
| 4,235,871 A | 11/1980 | Papahadjopoulos et al. | |
| 4,261,975 A | 4/1981 | Fullerton et al. | |
| 4,485,054 A | 11/1984 | Mezei et al. | |
| 4,501,728 A | 2/1985 | Geho et al. | |
| 4,774,085 A | 9/1988 | Fidler | |
| 4,797,368 A | 1/1989 | Carter et al. | |
| 4,837,028 A | 6/1989 | Allen | |
| 4,897,355 A | 1/1990 | Eppstein et al. | |
| 4,946,787 A | 8/1990 | Eppstein et al. | |
| 5,049,386 A | 9/1991 | Eppstein et al. | |
| 5,173,414 A | 12/1992 | Lebkowski et al. | |
| 5,264,618 A | 11/1993 | Felgner et al. | |
| 5,849,970 A | 12/1998 | Fall et al. | |
| 5,990,279 A | 11/1999 | Carter et al. | |
| 9,994,869 B2 * | 6/2018 | Song | C12P 5/007 |
| 2009/0226989 A1 | 9/2009 | Suominen et al. | |
| 2011/0045563 A1 | 2/2011 | Melis | |
| 2013/0330709 A1 | 12/2013 | Beatty et al. | |
| 2015/0232884 A1 | 8/2015 | Duehring | |

FOREIGN PATENT DOCUMENTS

| | | |
|---|---|---|
| WO | 9116024 A1 | 10/1991 |
| WO | 9117424 A1 | 11/1991 |
| WO | 9324641 A2 | 12/1993 |
| WO | 2013166320 A1 | 11/2013 |
| WO | 2014037050 A1 | 3/2014 |

OTHER PUBLICATIONS

Whisstock et al. Quaterly Reviews of Biophysics, 2003, "Prediction of protein function from protein sequence and structure", 36(3): 307-340.*
Chica et al., Semi-rational approaches to engineering enzyme activity: combining the benefits of directed evolution and rational design. Curr. Opi. Biotechnol., 2005, vol. 16: 378-384.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Ahmad et al.; "Antibody-mediated Specific Binding and Cytotoxicity of Liposome-entrapped Doxorubicin to Lung Cancer Cells in Vitro"; Cancer Research; 1992; pp. 4817-4820; vol. 52.
Behr; "Gene Transfer with Synthetic Cationic Amphiphiles: Prospects for Gene Therapy"; Bioconjugate Chem; 1994; pp. 382-389; vol. 5.
Bentley et al.; "Diffusion-Based Process for Carbon Dioxide Uptake and Isoprene Emission in Gaseous/Aqueous Two-Phase Photobioreactors by Photosynthetic Microorganisms"; Biotechnology and Bioengineering; 2012; pp. 100-109; vol. 109:1.
Blaese et al.; "T Lymphocyte-Directed Gene Therapy for ADA SCID: Initial Trial Results After 4 Years"; Science; 1995; pp. 475-480; vol. 270.
Buchschacher, Jr. et al.; "Human Immunodeficieny Virus Vectors for Inducible Expression of Foreign Genes"; Journal of Virology; 1992; pp. 2731-2739; vol. 66:5.
Crystal; "Transfer of Genes to Humans: Early Lessons and Obstacles to Success"; Science; 1995; pp. 404-410; vol. 270.
Devereux et al.; "A comprehensive set of sequence analysis programs for the VAX"; Nucleic Acids Research; 1984; pp. 387-395; vol. 12:1.

(Continued)

*Primary Examiner* — Iqbal H Chowdhury
(74) *Attorney, Agent, or Firm* — The Webb Law Firm

(57) ABSTRACT

Provided are a novel isoprene synthase derived from sweet potato and a method of preparing isoprene using the same, and more specifically, a novel isoprene synthase derived from sweet potato, a gene encoding the isoprene synthase, a host cell transformed with the gene, and a method of preparing isoprene using the same. The isoprene synthase of the present invention may have higher isoprene productivity as compared to isoprene synthases known in the related art to thereby be effectively used in isoprene biosynthesis and preparation of an isoprene polymer using the same.

18 Claims, 14 Drawing Sheets

Specification includes a Sequence Listing.

(56) References Cited

OTHER PUBLICATIONS

Dranoff et al.; "A Phase I Study of Vaccination with Autologous, Irradiated Melanoma Cells Engineered to Secrete Human Granulocyte-Macrophage Colony Stimulating Factor"; Human Gene Therapy; 1997; pp. 111-123; vol. 7.
Dunbar et al.; "Retrovirally Marked CD34-Enriched Peripheral Blood and Bone Marrow Cells Contribute to Long-Term Engraftment After Autologous Transplantation"; Blood; 1995; pp. 3048-3057; vol. 85:11.
Ellem et al.; "A case report: Immune responses and clinical course of the first human use of granulocyte/macrophage-colony-stimulating-factor-transduced autologous melanoma cells for immunotherapy"; Cancer Immunol Immunother; 1997; pp. 10-20; vol. 44.
Gietz et al.; "[4] Transformation of Yeast by Lithium Acetate/Single-Stranded Carrier DNA/Polyethylene Glycol Method"; Methods in Enzymology; 2002; pp. 87-96; vol. 350.
Gietz et al.; "Improved method for high efficiency transformation of intact yeast cells"; Nucleic Acids Research; 1992; pp. 1425; vol. 20:6.
Gray et al.; "Biochemical Characterization and Homology Modeling of Methylbutenol Synthase and Implications for Understanding Hemiterpene Synthase Evolution in Plants"; The Journal of Biological Chemistry; 2011; pp. 20582-20590; vol. 286:23.
Hakkinen et al.; "Functional characterisation of genes involved in pyridine alkaloid biosynthesis in tobacco"; Phytochemistry; 2007; pp. 2773-2785; vol. 68.
Hermonat et al.; "Use of adeno-associated virus as a mammalian DNA cloning vector: Transduction of neomycin resistance into mammalian tissue culture cells"; Proc. Natl. Acad. Sci. USA; 1984; pp. 6466-6470; vol. 81.
Johann et al.; "GLVR1, a Receptor for Gibbon Ape Leukemia Virus, Is Homologous to a Phosphate Permease of Neurospora crassa and Is Expressed at High Levels in the Brain and Thymus"; Journal of Virology; 1992; pp. 1635-1640; vol. 66:3.
Jouhikainen et al.; "Enhancement of scopolamine production in *Hyoscyamus muticus* L. hairy root cultures by genetic engineering"; Planta; 1999; pp. 545-551; vol. 208.
Julsing et al.; "Functional analysis of genes involved in the biosynthesis of isoprene in Bacillus subtilis"; Appl Microbiol Biotechnol; 2007; pp. 1377-1384; vol. 75.
Kohn et al.; "Engraftment of gene-modified umbilical cord blood cells in neonates with adenosine deaminase deficiency"; Nat Med.; 1995; pp. 1017-1023; vol. 1:10.
Kotin; "Review: Prospects for the Use of Adeno-Associated Virus as a Vector for Human Gene Therapy"; Human Gene Therapy; 1994; pp. 793-801; vol. 5.
Kuzma et al.; "Bacteria Produce the Volatile Hydrocarbon Isoprene"; Current Microbiology; 1995; pp. 97-103; vol. 30.
Malech et al.; "Prolonged production of NADPH oxidase-corrected granulocytes after gene therapy of chronic granulomatous disease"; Proc. Natl. Acad. Sci. USA; 1997; pp. 12133-12138; vol. 94.
Miller et al.; "Construction and Properties of Retrovirus Packaging Cells Based on Gibbon Ape Leukemia Virus"; Journal of Virology; 1991; pp. 2220-2224; vol. 65:5.
Muzyczka; "Adeno-associated Virus (AAV) Vectors: Will They Work?"; J. Clin. Invest.; 1994; pp. 1351; vol. 94.
NCBI; "unnamed protein product [*Coffea canephora*]"; GenBank accession No. CDP11842.1; Jun. 27, 2014.

Needleman et al.; "A General Method Applicable to the Search for Similarities in the Amino Acid Sequence of Two Proteins"; J. Mol. Biol.; 1970; pp. 443-453; vol. 48.
Pearson et al.; "Improved tools for biological sequence comparison"; Proc. Natl. Acad. Sci. USA; 1988; pp. 2444-2448; vol. 85.
Peranen et al.; "T7 Vectors with a Modified T7 lac Promoter for Expression of Proteins in *Escherichia coli*"; Analytical Biochemistry; 1996; pp. 371-373; vol. 236.
Polakowski et al.; "Overexpression of a cytosolic hydroxymethylglutaryl-CoA reductase leads to squalene accumulation in yeast"; Appl Microbiol Biotechnol; 1998; pp. 66-71; vol. 49.
Remy et al.; "Gene Transfer with a Series of Lipophilic DNA-Binding Molecules"; Bioconjugate Chem.; 1994; pp. 647-654; vol. 5.
Samulski et al.; "Helper-Free Stocks of Recombinant Adeno-Associated Viruses: Normal Integration Does Not Require Viral Gene Expression"; Journal of Virology; 1989; pp. 3822-3828; vol. 63:9.
Sharkey et al.; "Isoprene Synthase Genes Form a Monophyletic Glade of Acyclic Terpene Synthases in the TPS-B Terpene Synthase Family"; Evolution; 2012; pp. 1026-1040; vol. 67:4.
Silver et al.; "Characterization of Aspen Isoprene Synthase, an Enzyme Responsible for Leaf Isoprene Emission to the Atmosphere"; The Journal of Biological Chemistry; 1995; pp. 13010-13016; vol. 270:22.
Silver et al.; "Enzymatic Synthesis of Isoprene from Dimethylallyl Diphosphate in Aspen Leaf Extracts"; Plant Physiol.; 1991; pp. 1588-1591; vol. 97.
Smith; "Comparison of Biosequences"; Advances in Applied Mathematics; 1981; pp. 482-489; vol. 2.
Sommerfelt et al.; "Receptor Interference Groups of 20 Retroviruses Plating on Human Cells"; Virology; 1990; pp. 58-69; vol. 176.
Tratschin et al.; "Adeno-Associated Virus Vector for High-Frequency Integration, Expression, and Rescue of Genes in Mammalian Cells"; Molecular and Cellular Biology; 1985; pp. 3251-3260; vol. 5:11.
Tratschin et al.; "A Human Parvovirus, Adeno-Associated Virus, as a Eucaryotic Vector: Transient Expression and Encapsidation of the Procaryotic Gene for Chloramphenicol Acetyltransferase"; Molecular and Cellular Biology; 1984; pp. 2072-2081; vol. 4:10.
Wagner et al.; "Efficient and persistent gene transfer of AAV-CFTR in maxillary sinus"; The Lancet; 1998; pp. 1702-1703; vol. 351.
Wagner et al.; "Three Distinct Phases of Isoprene Formation during Growth and Sporulation of Bacillus subtilis"; Journal of Bacteriology; 1999; pp. 4700-4703; vol. 181:15.
Weissermel et al.; "5.2: Isoprene"; Industrial Organic Chemistry: Fourth, Completely Revised Edition; 2003; pp. 117-122.
West et al.; "Gene Expression in Adeno-Associated Virus Vectors: The Effects of Chimeric mRNA Structure, Helper Virus, and Adenovirus VA RNA"; Virology; 1987; pp. 38-47; vol. 160.
Wilkins; "Volatile Metabolites From Actinomycetes"; Chemosphere; 1996; pp. 1427-1434; vol. 32:7.
Wilson et al.; "Formation of Infectious Hybrid Virions with Gibbon Ape Leukemia Virus and Human T-Cell Leukemia Virus Retroviral Envelope Glycoproteins and the gag and pol Proteins of Moloney Murine Leukemia Virus"; Journal of Virology; 1989; pp. 2374-2378; vol. 63:5.
Winston et al.; "Construction of a Set of Convenient *Saccharomyces cerevisiae* Strains that are Isogenic to S288C"; Yeast; 1995; pp. 53-55; vol. 11.
Penttilä et al., "A versatile transformation system for the cellulolytic filamentous fungus *Trichoderma reesei*", Gene, 1987, pp. 155-164, vol. 61, Elsevier.

* cited by examiner

[Fig. 1a]
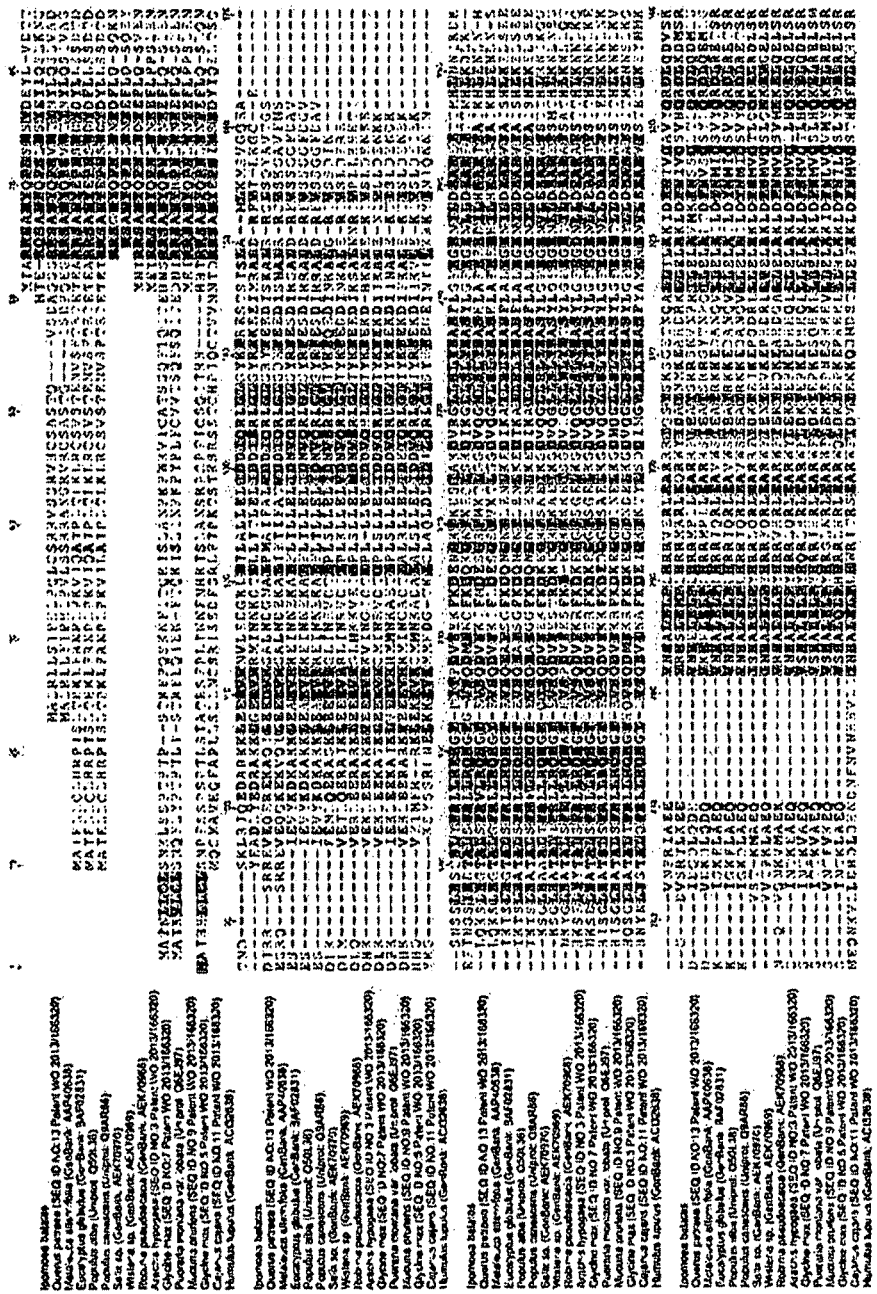

[Fig. 1b]
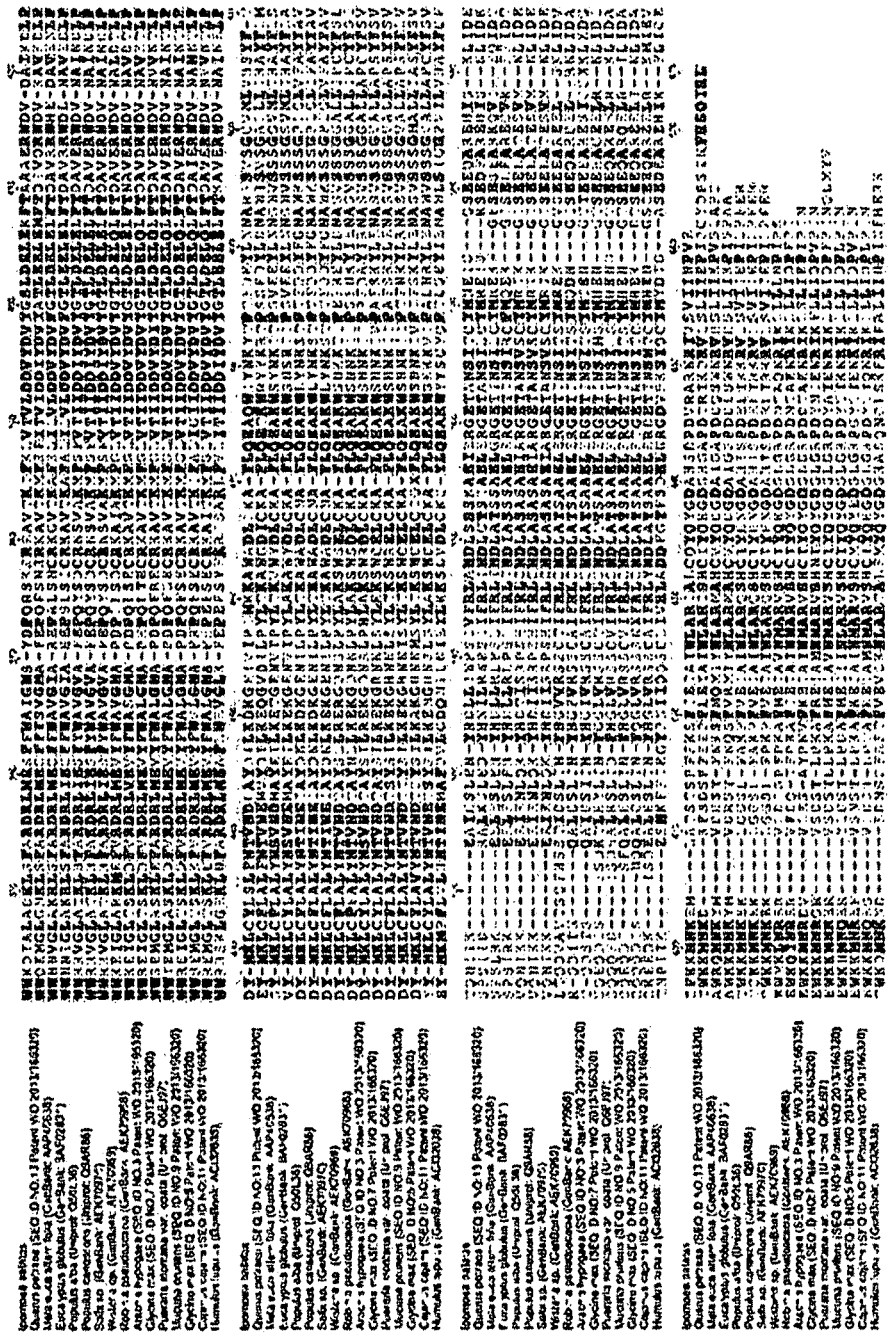

[Fig. 4]
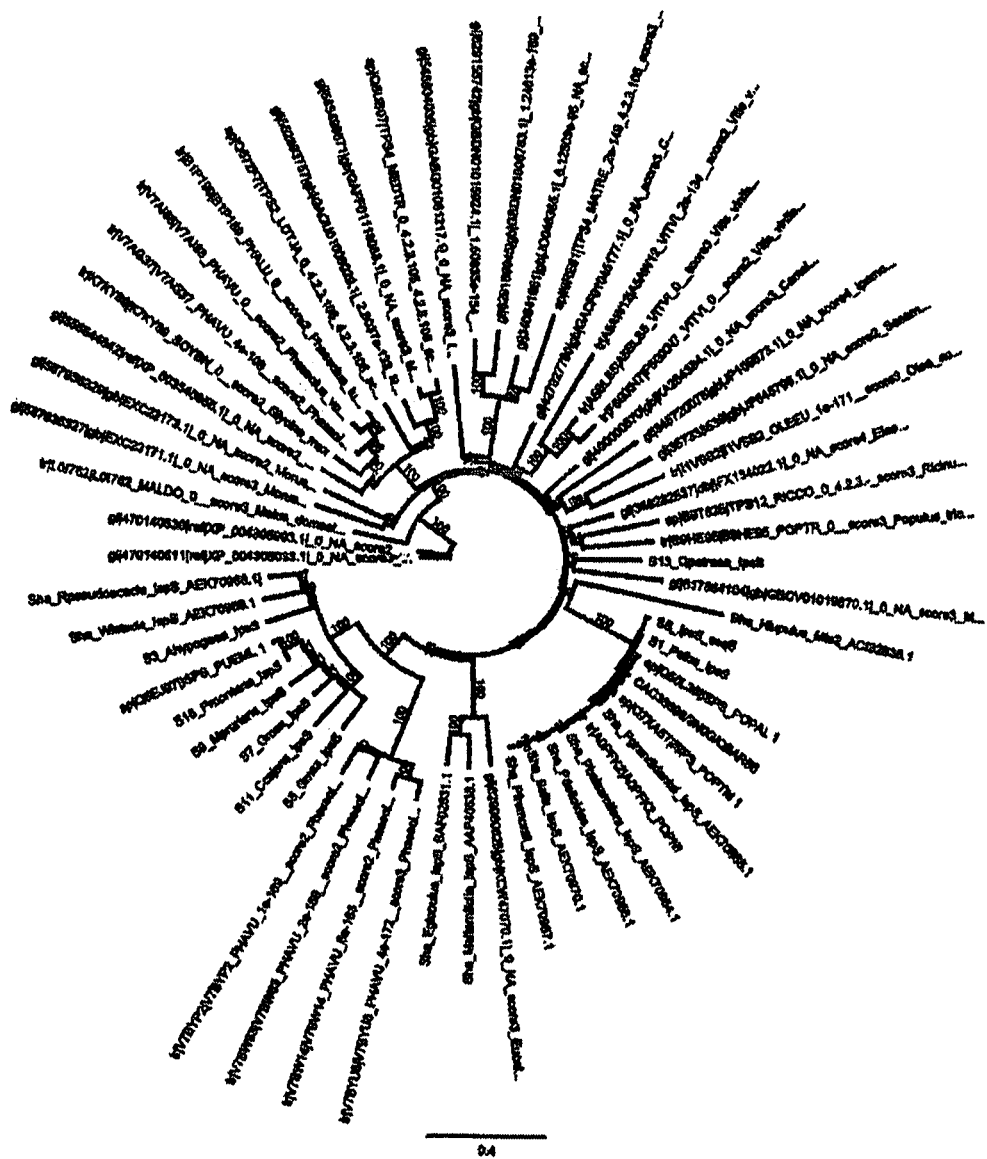

[Fig. 5]
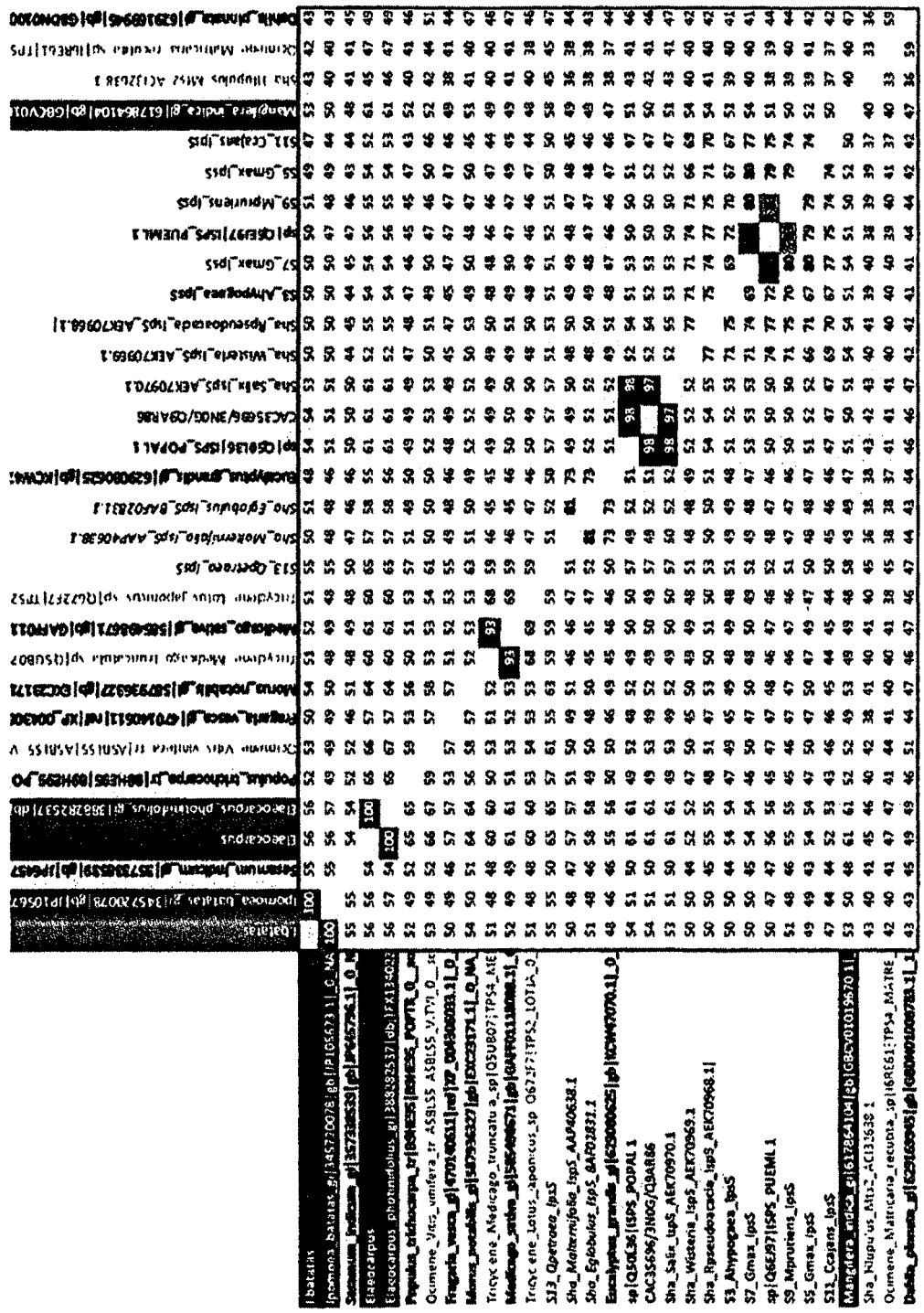

[Fig. 6]
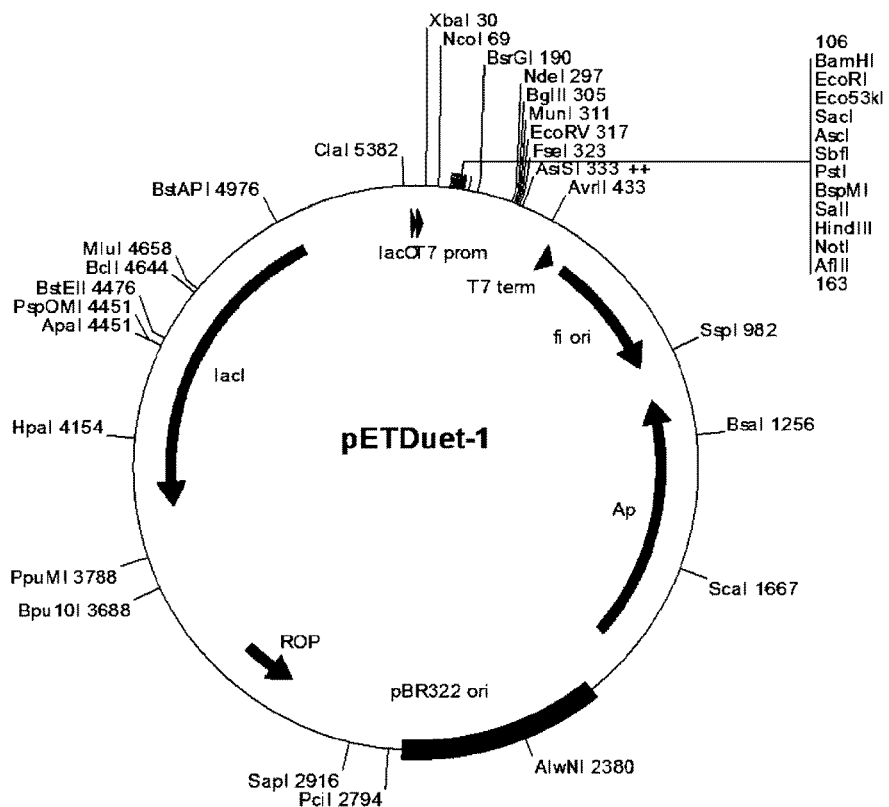
[Fig. 7]
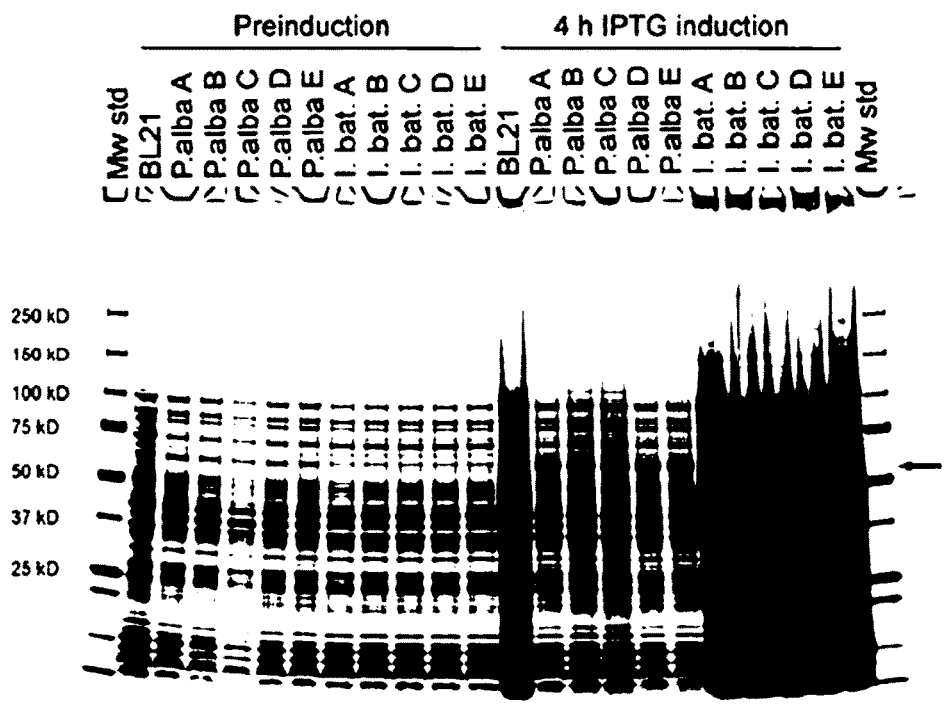

[Fig. 8]
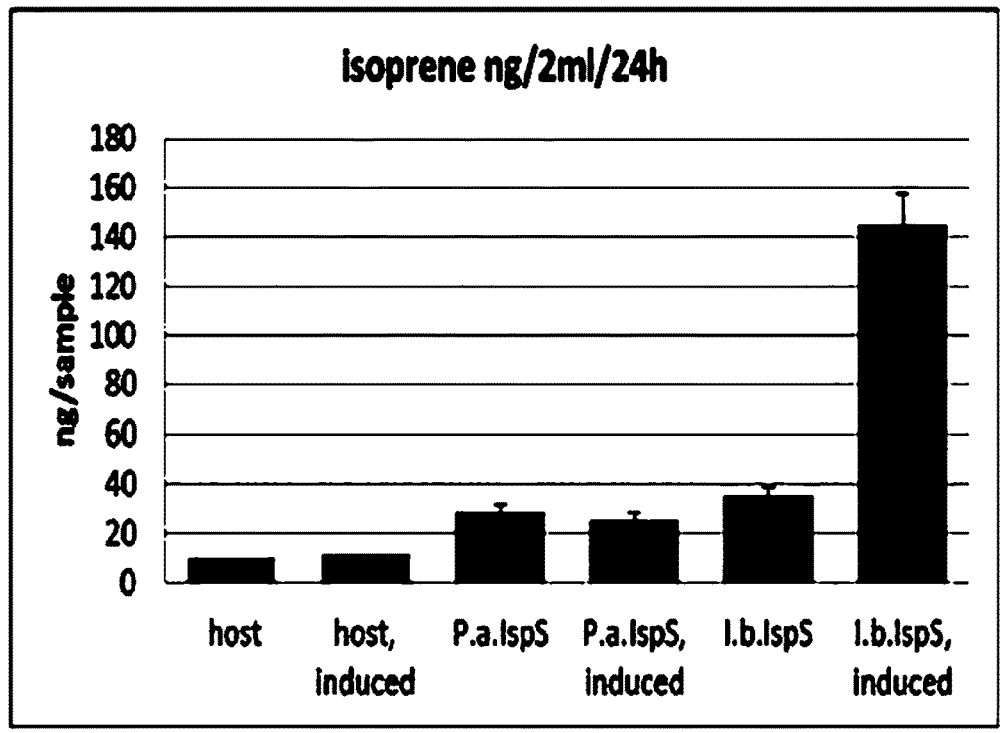
[Fig. 9]
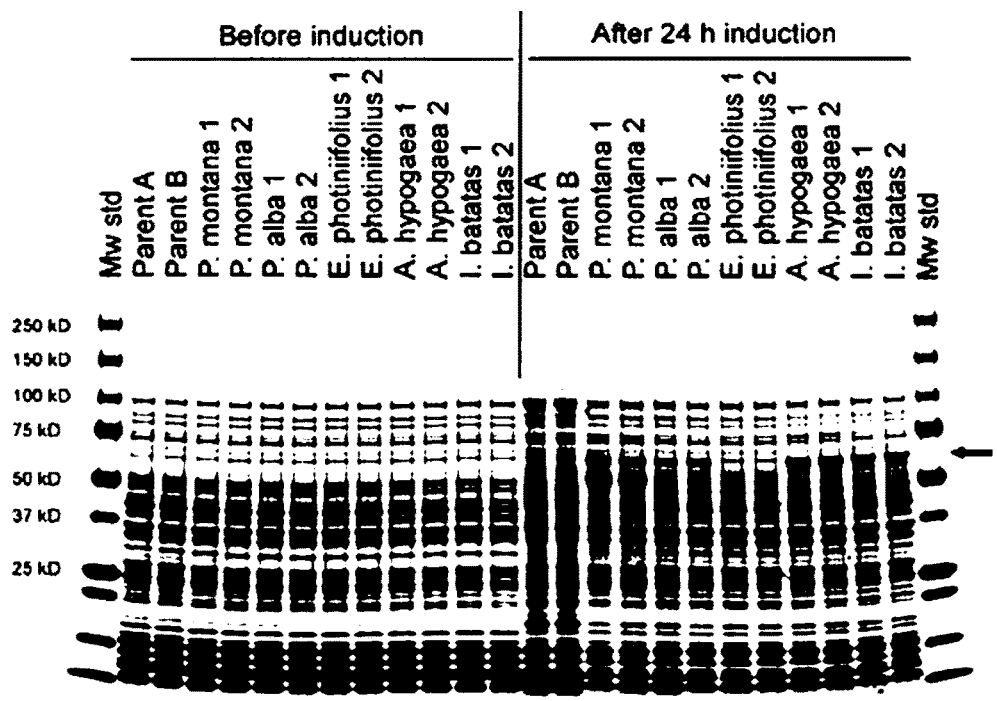

[Fig. 10]
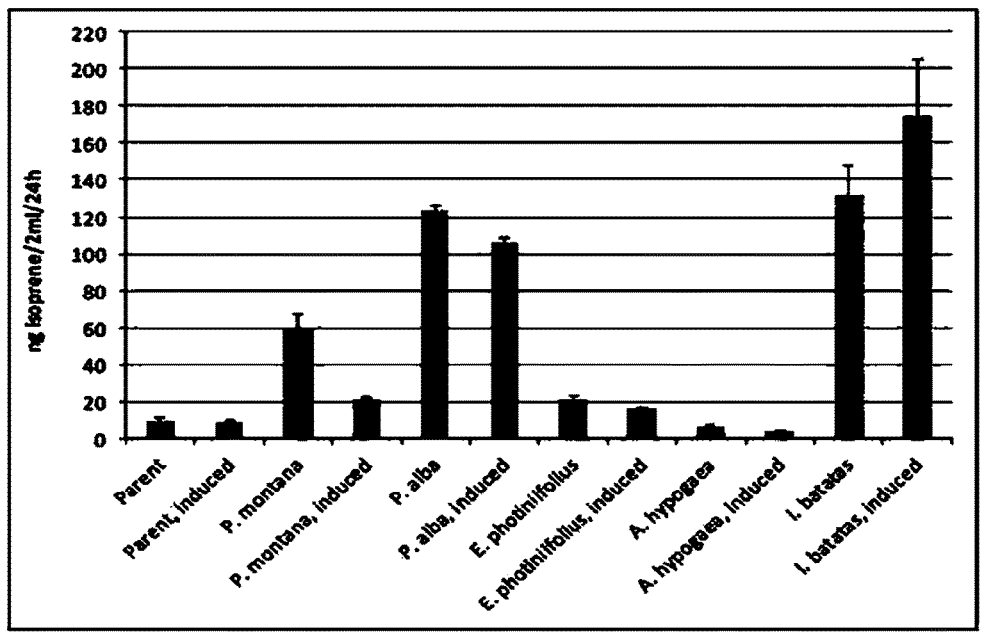
[Fig. 11]
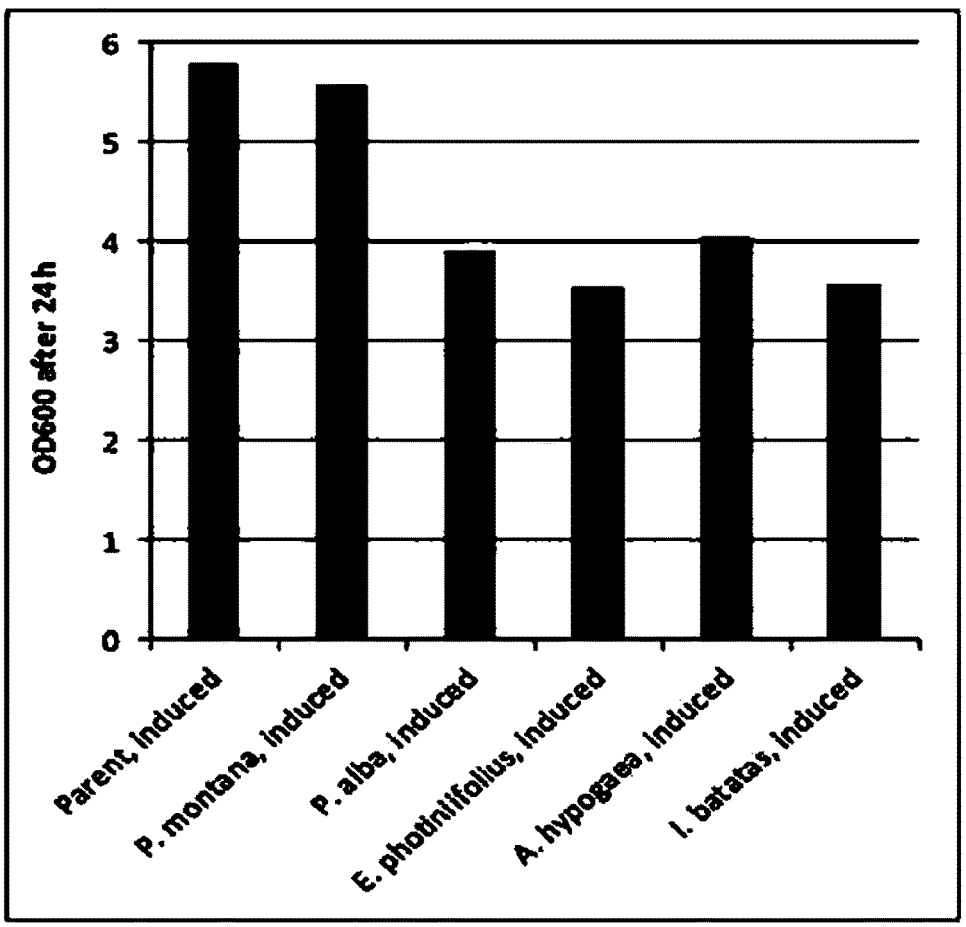

[Fig. 12]
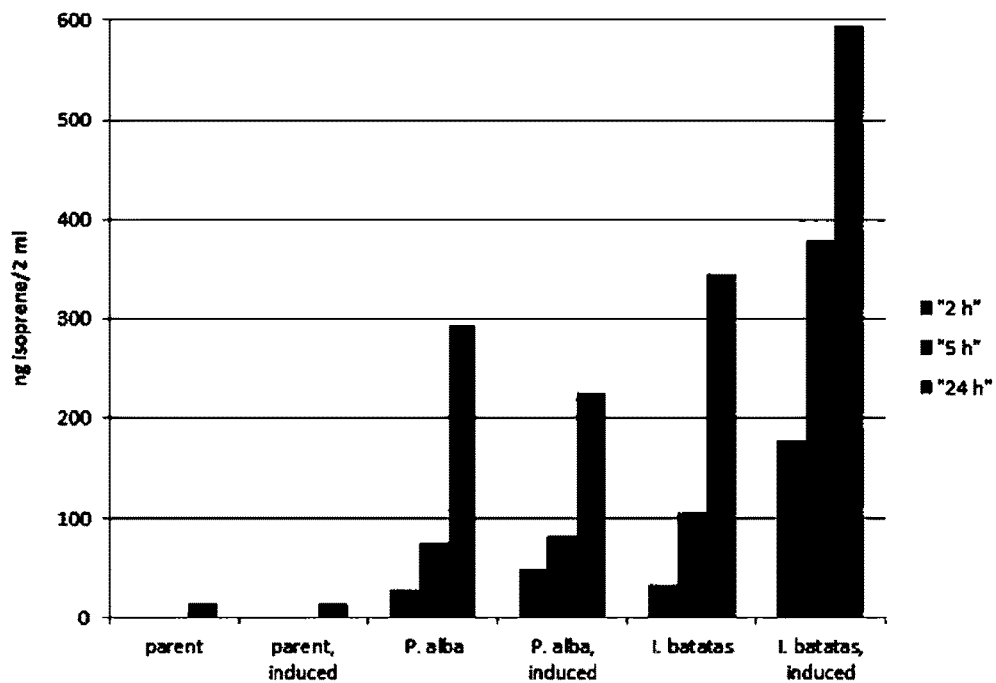
[Fig. 13]
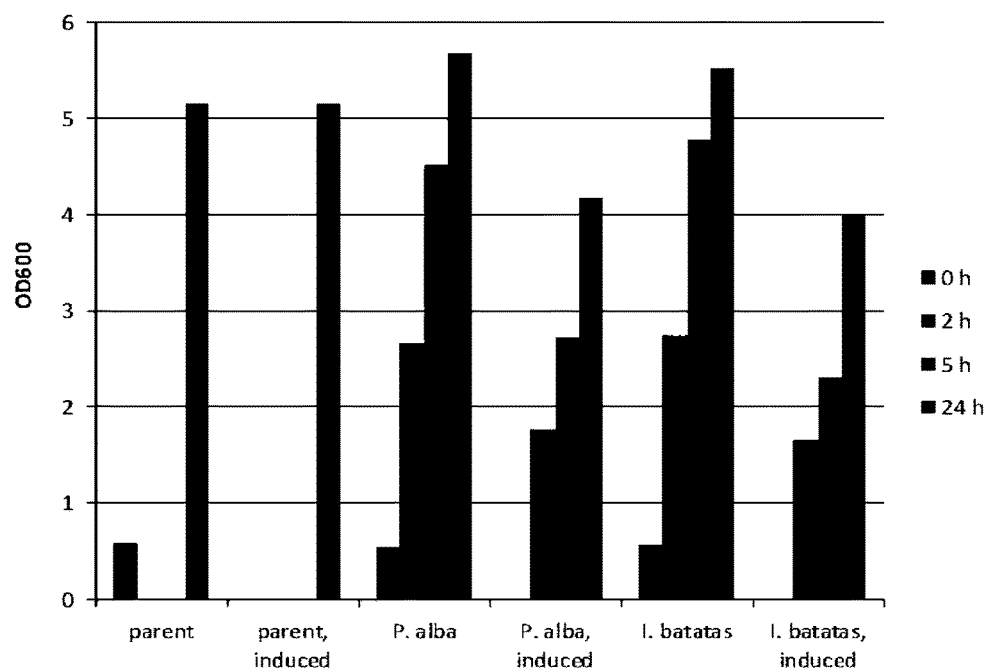

[Fig. 14]
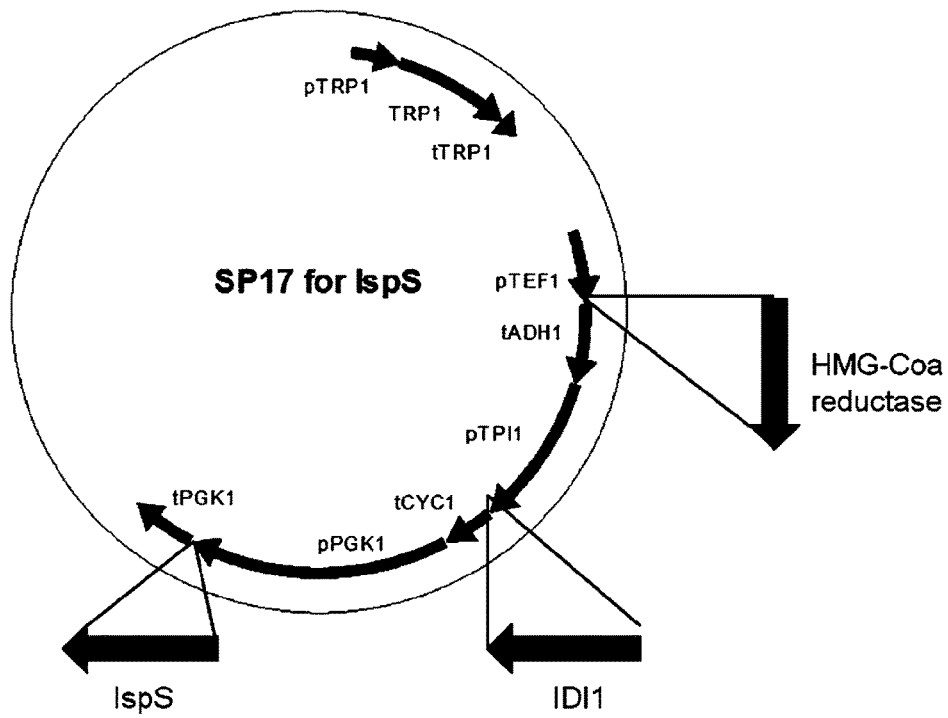
[Fig. 15]
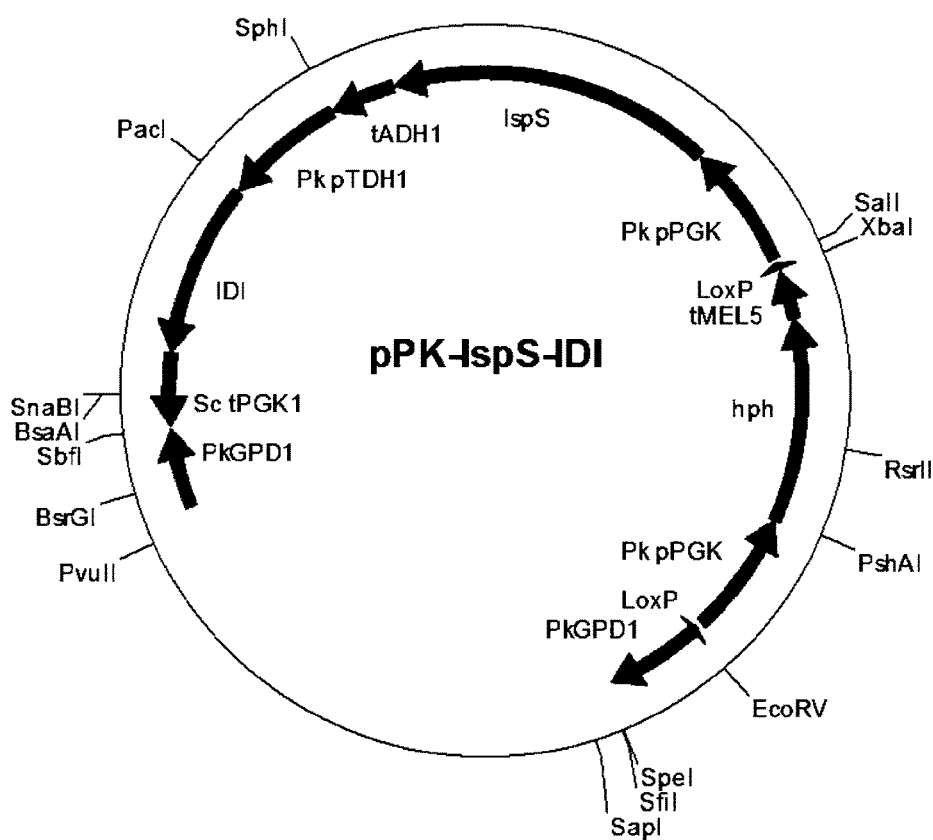

[Fig. 16]
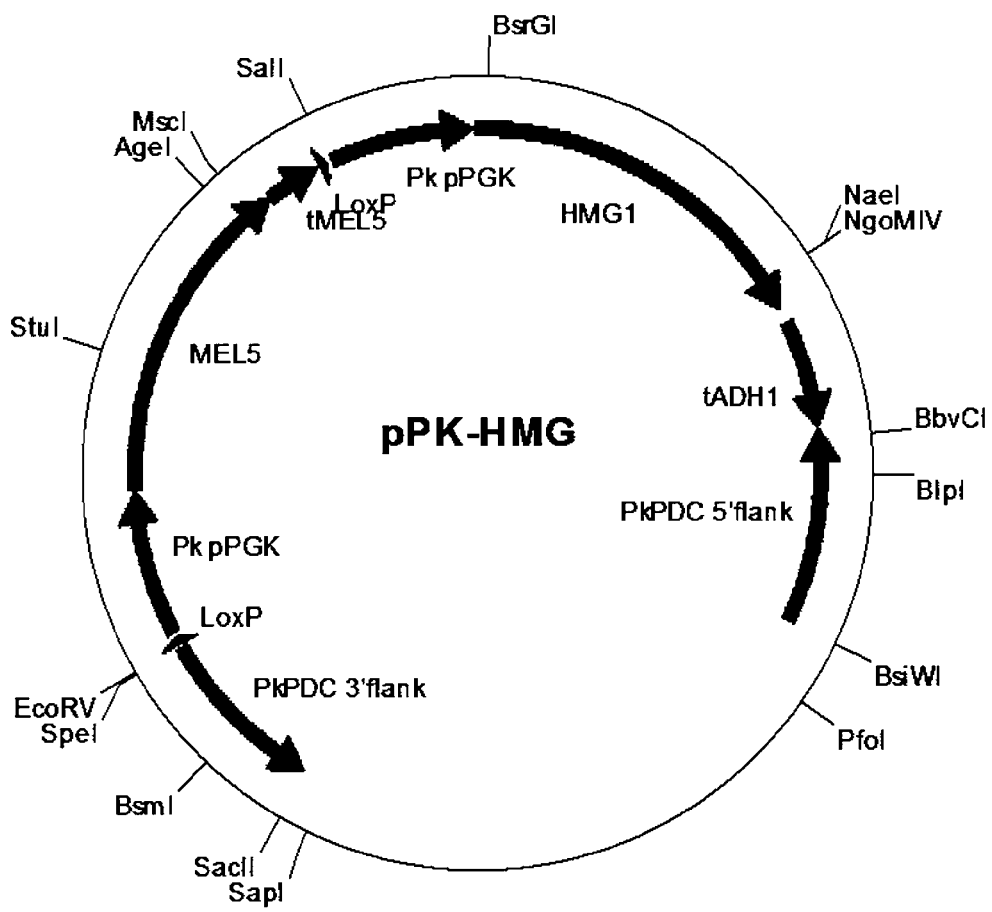

[Fig. 17]
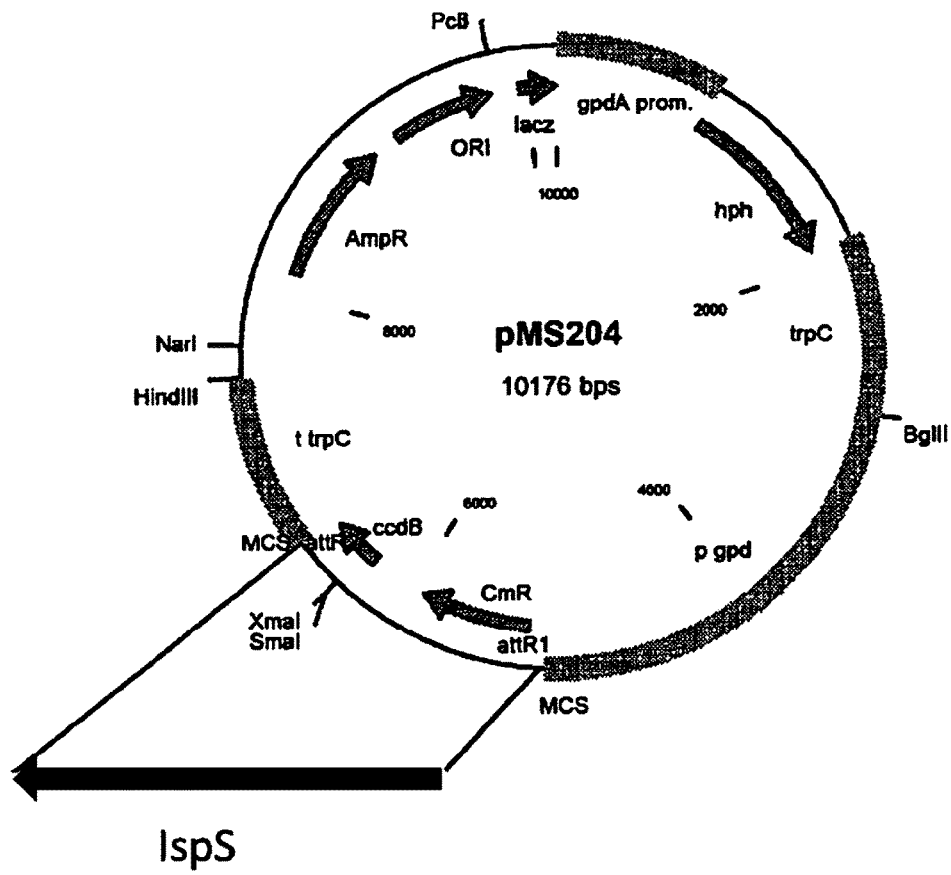
[Fig. 18]
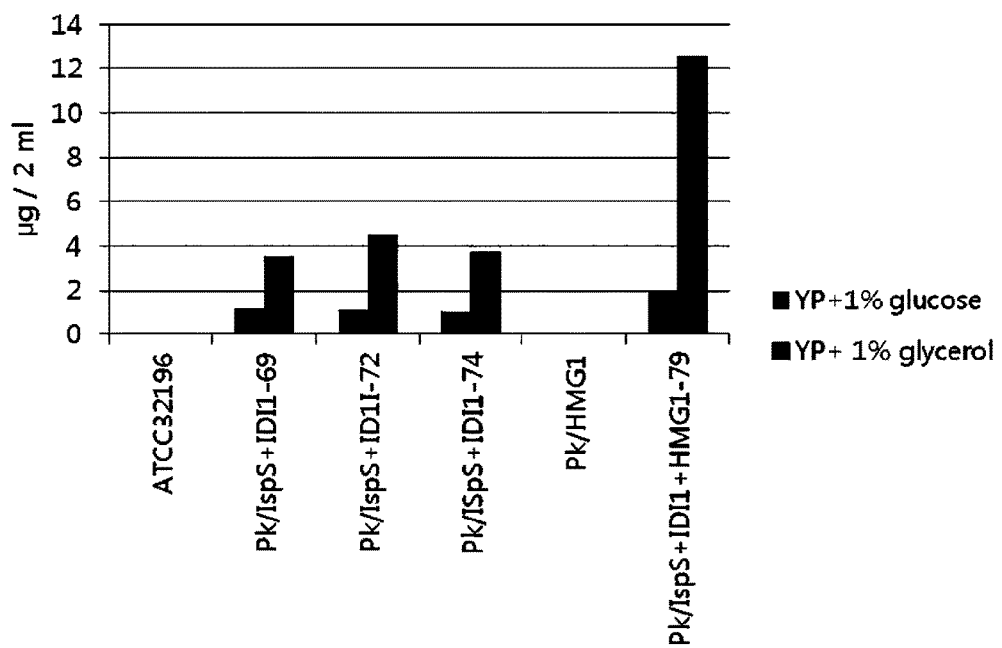

[Fig. 19]
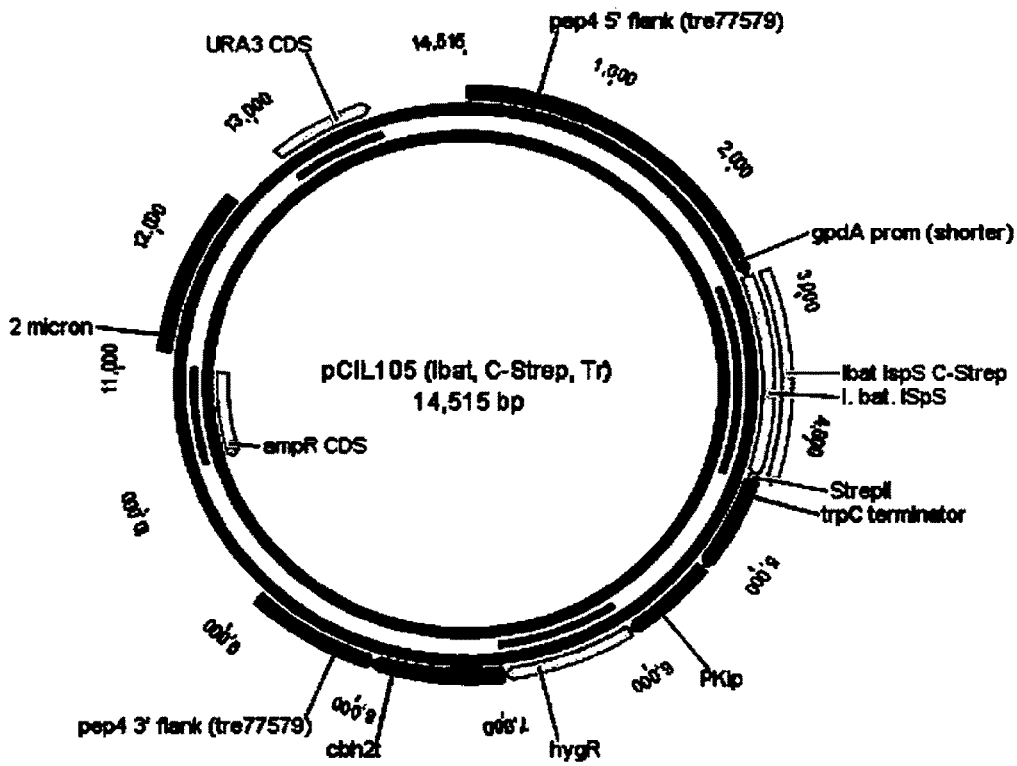
[Fig. 20]
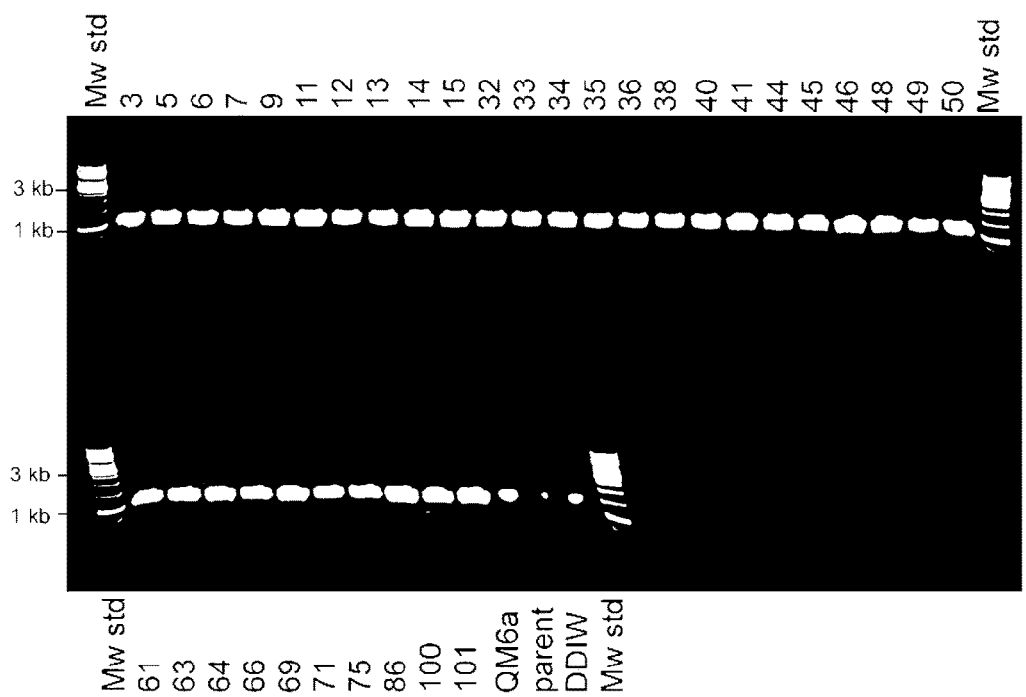

ISOPRENE SYNTHASE AND METHOD OF PREPARING ISOPRENE USING THEREOF

CROSS-REFERENCE TO RELATED APPLICATIONS

This application is the United States national phase of International Application No. PCT/KR2015/007851 filed Jul. 28, 2015, and claims priority to Korean Patent Application No. 10-2014-0095972 filed Jul. 28, 2014, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 1700617_ST25.txt. The size of the text file is 167,544 bytes, and the text file was created on Jan. 26, 2017.

TECHNICAL FIELD

The present invention relates to a novel isoprene synthase and a method of preparing isoprene using the same, and more specifically, to a polynucleotide encoding the novel isoprene synthase, a recombinant host cell having the polynucleotide introduced, and a method of preparing isoprene using the same.

BACKGROUND ART

Isoprenoids are isoprene polymers that find use in pharmaceuticals, neutraceuticals, flavors, fragrances, and rubber products. Supplies of natural isoprenoid, however, are restricted due to ecological concerns. For this reason, and in order to provide isoprenoid compositions having less impurities and greater uniformity, isoprenoids such as rubber are often produced synthetically. Isoprene (2-methyl-1,3-butadiene) is a volatile hydrocarbon that is insoluble in water and soluble in alcohol. Commercially viable quantities of isoprene can be obtained by direct isolation from petroleum C5 cracking fractions or by dehydration of C5 isoalkanes or isoalkenes (Weissermel and Arpe, Industrial Organic Chemistry, $4^{th}$ ed., Wiley-VCH, pp. 117-122, 2003). The C5 skeleton can also be synthesized from smaller subunits.

It would be desirable, however, to have a commercially viable method of producing isoprene that was independent of nonrenewable resources. Biosynthetic production of isoprene occurs by two distinct metabolic pathways (Julsing et al., Appl Microbiol Biotechnol, 75:1377-1384, 2007). In eukaryotes and archae, isoprene is formed via the mevalonate (MVA) pathway, while some eubacteria and higher plants produce isoprene via the methylerythritol phosphate (MEP) pathway. Isoprene emissions from plants are light and temperature-dependent and increase with the association to leaf development.

An isoprene-producing enzyme, isoprene synthase, has been identified in Aspen trees (Silver and Fall, *Plant Physiol*, 97:1588-1591, 1991; and Silver and Fall, *J Biol Chem*, 270:13010-13016, 1995) and is believed to be responsible for the in vivo production of isoprene from whole leaves. Bacterial production of isoprene has also been described (Kuzma et al., Curr Microbiol, 30:97-103, 1995; and Wilkins, *Chemosphere*, 32:1427-1434, 1996), and it varies in amount according to the phase of bacterial growth and the nutrient content of the culture medium (U.S. Pat. No. 5,849,970 to Fall et al.; and Wagner et al., *J* Bacteriol, 181:4700-4703, 1999).

The levels of isoprene obtainable through bacterial systems of the prior art, however, are insufficient for commercial uses. Thus, what the art needs is an effective and large scaled bacterial or microbial isoprene production process to provide feedstock for the manufacture of isoprene.

Accordingly, as a result of an effort for developing a method of preparing isoprene using a novel isoprene synthase gene having excellent isoprene productivity, the present inventors performed mining on a novel isoprene synthase gene, and confirmed that a recombinant microorganism transformed with the isoprene synthase gene has more excellent isoprene productivity than that of a host cell transformed with the isoprene synthase gene known in the art, thereby completing the present invention.

SUMMARY OF THE INVENTION

Technical Problem

An object of the present invention is to provide an isoprene synthase having excellent isoprene productivity and a gene encoding the isoprene synthase.

Another object of the present invention is to provide a recombinant host cell expressing an isoprene synthase and a method of preparing isoprene by culturing the recombinant host cell.

Solution to Problem

In order to achieve the foregoing objects, the present invention provides an isoprene synthase comprising an amino acid sequence of SEQ ID NO: 1; or an amino acid sequence having 70% or more sequence homology to the amino acid sequence of SEQ ID NO: 1.

In addition, the present invention provides a polynucleotide encoding the isoprene synthase as described above and a recombinant vector into which the polynucleotide is operably introduced.

Further, the present invention provides a recombinant host cell into which the polynucleotide or the recombinant vector as described above is introduced.

In addition, the present invention provides a polynucleotide comprising a nucleotide sequence of SEQ ID NO: 3 optimized by codon optimization of the polynucleotide sequence encoding the isoprene synthase for blue-green algae (cyanobacteria); and a recombinant vector into which the polynucleotide is operably introduced.

In addition, the present invention provides a polynucleotide comprising a nucleotide sequence of SEQ ID NO: 33 optimized by codon optimization of the polynucleotide sequence encoding the isoprene synthase for yeast; and a recombinant vector into which the polynucleotide is operably introduced.

Further, the present invention provides recombinant blue-green alga (cyanobacteria) or recombinant filamentous fungi; into which the polynucleotide comprising the nucleic acid sequence of SEQ ID NO: 3 as described above or the recombinant vector comprising the polynucleotide as described above is introduced.

Further, the present invention provides recombinant yeast; into which the polynucleotide comprising the nucleic acid sequence of SEQ ID NO: 33 as described above or the recombinant vector comprising the polynucleotide as described above is introduced.

In addition, the present invention provides a method of preparing isoprene including: (a) culturing the recombinant host cell as described above to prepare isoprene; and (b) obtaining the prepared isoprene.

Further, the present invention provides a method of preparing isoprene including: (a) culturing the recombinant blue-green algae (cyanobacteria), filamentous fungi or yeast as described above to prepare isoprene; and (b) obtaining the prepared isoprene.

BRIEF DESCRIPTION OF THE DRAWINGS

FIG. 1a and FIG. 1b show an amino acid sequence alignment result of *I. batatas*-derived isoprene synthase with known isoprene synthases (SEQ ID NOS: 37-51).

FIG. 2 is directed to multiple sequence alignment (MSA) result showing the sequence around the substrate binding amino acids in isoprene synthase (SEQ ID NOS: 52-66).

FIG. 3 shows a multiple sequence alignment (MSA) result to around the substrate-binding amino acid sequence (SEQ ID NOS: 67-96).

FIG. 4 shows a phylogenetic tree among isoprene synthase candidates.

FIG. 5 shows a multiple sequence alignment (MSA) result of the isoprene synthase candidates.

FIG. 6 shows a map of pETDuet-1 vector.

FIG. 7 shows an expression of an isoprene synthase of isoprene synthase clone comprising a pBAT4 construct (trc promoter) of *P. alba*- and *I. batatas*-derived isoprene synthase genes.

FIG. 8 shows isoprene productivity of the pBAT4 construct (trc promoter) comprising *P. alba*- and *I. batatas*-derived isoprene synthase genes.

FIG. 9 shows an expression of an isoprene synthase of an *E. coli* strain transformed into a pETDuet-1 vector having five kinds of isoprene synthases (*I. batatas, E. photiniifolius, P. alba, P. montana* and *A. hypogaea*) introduced thereinto.

FIG. 10 shows isoprene productivity of an *E. coli* strain transformed into a pETDuet-1 vector, in which five kinds of isoprene synthases (*I. batatas, E. photiniifolius, P. alba, P. montana* and *A. hypogaea*) are inserted.

FIG. 11 shows inhibition in growth of an *E. coli* strain transformed into a pETDuet-1 vector, in which five kinds of isoprene synthases (*I. batatas, E. photiniifolius, P. alba, P. montana* and *A. hypogaea*) are inserted.

FIG. 12 shows time dependent isoprene productivity after expression of isoprene synthases in an *E. coli* strain transformed into a pETDuet-1 vector in which *I. batatas* of isoprene synthases and *P. alba* of isoprene synthases, respectably, are inserted.

FIG. 13 shows time dependent growth inhibition in of an *E. coli* strain transformed into a pETDuet-1 vector, in which *I. batatas* of isoprene synthases and *P. alba* of isoprene synthases, respectably, are inserted.

FIG. 14 shows plasmid for expression of IspS, IDI and HMG-CoA reductase in *S. cerevisiae*.

FIG. 15 shows plasmid for expression of IspS, and IDI in *P. kudriavzevii*.

FIG. 16 shows plasmids for expression of HMG-reductase in *P. kudriavzevii*.

FIG. 17 shows plasmid for expression of IspS in filamentous fungi.

FIG. 18 shows isoprene production by *P. kudriavzevii* transformants in YP medium containing 1% glucose (grey) or 1% glycerol (black) as the carbon source.

FIG. 19 shows plasmid pCIL105 for expression of *I. batatas* IspS in *T. reesei*.

FIG. 20 shows PCR analysis for the presence of the IspS expression cassette in *T. reesei* transformed with pCIL105. Wild type strain QM6a, parent and DDIW are negative controls.

DESCRIPTION OF THE INVENTION

Unless defined otherwise, all the technical and scientific terms used herein have the same meanings as those generally understood by persons skilled in the art to which the present invention pertains. Generally, the nomenclature used herein are well known and commonly employed in the art.

In a first aspect of the present invention, the present invention provides an isoprene synthase comprising an amino acid sequence of SEQ ID NO: 1 or an amino acid sequence having at least 70%, preferably at least 75%, more preferably at least 80%, still more preferably at least 85%, still more preferably at least 90%, still more preferably at least 95%, more and more preferably at least 98%, most preferably at least 99% sequence homology to the amino acid sequence of SEQ ID NO: 1.

The isoprene synthase belongs to a terpene synthase (TPS)-B family, and has an amino acid sequence specifically conserved in isoprene synthase, referred to as an "isoprene score" (Sharkey et al., *Evolution*, 67:1026, 2013). Important amino acids in the isoprene synthase are F338, S445, F485 and N505 based on amino acid sequences of the *Populus alba*- and *Populus canescens*-derived isoprene synthases, and phenylalanine of F338 and F485 are important amino acids to decrease the size of a substrate-binding site so that large substrates such as geranyl diphosphate, farnesyl diphosphate, geranylgeranyl diphosphate, and the like, are not allowed to enter into an active site of an enzyme.

Therefore, the isoprene synthase of the present invention is characterized by comprising an amino acid sequence having 90% or more sequence homology to sequences at positions corresponding to RDRLMESFFW at position Nos. 257-266, FKLVTVLDDVYD at position Nos. 287-298, F369, SVS at position Nos. 394-396, FRLANDLSSS-KAEIERGETANSI at position Nos. 433-455, and YQYG-DAH at position Nos. 515-521 in an amino acid sequence of SEQ ID NO: 1. In addition, the isoprene synthase of the present invention is characterized by having at positions corresponding to the positions in SEQ ID NO: 1 at least one, preferably at least two, more preferably at least three, still more preferably at least four of the amino acids W266, F287, F369, F433, N453 and Y515.

The isoprene synthase of SEQ ID NO: 1 of the present invention comprises an amino acid sequence derived from sweet potato (*Ipomoea batatas*).

Figure 2:
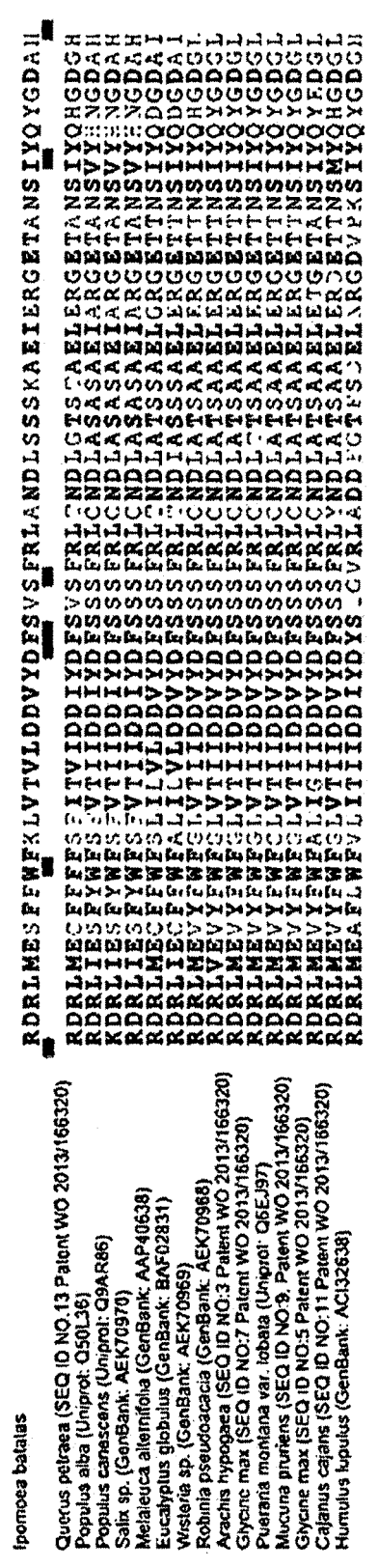

An amino acid sequence alignment result of *I. batatas*-derived isoprene synthase is shown in FIG. 1a and FIG. 1b, and an amino acid sequence alignment result of isoprene synthase candidates including *P. alba*-, *A. hypogaea*-derived isoprene synthases which are two known isoprene synthases, as a reference is shown in FIG. 2.

As a result of searching patent sequence database based on *I. batatas*-derived isoprene synthase having an amino acid sequence of SEQ ID NO: 1 according to the present invention, it was confirmed that the isoprene synthase derived from sweet potato of the present invention has 56% sequence homology to *Quercus petraea*-derived isoprene synthase (US Patent Application Publication No. 2013/0330709) and has low sequence homology to the isoprene synthase known in the related art.

In a second aspect of the present invention, the present invention provides a polynucleotide encoding the isoprene synthase.

In the present invention, the polynucleotide may be codon-optimized for microorganisms selected from the group consisting of *E. coli, bacillus* genus strain, blue-green algae (cyanobacteria), yeast and filamentous fungi. Also the introns may be removed from the original gene. In the present invention the term "polynucleotide" is used to mean the gene in its original or modified form or the coding sequence in its original or modified form.

The codon optimization in the present invention means that a codon having an average codon frequency less than 12% on the microorganism is substituted with a codon having an average codon frequency more than 12% on the microorganism.

In an exemplary embodiment of the present invention, with a target of a isoprene synthase polynucleotide of SEQ ID NO: 2, the codon optimization was performed to enable expression in either *Synechocystis* sp. (strain PCC6803), which is blue-green algae cyanobacteria, or *E. coli* (SEQ ID NO: 3). This same codon optimized nucleotide sequence for bacteria can be used also for filamentous fungi. In an exemplary embodiment of the present invention SEQ ID NO:3 was used for the filamentous fungus *Trichoderma*.

In another exemplary embodiment of the present invention, with a target of an isoprene synthase polynucleotide of SEQ ID NO: 2, the codon usage was optimized for *S. cerevisiae* (SEQ ID NO:33) to enable expression either in *S. cerevisiae* or *Pichia* (*P. kudriavzevii*).

Therefore, in a preferred embodiment of the present disclosure, the polynucleotide encoding the isoprene synthase might comprise any one nucleotide sequence of SEQ ID NOs: 2, 3 or 33, but the present invention is not limited thereto.

In a third aspect of the present invention, the present invention provides a polynucleotide encoding an isoprene synthase comprising a nucleotide sequence of SEQ ID NO: 3 by codon optimization of the polynucleotide encoding the isoprene synthase for blue-green algae (cyanobacteria), and *E. coli*, useful also for other bacteria and filamentous fungi, in particular *Trichoderma* and *Aspergillus*.

In a fourth aspect of the present invention, the present invention provides a polynucleotide encoding an isoprene synthase comprising a nucleotide sequence of SEQ ID NO: 33 by codon optimization of the polynucleotide encoding the isoprene synthase for *Saccharomyces cerevisiae*, useful also for *Saccharomyces, Pichia* and other yeasts.

In a fifth aspect of the present invention, the present invention provides a recombinant vector into which the polynucleotide is operably introduced; and a recombinant host cell into which the polynucleotide or the recombinant vector is introduced.

The recombinant vector in the present invention may contain a promoter for expressing the polynucleotide.

Examples of the promoter contained in the recombinant vector could include psbA2, trc, rbcL, petJ, psaA, psaB, tac, cpcB, petC or lac promoters for expression in blue-green algae (cyanobacteria), PGK1, TPI1, TDH, PDC1, FBA1, ENO1, ENO2, PYK1, ADH1, or TEF1 promoters for expression in yeast, preferably the promoter is selected from the group consisting of PGK1, TPI1 and TEF1 for expressing in yeast, cbh1, gpdA, glaA, pdc or exlA promoters for expression in filamentous fungi, and a CMV35S promoter for expression in a plant cell, but the present invention is not limited thereto.

In a preferred embodiment of the present invention, a polynucleotide sequence is contained in plasmids. In another preferred embodiment of the present invention, a polynucleotide sequence is incorporated into the genome of a host cell. In some preferred embodiments of the present invention, a host is selected from the group consisting of gram-positive bacterial cells, gram-negative bacterial cells, filamentous fungal cells, and yeast cells, but the present invention is not limited thereto.

In some preferred embodiments of the present invention, *escherichia* species (*E. coli*), *pantoea* species (*Pantoea citrea*), *bacillus* species (*Bacillus subtilis*), *yarrowia* species (*Yarrowia lipolytica*), and *trichoderma* species (*Trichoderma reesei*), but the present invention is not limited thereto. In some preferred embodiments, the host cell is cultured in a medium containing carbon sources selected from the group consisting of $CO_2$, bicarbonate, glucose, glycerol, glycerine, dihydroxyacetone, yeast extract, biomass, molasses, sucrose, galactose, sorbose, sorbitol, xylose, arabinose, cellulose, xylan, lactose and oil, but not limited thereto.

Preferably, the host cell of the present invention may be blue-green algae (cyanobacteria), yeast, filamentous fungi, or plant cells.

In a preferred embodiment of the present invention, the filamentous fungi may be *Trichoderma* genus, *Mucor* genus, *Mortierella* genus, *Neurospora* genus or *Aspergillus* genus, advantageously the filamentous fungi is *Trichoderma* or *Aspergillus* genus and the plant cell may be *Nicotiana* genus, *Catharantus* genus or *Hyroscyamus* genus plant cells.

In a sixth aspect of the present invention, the present invention provides a polynucleotide comprising a nucleotide sequence of SEQ ID NO: 3 by codon optimization of the polynucleotide encoding the isoprene synthase on blue-green algae (cyanobacteria), useful also for other bacteria and filamentous fungi, and a recombinant vector into which the polynucleotide is operably introduced; and a recombinant blue-green algae (cyanobacteria), bacteria or filamentous fungi into which the polynucleotide or the recombinant vector is introduced.

In a seventh aspect of the present invention, the present invention provides a polynucleotide comprising a nucleotide sequence of SEQ ID NO: 33 by codon optimization of the polynucleotide encoding the isoprene synthase on *Saccharomyces cerevisiae* useful for *Saccharomyces, Pichia* and other yeasts, and a recombinant vector into which the polynucleotide is operably introduced; and a recombinant yeast into which the polynucleotide or the recombinant vector is introduced.

In the present invention, the recombinant vector may comprise psbA2, trc, rbcL, petJ, psaA, psaB, tac, cpcB, petC or lac promoter for expression in blue-green algae (cyanobacteria).

Preferably, the blue-green algae may be unicellular blue-green algae or multicellular blue-green algae. The unicellular blue-green algae may be *Synechocystis* genus or *Synechococcus* genus strain, and the multicellular blue-green algae may be *Gloeocapsa* genus or filamentous cyanobacteria.

In a preferred embodiment of the present invention, the filamentous cyanobacteria may be *Nostoc* genus, *Anabaena* genus or *Arthospira* genus, and the yeast may be *Saccharomyces* genus, *Pichia* genus, *Candida* genus, *kazachstania* genus, *Kluyveromyces* genus, *Hansenula* genus, *Rhodosporidium* genus, *Cryptococcus* genus or *Yarrowia* genus.

The polynucleotide is operably linked when being disposed with other nucleic acid sequences in a functional relationship. This may be polynucleotide and a regulatory sequence(s) linked in the manner of enabling polynucleotide expression when appropriate molecules (for example, transcriptional activation protein) are bound to the regulatory sequence(s). For example, nucleotide sequence for a pre-sequence or a secretion leader is operably linked to nucleotide sequence for a polypeptide when being expressed as a pre-protein participating in secretion of polypeptide; a promoter or an enhancer is operably linked to a coding sequence when having an influence on transcription of sequence; or a ribosome binding site is operably linked to a coding sequence when having an influence on transcription of sequence; or a ribosome binding site is operably linked to a coding sequence when being disposed so that translation is easily performed. In general, term: 'operably linked' means that the linked nucleotide sequences are contacted with each other, or in the case of the secretion leader, contacted with the nucleotide sequence and present within a leading frame. However, the enhancer does not need to have a contact. The link of the sequences is performed by ligation (linkage) in a convenient restriction enzyme site. When the site does not exist, a synthetic oligonucleotide adaptor or a linker according to general method is used.

A method of inserting the polynucleotide into the genome of a host cell may be a generally known genetic engineering method, and a non-viral transfer method may include electroporation, lipofection, microinjection, biolistic, virosome, liposome, immuno-liposome, multivalent cation or lipid:nucleic acid conjugate, naked DNA, artificial virion and chemical-enhanced uptake of DNA. Sonoporation, for example, a method using a sonitron 2000 system (Rich-Mar) may be used for transfer of nucleic acids, and other representative nucleic acid transfer systems include Amaxa Biosystems (Cologne, Germany), Maxcyte, Inc. (Rockville, Md.) and BTX Molesular Syetem (Holliston, Mass.). The lipofection method is disclosed in U.S. Pat. Nos. 5,049,386, 4,946,787, and 4,897,355, and lipofection reagent is commercially available, for example, Transfectam™ and Lipofectin™. Cationic and neutral lipids that are suitable for efficient receptor-recognition lipofection of polynucleotides include those of Feigner (WO 91/17424 and WO 91/16024), and may be transferred to cells via ex-vivo administration or to target tissues via in-vivo administration. A method of preparing lipid:nucleic acid complex, containing targeted liposomes such as immunolipid complexes, is well known in the art (Crystal, Science., 270:404-410, 1995; Blaese et al., Cancer Gene Ther., 2:291-297, 1995; Behr et al., Bioconjugate Chem., 5:382389, 1994; Remy et al., Bioconjugate Chem., 5:647-654, 1994; Gao et al., Gene Therapy., 2:710-722, 1995; Ahmad et al., Cancer Res., 52:4817-4820, 1992; U.S. Pat. Nos. 4,186,183; 4,217,344; 4,235,871; 4,261,975; 4,485,054; 4,501,728; 4,774,085; 4,837,028; 4,946,787).

The tropism of a retrovirus may be altered by unification with foreign envelope proteins and thereby expand kinds of target cells. A lentiviral vector is a type of retroviral vector that is able to transduce or infect non-dividing cells and produce high viral titers. A retroviral gene transfer system is determined depends on the target tissue. The retroviral vector includes cis-acting long terminal repeats with packaging capacity for 6-10 kb of foreign sequence. The minimum cis-acting LTRs which are sufficient for replication and packaging of the vectors may be used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (Buchscher et al., J. Virol., 66:2731-2739, 1992; Johann et al., J. Virol., 66:1635-1640, 1992; Sommerfelt et al., Virol., 176:58-59, 1990; Wilson et al., J. Virol., 63:2374-2378, 1989; Miller et al., J. Virol., 65:2220-2224, 1991).

In a case of temporarily expressing a sucrose phosphorylase protein, an adenoviral based system may be frequently used. Adenoviral based vectors are capable of very high transduction efficiency in many cell types and do not require cell division. When using the vectors, high titer and high levels of expression may be obtained and a mass-production is possible with a relatively simple system. In addition, Adeno-associated virus ("AAV") vectors are also used to transduce cells with target nucleic acids, for example, for in vitro production of nucleic acids and peptides, and for in vivo and ex vivo gene therapy (West et al., Virology., 160:38-47, 1987; U.S. Pat. No. 4,797,368; WO 93/24641; Kotin, Human Gene Therapy., 5:793-801, 1994; Muzyczka, J. Clin. Invest., 94:1351, 1994), and a construction of recombinant AAV vectors were already known (U.S. Pat. No. 5,173,414; Tratschin et al., Mol. Cell. Biol., 5:3251-3260, 1985; Tratschin, et al., Mol. Cell. Biol., 4:20722081, 1984; Hermonat & Muzyczka, PNAS., 81:6466-6470, 1984; Samulski et al., J Virol., 63:3822-3828, 1989). In clinical trials, at least six viral vector approaches are currently available for gene transfer, which utilize approaches that involve complementation of defective vectors by genes inserted into helper cell lines to generate the transducing agent. pLASN and MFG-S are examples of retroviral vectors that have been used in clinical trials (Dunbar et al., Blood., 85:3048, 1995; Kohn et al., Nat. Med., 1:1017, 1995; Malech et al., PNAS., 94:12133, 1997), and PA317/pLASN is the first therapeutic vector used in a gene therapy trial (Blaese et al., Science., 270:475-480, 1995), and transduction efficiencies of 50% or greater have been observed for MFG-S packaged vectors (Ellem et al., Immunol Immunother., 44(1):10-20, 1997; Dranoff et al., Hum. Gene Ther., 1:111-2, 1997).

Recombinant adeno-associated virus vectors (rAAV) are a promising alternative gene delivery systems based on the defective and nonpathogenic parvovirus adeno-associated type 2 virus. All vectors are derived from a plasmid that retains the AAV 145 bp inverted terminal repeats flanking the transgene expression cassette. Efficient gene transfer and stable transgene delivery due to integration into the genomes of the transduced cell are key features for this vector system (Wagner et al., Lancet., 351:9117, 1998; Kearns et al., Gene Ther., 9:748-55, 1996).

In an eighth aspect of the present invention, the present invention provides a method of preparing isoprene including: (a) culturing the recombinant host cell as described above to prepare isoprene; and (b) obtaining the prepared isoprene.

The culturing of the step (a) may be performed in a medium containing carbon sources selected from the group consisting of $CO_2$, bicarbonate, glucose, glycerol, glycerine, dihydroxyacetone, yeast extract, biomass, molasses, sucrose, galactose, sorbose, sorbitol, xylose, arabinose, cellulose, xylan, lactose and oil.

In a ninth aspect of the present invention, the present invention provides a method of preparing isoprene including: (a) culturing the recombinant blue-green algae (cyanobacteria), bacteria, recombinant filamentous fungi or yeast as described above to prepare isoprene; and (b) obtaining the prepared isoprene.

The methods may additionally include (c) polymerizing isoprene.

Unless otherwise indicated, the practice of the present invention involves conventional techniques commonly used in molecular biology, microbiology, and recombinant DNA, which are within the skill of the art. Such techniques are known to those of skill in the art and are described in numerous texts and reference works (See e.g., Sambrook et al., "Molecular Cloning: A Laboratory Manual," Second Edition, Cold Spring Harbor, 1989; and Ausubel et al., "Current Protocols in Molecular Biology," 1987).

Unless defined otherwise herein, all technical and scientific terms used herein have the same meaning as commonly understood by one of ordinary skill in the art to which this invention pertains. For example, Singleton and Sainsbury, Dictionary of Microbiology and Molecular Biology, 2d Ed., John Wiley and Sons, NY (1994); and Hale and Marham, The Harper Collins Dictionary of Biology, Harper Perennial, NY (1991) provides those of skill in the art with a general dictionary of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole.

In combination with isoprene synthase expression of other genes contributing to isoprene production can be introduced into blue green algae (cyanobacteria), bacteria, filamentous fungi or yeast, cells. For example, the idi gene coding for isopentenyl-diphosphate delta-isomerase (EC 5.3.3.2) can be introduced to enhance conversion of isopentenyl diphosphate (IPP) to dimethylallyl diphosphate (DMAPP) that is the substrate of isoprene synthase. Also one or more genes coding for the mevalonate pathway components, mevalonate kinase (EC2.7.1.36), phosphomevalonate kinase (EC2.7.4.2), pyrophoshomevalonate decarboxylase (EC 4.1.1.33), acetoacetyl-CoA thiolase (EC2.3.1.9), HMG-CoA synthase (EC2.3.3.10) or HMG-CoA reductase (EC1.1.1.34) can be cloned under a suitable cyanobacteria, bacteria, filamentous fungi or yeast promoter that allow expression in these hosts. Two or more genes are expressed as a transcriptional fusion under the control or under the transcriptional control of a cyanobacteria or bacteria promoter. When two or more genes are expressed in, filamentous fungi or yeast, each gene is expressed under the control of an individual filamentous fungal or yeast promoter. Advantageous for expression of isoprene synthase is for example a combination of IDI and HMG reductase in filamentous fungi and in yeast, in particular in *Pichia* and *Saccharomyces*.

As used herein, the term 2-methyl-1,3-butadiene (CAS #78-79-5) ("isoprene") refers to the direct and final volatile C5 hydrocarbon product from the elimination of pyrophosphate from 3,3-dimethylallyl pyrophosphate (DMAPP), and does not involve the linking or polymerization of [an] IPP molecule(s) to [a] DMAPP molecule(s).

As used herein, the terms "isoprene synthase," and "IspS," refer to the enzymes that catalyze the elimination or pyrophosphate from diemethylallyl diphosphate (DMAPP) to form isoprene.

In some embodiments, the term "IspS" refers to a naturally occurring mature enzyme or portion thereof.

The present invention comprises proteins comprising an amino acid sequence having 70% or more identity with the amino acid sequence of Isoprene synthase from sweet potato, the proteins comprise "variant proteins".

In some preferred embodiments, variant proteins differ from a parent protein (e.g., set forth as SEQ ID NO:1) by a small number of amino acid residues. The number of differing amino acid residues may be one or more, preferably 1, 2, 3, 4, 5, 10, 15, 20, 30, 40, 50, or more amino acid residues. In some preferred embodiments, the number of different amino acids between variants is between 1 and 10. In some particularly preferred embodiments, related proteins and particularly variant proteins comprise at least 35%, 40%, 45%, 50%, 55%, 60%, 65%, 70%, 75%, 80%, 85%, 90%, 95%, 97%, 98%, or 99% amino acid sequence identity. Additionally, a related protein or a variant protein as used herein refers to a protein that differs from another related protein or a parent protein in the number of prominent regions. For example, in some embodiments, variant proteins have 1, 2, 3, 4, 5, or 10 corresponding prominent regions that differ from the parent protein.

In present invention, the proteins comprising an amino acid sequence having 70% identity with amino acid sequence set forth as SEQ ID NO:1 of Isoprene synthase can be generated with several methods including but not limited to site-saturation mutagenesis, scanning mutagenesis, insertional mutagenesis, random mutagenesis, site-directed mutagenesis, and directed-evolution, as well as various other recombinatorial approaches.

As used herein the term "gene" refers to a polynucleotide (e.g., a DNA segment) that encodes a polypeptide and includes regions preceding and following the coding regions as well as intervening sequences (introns) between individual coding segments (exons). Polynucleotides introduced into host cells may comprise the coding region without introns and with or without the preceding or following regions of the original gene. Furthermore the codons may be modified to be more suitable for the host cell.

As used herein, "homology" refers to sequence similarity or identity, with identity being preferred. This homology is determined using standard techniques known in the art (See e.g., Smith and Waterman, Adv Appl Math, 2:482, 1981; Needleman and Wunsch, J Mol Biol, 48:443, 1970; Pearson and Lipman, Proc Natl Acad Sci USA, 85:2444, 1988; programs such as GAP, BESTFIT, FASTA, and TFASTA in the Wisconsin Genetics Software Package, Genetics Computer Group, Madison, Wis.; and Devereux et al., Nucl Acid Res, 12:387-395, 1984).

As used herein, an "analogous sequence" is one wherein the function of the polynucleotide is essentially the same as the polynucleotide based on sweet potato isoprene synthase (IspS). Additionally, analogous polynucleotides include at least 45%, 50%, 55%, 60%, 65%, 70%, 75%, 80%, 85%, 90%, 95%, 97%, 98%, 99% or 100% sequence identity with the amino acid sequence of the batate isoprene synthase. In additional embodiments more than one of the above properties applies to the sequence. Analogous sequences are determined by known methods of sequence alignment. A commonly used alignment method is BLAST, although as indicated above and below, there are other methods that also find use in aligning sequences.

Thus, "percent (%) nucleic acid sequence identity" is defined as the percentage of nucleotide residues in a candidate sequence that is identical to the nucleotide residues of the starting sequence (i.e., the sequence of interest). A preferred method utilizes the BLASTN module of WU-BLAST-2 set to the default parameters, with overlap span and overlap fraction set to 1 and 0.125, respectively.

As used herein, "recombinant" includes reference to a cell or vector, that has been modified by the introduction of a heterologous nucleic acid sequence or that the cell is derived from a cell so modified. Thus, for example, recombinant cells expresses genes that are not found in identical form within the native (non-recombinant) form of the cell or express native genes that are otherwise abnormally expressed, under expressed or not expressed at all as a result of deliberate human intervention. "Recombination," "recombining," and generating a "recombined" nucleic acid are generally the assembly of two or more nucleic acid fragments wherein the assembly gives rise to a chimeric gene.

As used herein, the terms "amplification" and "gene amplification" refer to a process by which specific polynucleotides are disproportionately replicated such that the amplified polynucleotide becomes present in a higher copy number than was initially present in the genome. In some embodiments, selection of cells by growth in the presence of a drug (e.g., an inhibitor of an inhibitable enzyme) results in the amplification of either the endogenous gene encoding the gene product required for growth in the presence of the drug or by amplification of exogenous (i.e., input) sequences encoding this gene product, or both.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the terms "amplifiable marker," "amplifiable gene," and "amplification vector" refer to a polynucleotide or a vector comprising a polynucleotide, which permits the amplification of that polynucleotide under appropriate growth conditions.

"Homologous sequences" as used herein means a nucleic acid or polypeptide sequence having 100%, 99%, 98%, 97%, 96%, 95%, 94%, 93%, 92%, 91%, 90%, 88%, 85%, 80%, 75%, or 70% sequence identity to another nucleic acid or polypeptide sequence when optimally aligned for comparison. In some embodiments, homologous sequences have between 85% and 100% sequence identity, while in other embodiments there is between 90% and 100% sequence identity, and in more preferred embodiments, there is 95% and 100% sequence identity.

As used herein "amino acid" refers to peptide or protein sequences or portions thereof. The terms "protein," "peptide," and "polypeptide" are used interchangeably.

As used herein, the term "heterologous protein" refers to a protein or polypeptide that does not naturally occur in the host cell. Examples of heterologous proteins include enzymes such as isoprene synthases. In some embodiments, the polynucleotides encoding the proteins are naturally occurring genes, while in other embodiments mutated and/or synthetic polynucleotides are used.

As used herein, "homologous protein" refers to a protein or polypeptide native or naturally occurring in a cell. In preferred embodiments, the cell is a Gram-negative cell, while in particularly preferred embodiments the cell is an *Escherichia* host cell.

An enzyme is "overexpressed" in a host cell if the enzyme is expressed in the cell at a higher level that the level at which it is expressed in a corresponding wild-type cell.

The terms "protein" and "polypeptide" are used interchangeability herein. The 3-letter code for amino acids as defined in conformity with the IUPAC-IUB Joint Commission on Biochemical Nomenclature (JCBN) is used through out this disclosure. It is also understood that a polypeptide may be coded for by more than one nucleotide sequence due to the degeneracy of the genetic code.

The term "mature" form of a protein or peptide refers to the final functional form of the protein or peptide. To exemplify, a mature form of sweet potato isoprene synthase includes the amino acid sequence of SEQ ID NO:1.

The term "precursor" form of a protein or peptide refers to a mature form of the protein having a prosequence operably linked to the amino or carbonyl terminus of the protein. The precursor may also have a "signal sequence" operably linked, to the amino terminus of the prosequence. The precursor may also have additional polynucleotides that are involved in post-translational activity (e.g., polynucleotides cleaved therefrom to leave the mature form of a protein or peptide).

"Naturally occurring enzyme" refers to an enzyme having the unmodified amino acid sequence identical to that found in nature. Naturally occurring enzymes include native enzymes, those enzymes naturally expressed or found in the particular microorganism.

The term "identical" in the context of two nucleic acids or polypeptide sequences refers to the residues in the two sequences that are the same when aligned for maximum correspondence, as measured using one of the following sequence comparison or analysis algorithms.

The term "optimal alignment" refers to the alignment giving the highest percent identity score. "Percent sequence identity," "percent amino acid sequence identity," "percent gene sequence identity," and/or "percent nucleic acid/polynucleotide sequence identity," with respect to two amino acid, polynucleotide and/or gene sequences (as appropriate), refer to the percentage of residues that are identical in the two sequences when the sequences are optimally aligned. Thus, 80% amino acid sequence identity means that 80% of the amino acids in two optimally aligned polypeptide sequences are identical.

The phrase "substantially identical" in the context of two nucleic acids or polypeptides thus refers to a polynucleotide or polypeptide that comprising at least 70% sequence identity, preferably at least 75%, preferably at least 80%, preferably at least 85%, preferably at least 90%, preferably at least 95%, preferably at least 97%, preferably at least 98% and preferably at least 99% sequence identity as compared to a reference sequence using the programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, "corresponding to," refers to a residue at the enumerated position in a protein or peptide, or a residue that is analogous, homologous, or equivalent to an enumerated residue in a protein or peptide. As used herein, "corresponding region," generally refers to an analogous position along related proteins or a parent protein.

As used herein, the terms "multiple sequence alignment" and "MSA" refer to the sequences of multiple homologs of a starting gene that are aligned using an algorithm (e.g., Clustal W).

As used herein, the terms "consensus sequence" and "canonical sequence" refer to an archetypical amino acid sequence against which all variants of a particular protein or sequence of interest are compared. The terms also refer to a sequence that sets forth the nucleotides that are most often present in a DNA sequence of interest. For each position of a gene, the consensus sequence gives the amino acid that is most abundant in that position in the MSA.

As used herein, the term "consensus mutation" refers to a difference in the sequence of a starting gene and a consensus sequence. Consensus mutations are identified by comparing the sequences of the starting gene and the consensus sequence obtained from a MSA. In some embodiments, consensus mutations are introduced into the starting gene such that it becomes more similar to the consensus sequence. Consensus mutations also include amino acid changes that change an amino acid in a starting gene to an amino acid that is more frequently found in an MSA at that position relative to the frequency of that amino acid in the starting gene. Thus, the term consensus mutation comprises all single amino acid changes that replace an amino acid of the starting gene with an amino acid that is more abundant than the amino acid in the MSA.

As used herein, the term "headspace" refers to the vapor/air mixture trapped above a solid or liquid sample in a sealed vessel.

Unless otherwise noted, all component or composition levels are in reference to the active level of that component or composition, and are exclusive of impurities, for example, residual solvents or by-products, which may be present in commercially available sources.

Enzyme components weights are based on total active protein. All percentages and ratios are calculated by weight unless otherwise indicated. All percentages and ratios are calculated based on the total composition unless otherwise.

EXAMPLES

Hereinafter, the present invention will be described in detail with reference to the following Examples. However, the following examples are only for exemplifying the present invention and it will be obvious to those skilled in the art that the scope of the present invention is not construed to be limited to these examples.

Example 1

Genome Mining for Novel Isoprene Synthase Genetic Search

The isoprene synthase belongs to a terpene synthase (TPS)-B family, and has an amino acid specifically conserved in isoprene synthase, referred to as an "isoprene score" (Sharkey et al., Evolution, 67: 1026, 2013). Important amino acids in the isoprene synthase are F338, S445, F485 and N505 based on amino acid numbering of sequences of the *Populus alba*- and *Populus canescens*-derived isoprene synthases, and phenylalanines of F338 and F485 respectively are amino acids which have an important role to decrease a size of a substrate-binding site so that large substrates such as geranyl diphosphate, farnesyl diphosphate, geranylgeranyl diphosphate, and the like, are not allowed to enter into an active site of an enzyme.

Bi-functional myrcene synthase of *Humulus lupulus* having low activity as compared to other isoprene synthases lacks F485. N505 has a critical role to determine an ion requirement of terpene synthases, and terpene synthase without an ion requirement has cationic lysine, serine, or asparagine positioned at position No. 505. S445 is present at a first position of triple serine motif, and other TPS-b protein usually has valine (Val) and isoleucine (Ile) in the middle of the triple serine motif; however, S445 present at the first position of the triple serine motif is conserved in almost all Tps-b family and thus, it is judged that S446 positioned in the middle of the triple serine motif is not important in preparation of isoprene.

In addition, W317 and Y565, which are amino acids present in almost all TPS family sequences, are essential to define a size of a substrate-bound pocket.

In addition, N489 is conserved in isoprene/ocimene clade of the Tps-B

In order to determine isoprene Synthase candidates, a homology-based database search was conducted. Isoprene synthase sequences using Query sequence are as follows:

1) *Populus alba* (white poplar, Uniport: Q50L36), *Populus canescens* (grey poplar, Uniprot: Q9AR86, PDB: 3N0G) and *Pueraria montana* var. *lobata* (kudzu wine, Uniprot: Q6EJ97);

2) *Arachis hypogaea* (peanut, SEQ ID No: 3), *Glycine max* (soybean, SEQ ID No:5 and SEQ ID No:7), *Mucuna pruriens* (velvet bean, SEQ ID No:9), *Cajanus cajans* (pigeon pea, SEQ ID No:11) and *Quercus petraea* (oak, SEQ ID No:13) derived from WO 2013/166,320A1;

3) *Wisteria* sp. (GenBank: AEK70969), *Robinia pseudoacacia* (GenBank: AEK70968), *Melaleuca alternifolia* (GenBank: AAP40638), *Eucalyptus globulus* (GenBank: BAF02831), *Salix* sp. (GenBank: AEK70970) and a myrcene synthase from *Humulus lupulus* (GenBank: ACI32638) derived from Sharkey list (Sharkey et al., Evolution, 67: 1026, 2013); and 4) 2-methyl-3-buten-2-ol (MBO) synthase (GenBank: AEB53064)(Gray et al., J Biol Chem, 286: 20582, 2011) derived from *Pinus sabiniana*.

In addition, several sequences derived from poplar genus were included as a reference.

The homology-based search was performed in GenBank protein databases (nr, pat and env_nr) using Uniport (SwissProt and TrEMBL) and blastp, and was performed in GenBank nucleotide databases (tsa_nt, env_nt and pat) using tblastn, and extracted when E-value is less than 1e-30.

Additionally, Uniprot/SwisProt sequences with InterPro domain annotation of "Terpene synthase, metal binding domain" protein family (PFAM: PF03936, Interpro: IPR005630) were retrieved.

The searched nucleotide sequence was translated into an amino acid sequence by GeneWise program.

tsa_nt (GenBank TSA1) which is a database including cDNA sequence through Transcriptomic study was included in Query database, and in order to increase a usable coverage of a plant genome data, transcriptomic data on plant genomes of which sequences are determined up to date was included.

Accordingly, total 9123 sequences were searched, wherein 278 sequences were searched in Uniprot/SwissProt, 1,989 sequences were searched in Uniprot/TrEMBL, 3,953 sequences were searched in GenBank nucleotide databases, and 2,905 sequences were searched in GenBank protein databases. In order to remove the repeated sequences, sequences having 80% homology with each other clustered.

In order to confirm functional diversity among the searched terpene synthases, multiple sequence alignment (MAS) and phylogenetic tree were made by using script in a unix environment. Sequences were aligned with respect to PFAM domain (PF03936) of a protein family and phylogenetic tree was made based on the MSA using FASTTREE program.

The active site of the isoprene synthase determined based on the structure of *Populus canescens* IpsS (PDB:3n0g) was marked to the MSA. The sequences were aligned by ClustalW, and a conserved phylogenetic tree was constructed with resampling using Genious tree builder.

As the final candidates of the plant-derived sequences, *Ipomoea batatas*-derived sequence and *Elaeocarpus photiniifolius*-derived sequence were determined.

*Ipomoea batatas* sequence has the key amino acids of isoprene synthases W317 (W266 in *I. batatas*), F338 (F287 in *I. batatas*), S445 (S394 in *I. batatas*), F485 (F433 in *I. batatas*), N505 (N453 in *I. batatas*) and Y565 (Y515 in *I. batatas*)

Multiple sequence alignment of *I. batatas* isoprene synthase sequence together with the reference sequences is shown in FIG. 1a and FIG. 1b. Alignment of the substrate binding amino acid positions is shown in FIG. 2.

Among the additional new candidates, *Medicago sativa*, *Fragaria vesca* subsp. *Vesca*, *Morus notabilis*, *Populus trichocarpa*, *Dahlia pinnata*, *Sesamum indicum* and *Eucalyptus grandis* lacked an amino acid at F338 position (amino acid numbering based on *Populus alba* isoprene synthase), and *Mangifera indica*-derived sequence had an important amino acid at F338, which seemed to have a function of the isoprene synthase.

Figure 3:
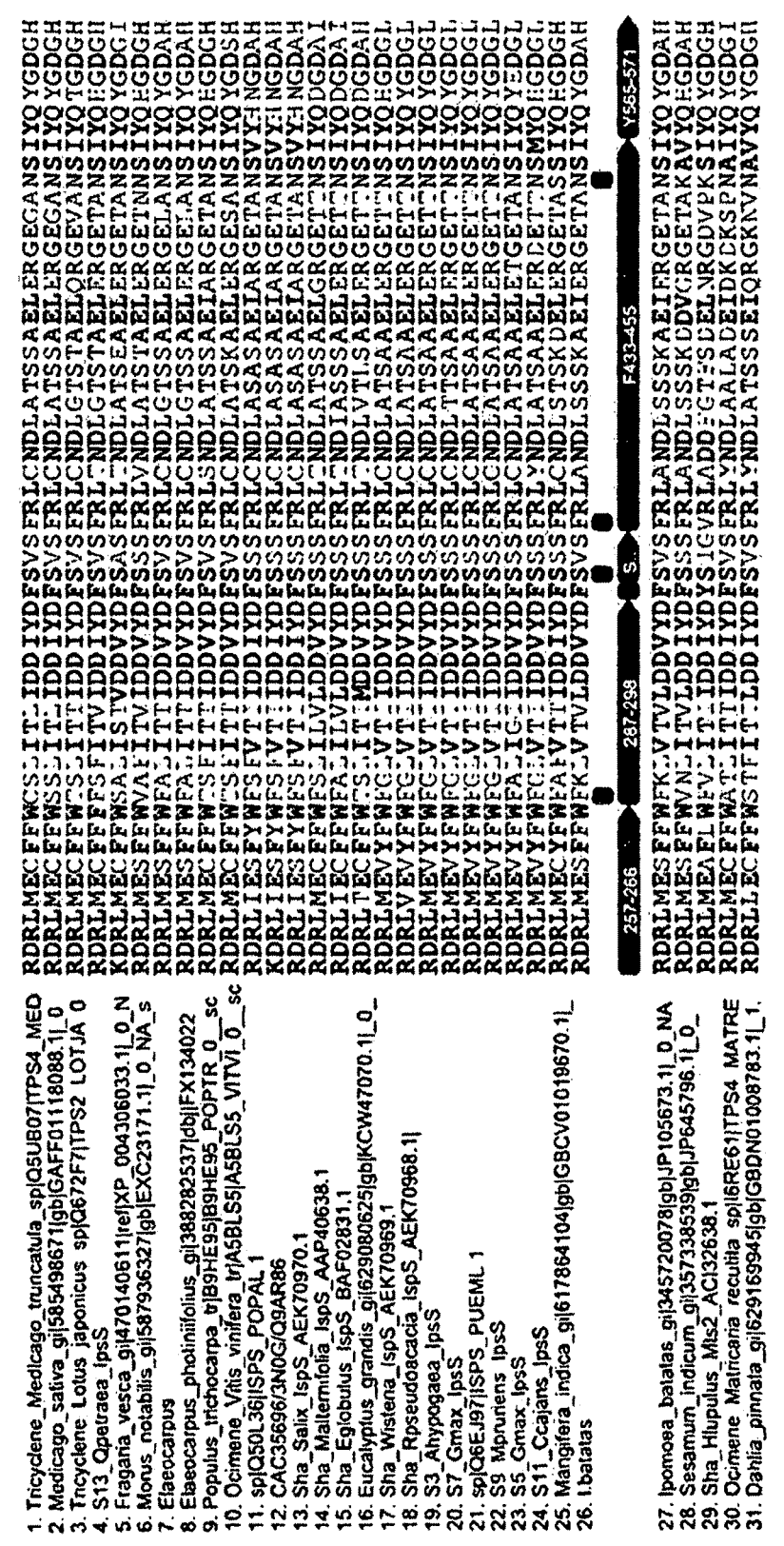

A multiple sequence alignment (MSA) result to an active site sequence of the isoprene synthase candidates was shown in FIG. 3. Reference isoprene synthase sequences, and four sequences (tricyclene or beta-ocimene synthase) other than the reference isoprene synthases were also included as a reference, and identity % of the sequences was shown in FIG. 5.

In FIG. 5, the reference isoprene synthases were shown in bold black text, and sequences similar to the reference isoprene synthase were shown in black text, and the candidates known in the related art were shown in black text in italics. Isoprene synthase candidates (*Ipomoea batatas* and *Elaeocarpus photiniifolius*) having 4 points of isoprene scores were shown in white text with black background. Additional new candidate sequences were shown in black text with grey background, and candidates having F388 and 3 points of isoprene score were shown in white text with dark grey background. Sequences with confirmed other functions are shown in grey. The phylogenetic tree was provided with EC number, the biological name, and Blast E-values, and was visualized by Geneious software (FIG. 4).

Example 2

Cloning of Selected Isoprene Synthase Gene Candidate

Since *Ipomoea batatas*- and *Elaeocarpus photiniifolius*-derived nucleotide sequences selected in Example 1 above have a low homology to the known isoprene synthase encoding nucleotide sequences, the polynucleotides were cloned to measure an enzyme activity of protein to be expressed by the polynucleotides.

The isoprene synthase polynucleotide candidates were expressed in *E. coli*, isoprene prepared in a culture medium was measured to confirm an activity of the isoprene synthase, and the known isoprene synthase genes (*P. alba*, *P. montana* and *A. hypogaea*-derived isoprene synthase genes) were expressed in *E. coli* as a control group. Since cloning and culturing using cyanobacteria require quite a long time to work, they were conducted by selecting *E. coli*.

The genes for cloning were synthesized while removing a portion of encoding N-terminal sequence (N-terminal 40 aa of *E. Pho* and 48aa of *I. bat*) from the gene. In all genes, codon optimization was performed on *Synechocystis* sp. PCC6803 (SEQ ID NO: 3), and then codon optimization was performed on *E. coli*, by using GeneScript.

The fabricated construct was cloned in pBAT4 (Peranen J. et al, *Anal. Biochem.*, 236:371-373, 1996) having trc promoter added thereto and cloned in pETDuet-1 (Novagen, USA, FIG. 6) having T7 promoter added thereto, so as to appropriate for expression in cyanobacteria, and when pBAT4 is used as a vector, the *P. alba*-derived polynucleotide and the *I. batatas*-derived polynucleotide were successfully cloned, and when pETDuet-1 is used as a vector, the *I. batatas*-, *E. photiniifolius*-, *P. alba*-, *P. Montana*- and *A. hypogaea*-derived isoprene synthase polynucleotides were cloned.

Example 3

Preparation of Isoprene in Recombinant Microorganism Containing Isoprene Synthase Gene Candidates 3-1: Transformation and Culturing Plasmids containing isoprene synthase polynucleotide candidates cloned in Example 2 above were transformed into *E. coli* BL21, and expression of isoprene synthase was confirmed.

The selected transformants and parent strains were inoculated into an LB liquid medium containing 100 μg/mL ampicillin and cultured at 30° C. (or 37° C.) overnight, then the culture medium was diluted to 1:50, cultured until the OD600 at 30° C. is 0.6 to 0.7, and treated with IPTG so as to have a final concentration of 0.5 mM, thereby inducing an enzyme expression. The culturing was performed for 24 hours using a sealed 22 mL head-space bottle while inoculating the culture medium for 2 mL/bottle. At the same time, the culturing for protein analysis was performed using Erlenmeyer flask.

3-2: Detection and Quantification of Isoprene

Isoprene prepared in *E. coli* strain cloned with isoprene synthase was analyzed by solid-phase microexrction (SPME). An isoprene standard material containing 0.002% 4-tert-butylcatechcol as a stabilizer (Fluka nr529240 CAS 78-79-5) was used, and analyzed using divinylbenzene/carboxen/PDMS (DVB/CAR/PDMS) fiber (2 cm). CTC Combi PAL system (CTC Analytics AG, Switzerland) was used as a sampler, and the combination of Agilent 7890A gas chromatograph (GC, Agilent Technologies, USA) with a5975 C mass selective detector (MSD Agilent Technologies, USA) was used. In order to separate isoprene from ethanol which is volatile occurred during the culturing, HP-5, HP-35 (30 m) and BPX5 (60 m) columns were used, and isoprene was eluted by Lipodex (50 m) and HP-Innowax (60 m).

The elution time was 20 minutes, desorption time was 8 minutes, temperature in GC oven was between 40° C. (4 mins) and 70° C. (5° C./min), and the total running time was 16.3 mins. Temperature of the injector was 250° C., MS data were collected in m/z 35 to 350, and mass spectrum of isoprene was confirmed by comparison with NIST08 library.

The basic peak was m/z 67 and the mass peak was m/z 68, and other main fragments had m/z 53, 40 and 39. Calibration curves were measured by spike of isoprene in three different media (LB, BG11 and BG11 without $Na_2CO_3$). The medium had a concentration area of 2~85 ng/2 mL, and the spike was performed on the sample with ethanol having the same amount (10 μl/bottle). The sample was put into a 22 mL head-space bottle used in both of the culturing and the analysis and was analyzed. The quantitative limit of the present invention was 0.5 ng/ml, and the detection limit was lower than the quantitative limit.

Expression in the pBAT4 constructs (trc promoter) of the P. alba- and I. batatas-derived isoprene synthase genes before and after the induction of the isoprene synthase was shown in Criterion TGX 4-20 gel with GelCode Blue dye (FIG. 7). Expression of the isoprene synthase and preparation of isoprene were confirmed by culturing five clones (A to E) of two constructs. After the induction, preparation of P. alba-derived isoprene synthase (64 kDa) was clearly confirmed, but I. batatas lysate (62 kDa) was not clearly confirmed due to high viscosity. After 24 hours of the induction, the isoprene prepared by the recombinant E. coli was analyzed by SPME method. As a result, it could be confirmed from FIG. 8 that the recombinant E. coli-derived sample containing I. batatas-derived isoprene synthase had particularly high isoprene productivity.

As a result of confirming expression of the isoprene synthase of the isoprene synthase clone of five kinds (I. batatas, E. photiniifolius, P. alba, P. montana and A. hypogaea) using pETDuet-1 vector, it could be confirmed from FIG. 9 that after 24 hours of the induction, all strains excluding E. photiniifolius showed clear isoprene synthase production.

As a result of analyzing the isoprene productivity in the five kinds of recombinant E. coli's after 24 hours of the induction, it could be confirmed from FIG. 10 that high isoprene productivity was shown in I. batatas- and P. alba-derived isoprene synthases, in particular, the highest isoprene productivity was shown in I. batatas-derived isoprene synthase, and in E. photiniifolius, an enzyme production was not confirmed in Criterion TGX 4-20 gel, but isoprene was prepared. The preparation of isoprene was not confirmed in A. hypogaea.

In addition, as a result of confirming growth of each recombinant E. coli strain with $OD_{600}$ values, it was confirmed that the growth of each strain was slightly inhibited by expression of the recombinant enzyme (FIG. 11).

Further, FIG. 12 shows time dependent isoprene productivity after expression of isoprene synthases in an E. coli strain transformed into a pETDuet-1 vector in which I. batatas of isoprene synthases and P. alba of isoprene synthases, respectably, are inserted. It could be confirmed that isoprene was accumulated steadily after expression of isoprene synthases and isoprene was also produced in an E. coli strain without inducing expression by using IPTG.

As a result of confirming time dependent growth of strain by using $OD_{600}$ value, after inducing expression by using IPTG in recombinant E. coli including IpS derived from I. batatas and recombinant E. coli including IpS derived from P. alba, growth of strain steadily decreases compared to strain without inducing treatment by using IPTG (FIG. 13).

Example 4

Synechocystis sp. Cells Expressing Isoprene Synthase

Synechocystis sp. PCC6803 is used as the parent strain and is referred to as the wild type (wt). The wt strain and transformants are maintained on BG-11 agar and in BG-11 liquid medium buffered with Hepes to pH 7.5 and is supplemented with 10 mM bicarbonate and with the antibiotics kanamycin, spectinomycin or chloramphenicol as appropriate. Instead of or in addition to bicarbonate, $CO_2$ enriched cultivation conditions are used to provide the carbon source. Synechocystis is cultivated at 30° C. under illumination (10-300 μmol photons $m^{-2}$ $s^{-1}$).

Synechocystis sp. is transformed by natural transformation using previously described methods. The presence of the transforming DNA is confirmed by PCR.

Constructs are designed for the expression of isoprene synthase in cyanobacteria. The isoprene synthase is expressed under the transcriptional control of an E. coli or a Synechocystis promoter, which allows expression of isoprene synthase in cyanobacteria. As an example, the E. coli trc or lac promoters or Synechocystis sp. psbA promoter and Synechocystis terminator or E. coli rrnB terminator or phage T7 terminator are used. The I. batatas isoprene synthase nucleotide sequence (SEQ ID: No. 2) was codon optimized for expression in Synechocystis sp. PCC6803 and synthesized by GenScript (Piscataway, N.J., USA). The expression cassettes for isoprene synthase and the antibiotic resistance marker are flanked by homologous sequences corresponding to a neutral site in the Synechocystis sp. genome to facilitate integration of the transforming DNA into the genome by homologous recombination.

Neutral sites e.g. between slr0168 and slr0338 in the Synechocystis sp. PCC6803 genome are suitable target loci for introducing the isoprene synthase. Other target sites can be chosen in order to knock out genes that potentially interfere with production of the desired product and its precursors. Genes required for biosynthesis of storage compounds such as glgA or glgC, involved in glycogen biosynthesis, are examples of such genes.

Example 5

Synechocystis sp. Cells Expressing One or More Enzymes of the Mevalonate Pathway In combination with isoprene synthase expression other genes contributing to isoprene production are introduced into Synechocystis cells. For example, the idi gene coding for isopentenyl-diphosphate delta-isomerase (EC 5.3.3.2) is introduced to enhance conversion of isopentenyl diphosphate (IPP) to dimethylallyl diphosphate (DMAPP) that is the substrate of isoprene synthase. Optionally one or more genes coding for the mevalonate pathway components, mevalonate kinase (EC2.7.1.36), phosphomevalonate kinase (EC2.7.4.2), pyrophoshomevalonate decarboxylase (EC 4.1.1.33), acetoacetyl-CoA thiolase (EC2.3.1.9), HMG-CoA synthase (EC2.3.3.10) or HMG-CoA reductase (EC1.1.1.34) are cloned under an E. coli or Synechocystis promoter that allows expression in cyanobacteria. Two or more genes are expressed as a transcriptional fusion under the control of under the transcriptional control of an E. coli or a Synechocystis promoter. Each open reading frame is preceded by a ribosome binding site (RBS) to allow independent translation of the polypeptides. The above mentioned polynucleotides and the antibiotic resistance marker are flanked by homologous sequences corresponding to the target locus of choice in the Synechocystis sp. genome to allow integration of the transforming construct into the genome.

Example 6

Synechocystis sp. Cells Over-Expressing One or More Polypeptides of the Non-Mevalonate Pathway Although cyanobacteria possess the non-mevalonate pathway for synthesising isoprenoid precursors, overexpression of selected pathway components from homologous or heterologous sources will benefit isoprene production. Constructs are designed for the overexpression of the non-mevalonate pathway genes, deoxyxylulose-5-phosphate synthase (DXP synthase; EC2.2.1.7), DXP reductoisomerase (EC1.1.1.267), MEP-cytidyltransferase (EC2.7.7.60), CPD-ME-kinase (EC2.7.1.148), MECDP synthase (1.17.7.1), HMBDP synthase (EC1.17.7.1), HMBDP reductase (EC1.17.1.2), and isopentenyl-diphosphate delta-isomerase (EC 5.3.3.2) in *Synechocystis* sp. are designed using the same principle as described for the mevalonate pathway genes. One or more non-mevalonate pathway genes are introduced into *Synechocystis* sp. in combination with isoprene synthase expression.

Example 7

Production of Isoprene by Recombinant *Synechocystis* Cells Expressing Isoprene Synthase

*Synechocystis* transformants expressing isoprene synthase and optional other genetic modifications are tested for isoprene production using an in vivo assay. Wild type cells are studied in parallel as controls. As an example, cells are grown for 4 days at 30° C. with 100 rpm shaking under continuous illumination in BG11 liquid medium supplemented with bicarbonate as the carbon source and the appropriate antibiotics. Cells from 20 ml cultivation are harvested by centrifugation and suspended in 8 ml of BG11 medium supplemented with bicarbonate and antibiotics as appropriate in 20 ml GC-MS bottles which are sealed air-tight. When isoprene synthase is expressed under control of an IPTG inducible promoter 0.5 mM IPTG is added into to medium to induce isoprene production. Cultivations are also carried out without IPTG. The bottles are incubated at 30° C. with 100 rpm shaking for up to 240 h. Samples are taken at regular intervals during the cultivation. At each time point a bottle is removed, the cultivation is heated at 40° C. and isoprene is measured from the head space of the bottle using the GC-MS method described earlier for *E. coli*.

Isoprene production into the medium in aerobic cultures of *Synechocystis* is also analysed. The culture medium is sampled periodically and the samples are transferred into GC-MS vials, heated at 40° C., and isoprene is measured off-line from the head space of the bottle using the GC-MS method described earlier for *E. coli*.

Example 8

Production of Isoprene by Recombinant *Synechocystis* Cells in a Bioreactor

The inocula for bioreactor cultivation are grown at 30° C. with 100 rpm shaking under continuous illumination in BG11 liquid medium supplemented with bicarbonate as the carbon source and the appropriate antibiotics. The inoculum is transferred into BG11 medium in a photobioreactor. Bicarbonate or $CO_2$ gas is used as the carbon source. The photobioreactor is equipped with adjustable lightning and controllable gas inlet and outlet. The cells are grown at 30° C. and the cultivation is mixed with agitation or gas bubbling. Isoprene production is analysed off-line. The culture medium is sampled periodically and the samples are transferred into GC-MS vials, heated at 40° C., and isoprene is measured from the head space of the bottle using the GC-MS method described earlier for *E. coli*. Isoprene is harvested from the bioreactor flushing the reactor periodically with $CO_2$ as described (Bentley and Melis, 2012, Biotechnol Bioeng 109:100-109).

Example 9

Construction of Isoprene Producing *Saccharomyces cerevisiae* Strains

Constructs are designed for the expression of isoprene synthase in *S. cerevisiae*. The isoprene synthase nucleotide sequence is expressed from an autonomously replicating multi-copy vector containing a 2-micron replication origin or an ARS sequence, a centromeric vector, or integrated into the genome in one or more copies. Optional other genetic modifications such as overexpression of isopentenyl-diphosphate delta-isomerase (IDI) or mevalonate pathway or non-mevalonate pathway components are also introduced into *S. cerevisiae*. The constructs can be assembled by traditional cloning methods or by recombination cloning. For example, *S. cerevisiae* strain FY834 is used for recombination cloning (Winston, Dollard and Ricupero-Hovasse, 1995). *S. cerevisiae* strain H2798 (ura-) is the parental strain which is used for the production of ispS isoprene.

A vector, named SP17, containing three *S. cerevisiae* promoter-terminator pairs cloned into the pRS426 plasmid, is used. The truncated Hmg-CoA reductase (Polakowski et al. 1998, Appl Microbiol Biotechnol. 49:66-71) is amplified by PCR using the oligonucleotides TAGCAATCTAATCTAAGTTTTAATTACAAACTC-GAGTAAAATGGACCAATTGGTGAAAACTG (SEQ ID NO: 4) and CCAAACCTCTGGCGAAGAAGTC-CAAAGCTGTCGACGGATTTAATGCAGGTGACGG (SEQ ID NO: 5) and cloned into a SP17 vector between e.g. the TEF1 promoter and ADH1 terminator by homologous recombination. The IspS nucleotide sequence of *I. batatas* (SEQ ID NO: 2) is codon optimized for expression in *S. cerevisiae* and synthesized by GenScript, amplified by PCR, and inserted between e.g. the PGK1 promoter and PGK1 terminator. The IDI nucleotide sequence is amplified by PCR and cloned between e.g. TPI1 promoter and CYC1 terminator by homologous recombination. Schematic representation of the construct is shown in FIG. 14. *S. cerevisiae* are transformed using the LiAc/PEG method (Gietz and Woods, 2002, Methods in Enzymology 350: 87-96). The resulting plasmid is transformed into *S. cerevisiae* strain and selected on synthetic complete medium lacking uracil (SCD-Ura). The presence of the transforming DNA is confirmed by PCR.

The *S. cerevisiae* IspS transformants are propagated aerobically at 30° C. with 250 rpm shaking in SC-Ura medium containing glucose, galactose or glycerol as the carbon source to produce the biomass for isoprene production. For isoprene production, aliquots of the precultures are transferred into fresh SC-Ura medium containing glucose, galactose or glycerol in tightly sealed flasks, which enable harvesting of isoprene. The bottles are incubated at 30° C. with 250 rpm shaking for up to 96 h. Samples are taken at regular intervals during the cultivation. At each time point a bottle is removed, the cultivation is heated at 40° C. and isoprene is measured from the head space of the bottle using the GC-MS method described earlier for *E. coli*.

Example 10

Construction of *Pichia kudriavzevii* Strains for Isoprene Production

Synthetic *I. batatas* IspS gene, optimized for expression in *S. cerevisiae*, was obtained from GenScript (Piscataway, N.J., USA). The IspS polynucleotide was introduced into *P. kudriavzevii* strain ATCC32196 under the PGK1 or TDH1 promoters of *P. kudriavzevii* together with the isopentenyl-diphosphate delta-isomerase (IDI) gene. The *P. kudriavzevii* PGK1 promoter and *S. cerevisiae* MEL5 terminator controlled the expression of the hygromycin resistance marker that was used for selection of transformants. The Pk promoters were amplified from the genomic DNA of *P. kudriavzevii* strain ATCC32196 essentially as described in US 2009/0226989 A1. Terminators from *S. cerevisiae* and *P. kudriavzevii* were used. The marker cassette was flanked by loxP sites to enable removal and re-use of the marker. The isoprene synthase and marker expression cassettes were flanked by homologous sequences corresponding to the *P. kudriavzevii* GPD1 locus to enable integration in the GPD1 locus. The resulting construct contained P.k. GPD1 5' flanking region-P.k. PGK1 promoter-MEL5 or hygromycin marker-MEL5 terminator-P.k. promoter-isoprene synthase nucleotide sequence-P.k. or S.c. terminator-P.k. promoter-IDI-P.k. or S.c.-P.k. GPD1 3' flanking region (FIG. 15).

A HMG-CoA reductase (Polakowski et al. 1998, Appl Microbiol Biotechnol. 49:66-71) was co-expressed with the isoprene synthase in *P. kudriavzevii* under control of the *P. kudriavzevii* promoter. The resulting construct contained P.k. PDC1 3' flanking region-P.k. promoter-MEL5 or hygromycin marker-MEL5 terminator-P.k. promoter-HMG-CoA reductase nucleotide sequence-P.k. terminator-P.k. PDC1 5' flanking region (FIG. 16).

The resulting constructs were transformed into *P. kudriavzevii* strain ATCC32196 using the LiAc/PEG method. The transformants were selected based on blue colour on yeast peptone dextrose (YPD) medium containing 5-bromo-4-chloro-3-indolyl-α-D-galactopyranoside (X-alpha-gal) or for growth on melibiose, or for growth on YPD medium containing hygromycin essentially as described in US 2009/0226989 A1. The presence of the transforming DNA was confirmed by PCR. Transformants were cultured aerobically on synthetic complete medium or yeast peptone (YP) medium containing glucose, fructose or glycerol as the carbon source. For isoprene analysis, aliquots of the precultures are transferred into fresh medium in tightly sealed GC-MS bottles retaining isoprene. The bottles were incubated at 30° C. with 100 rpm shaking for up to 96 h. Samples were taken at regular intervals during the cultivation. At each time point a bottle was removed, the cultivation was heated at 40° C. and isoprene was measured from the head space of the bottle using the GC-MS method described earlier for *E. coli* except that the medium used for the calibration curve was YP-medium containing 0.5% ethanol.

The expression vector for an N-terminally truncated *S. cerevisiae* HMG1 was named pPK-HMG (FIG. 16, SEQ ID NO: 6) and targeted for integration into the *P. kudriavzevii* PDC1 locus. The N-terminally truncated HMG1 gene (SEQ ID NO: 34) was amplified from genomic DNA of *S. cerevisiae* W303 by PCR using primers (5'-AGCGCGGATC-CATGGACCAATTGGTGAAAACTGAAG) (SEQ ID NO: 7) and (5'-AGCGCGGATCCCACATGGTGCTGTTGT-GCTTC) (SEQ ID NO: 8) and expressed under the control of the *P. kudriavzevii* PGK1 promoter and *S. cerevisiae* ADH1 terminator. The expression construct with the MEL5 marker and *P. kudriavzevii* PDC1 homology regions was released with NotI from plasmid pPK-HMG and transformed into *P. kudriavzevii* VTT-C-79090T (ATCC32196) using the lithium acetate method and colonies were screened based on blue colour on YPD-agar containing 40 µg/ml 5-bromo-4-chloro-3-indolyl-α-D-galactopyranoside. A transformant Pk/HMG1 was selected for continuation.

The vector for expression of *I. batatas* IspS and *S. cerevisiae* IDI1 was named pPK-IspS-IDI (FIG. 15; SEQ ID NO: 9). The integration was targeted to the *P. kudriavzevii* GPD1 locus. The *P. kudriavzevii* GPD1 homology regions were amplified by PCR from genomic DNA of *P. kudriavzevii* VTT-C-79090T (ATCC32196). The *I. batatas* IspS gene with a C-terminal StrepII-tag was codon optimized for expression in *S. cerevisiae* and synthesized by Genscript (Hongkong) (SEQ ID NO: 33). *I. batatas* IspS was expressed under control of the *P. kudriavzevii* PGK1 promoter and *S. cerevisiae* ADH1 terminator. The IDI1 gene (SEQ ID NO: 35) was amplified by PCR from genomic *S. cerevisiae* DNA using primers 918IDISc-F (5'-CTTTTTA-CAACAAATATAAAACCAAAAGCGGCCGCTTAAT-TAAAAAATGACTGCCGACAACAATAGTATG) (SEQ ID NO: 10) and C031_919new_IDISc_R (5'-AGAGA-CATGGGAGATCCCGCGGGCGGCCGCTTAATTAAT-TATAGCATTCTATGAATTTGCC) (SEQ ID NO:11), and placed under the control of the *P. kudriavzevii* TDH1 promoter and *S. cerevisiae* PGK1 terminator. The expression construct with a hygromycin resistance marker and *P. kudriavzevii* GPD1 homology regions was released with NotI from plasmid pPK-IspS-IDI and transformed into *P. kudriavzevii* VTT-C-79090T (ATCC32196) and into *P. kudriavzevii* Pk/HMG1 using the lithium acetate method (Gietz et al. 1992, Nucleic Acids Res 20:1425-1425) and colonies were selected on YPD-agar containing 450 µg/ml hygromycin B as the selective agent. Transformed colonies Pk/IspS+IDI1-69, Pk/IspS+IDI1-72, Pk/ISpS+IDI1-74 and Pk/IspS+IDI1+HMG1-79 were isolated and tested for isoprene production.

*P. kudriavzevii* VTT-C-79090T (ATCC32196) and the Pk/HMG1, Pk/IspS+IDI1 and Pk/IspS+IDI1+HMG1 transformants were grown in YPD medium o/n at 30° C. Cells were collected by centrifugation and suspended in YP-1% glucose or YP+1% glycerol to an $OD_{600}$=3.2 ml aliquots were sealed in 22 ml headspace bottles and incubated o/n at 30 with 100 rpm shaking. Isoprene production was measured as described above except that the isoprene standards were prepared in YP-medium containing 0.5% ethanol. Isoprene concentrations measured are shown in FIG. 18. FIG. 18. shows isoprene production by *P. kudriavzevii* transformants in YP medium containing 1% glucose (grey) or 1% glycerol (black) as the carbon source. All transformants expressing IspS and IDI1 produced isoprene while the parent strain and the strain expressing only HMG1 did not produce detectable isoprene. The amount of isoprene measured ranged from 1 to 12 µg in the 2 ml samples depending on the strain and cultivation conditions. More isoprene was produced on YP-glycerol medium than on YP-glucose medium. The presence of HMG1 in addition to IspS and IDI1 increased isoprene production approximately 3-fold in YP-glycerol medium and 2-fold in YP-glucose medium.

Example 11

Construction of *Trichoderma reesei* Strains Overexpressing an Isoprene Synthase for Isoprene Production I Synthetic *I. batatas* IspS gene, optimized for expression in *T. reesei*, is obtained from GenScript (Piscataway, N.J., USA) (SEQ ID NO: 36). The codon optimized IspS polynucleotide was introduced into *T. reesei* strain Rut-30 under the control of gpdA promoter of *Aspergillus nidulans* or under the control of the cbh1 promoter of *T. reesei*.

The resulting constructs contained the *T. reesei* cbh1 5' flank region-cbh1 promoter-isoprene synthase-nucleotide sequence *A. nidulans* gpdA promoter hygromycin resistance marker (hph) and *A. nidulans* trpC terminator-*T. reesei* cbh1 terminator and 3' flank region. The resulting constructs were transformed into *T. reesei* using the PEG-mediated protoplast transformation. The transformants were selected based on hygromycin resistance. Instead of hph, the acetamidase *A. nidulans* amdS gene can be used as the selective marker and the transformants were selected based on the ability to use acetamide as the sole nitrogen source. Alternatively, the isoprene synthase was expressed under the *A. nidulans* gpdA promoter. The codon optimized isoprene synthase polynucleotide was cloned into an expression vector containing the *A. nidulans* gpdA promoter-isoprene synthase-nucleotide sequence-*A. nidulans* trpC terminator-*A. nidulans* gpdA promoter hygromycin resistance marker (hph) and *A. nidulans* trpC terminator. Schematic view of the plasmid used for transformation was shown in FIG. 16. The transformants were purified from colonies originating from single spores, and the integration of the expression cassette into the genome was confirmed by PCR amplification of the expression cassette. The polynucleotides were integrated into the cbh1 locus or into a non-homologous site in *T. reesei* genome.

*T. reesei* transformants containing the ispS polynucleotide were cultivated in shake flasks in medium containing 7.6 g/L $(NH_4)_2SO_4$ 15.0 g/L $KH_2PO_4$, 2.4 mM $MgSO_4.7H_2O$, 4.1 mM $CaCl_2.H_2O$, 3.7 mg/L $CoCl_2$, 5 mg/L $FeSO_4.7H_2O$, 1.4 mg/L $ZnSO_4.7H_2O$, 1.6 mg/L $MnSO_4.7H_2O$, and a 10 g/L carbon source or a mixture of carbon sources selected from cellulose, xylan, glucose, lactose, glycerol, galactose, sorbose, sorbitol, xylose, arabinose or 0.7 mM sophorose. The pH of the medium was adjusted to 4.8 by addition of KOH. The cultures were inoculated with $8 \times 10^7$ spores/200 ml medium and grown for up to 7 days in conical flasks at 28° C. with shaking at 250 rpm. The culture medium was sampled periodically and the samples were transferred into GC-MS vials, heated at 40° C., and isoprene was measured off-line from the head space of the bottle using the GC-MS method described earlier for *E. coli*.

Alternatively, the aliquots of the culture transferred into fresh medium in tightly sealed bottles. The bottles were incubated at 28° C. with 250 rpm shaking for up to 96 h. Samples were taken at regular intervals during the cultivation. At each time point a bottle was removed, the cultivation was heated at 40° C. and isoprene was measured from the head space of the bottle using the GC-MS method described earlier for *E. coli*.

Example 12

Construction of *Trichoderma reesei* Strains Overexpressing an Isoprene Synthase for Isoprene Production II Strains

*Escherichia coli* DH5α (Life Technologies) was used for propagation of the plasmids. *Trichoderma reesei* QM6a (VTT-D-071262T, ATCC13631), RutC-30 (VTT-D-086271, ATCC56765), and M122 (RutC-30 mus53Δ) were obtained from VTT Culture Collection (Espoo, Finland). Spore suspensions were prepared by cultivating the fungus on potato-dextrose plates (BD, Sparks, Md., USA) for 5-7 days, after which the spores were harvested, suspended in a buffer containing 0.8% NaCl, 0.025% Tween-20 and 20% glycerol, filtered through cotton and stored at −80° C.

Expression Vector

The vector for expression of *I. batatas* IspS in *T. reesei* was named pCIL-105 (FIG. 19 SEQ ID NO:12). The backbone for the expression vector contained 5' and 3' flank regions (<1000 bp) of the *T. reesei* pep4 (tre77579) gene in pRS426 (ATCC77107) vector background. The primer sequences indicating the start and end regions for both pep4 flanks are shown in Table 1. The selection marker (pyr4) in the vector backbone pCIL102 was removed by NotI digestion and replaced by hygromycin resistance cassette obtained from plasmid pCIL-107 by NotI digestion. The gene encoding *I. batatas* isoprene synthase with a C-terminal StrepII-tag was obtained from *E. coli* expression plasmid pCIL41 by NdeI-AvrII digestion. The *Aspergillus nidulans* gpdA promoter, *A. nidulans* trpC terminator and a bridge fragment (part of pep4 3'flank) were produced by PCR using primers in Table 1 and plasmid pCIL104 containing these elements as templates. PCR amplification was carried out with KAPA HiFi HotStart ReadyMix PCR kit (KAPA Biosystems). All fragments were separated with agarose gel electrophoresis and isolated with a gel extraction kit (Qiagen). The PCR fragments contained 30 bp or 40 bp overlapping sequences needed for cloning the expression construct using homologous recombination system in yeast. The vector backbone and the appropriate digestion and PCR fragments were transformed into *S. cerevisiae* (strain H3488/FY834) according to Gietz, R. D., and Woods, R. A. (2002, Guide to Yeast Genetics and Molecular and Cell Biology, Pt B 350, pp. 87-96). The plasmid DNA from the yeast transformants was rescued by transformation into *E. coli* and checked from a few clones by digestion. The clone taken further was verified by sequencing and named pCIL105 (SEQ ID NO: 12).

Strain Generation

For *T. reesei* transformation, the expression construct was released from pCIL105 with MssI and the correct fragment was purified from agarose gel using QIAquick Gel Extraction Kit (Qiagen). *T. reesei* strain RutC-30 or *T. reesei* strain M122 (RutC-30 Δmus53) was transformed with 5 μg of expression cassette fragment according to Penttila et al. 1987 (Gene 61: 155-164). Transformants were selected on *Trichoderma* minimal medium containing 125 μg/ml hygromycin B (Calbiochem). The transformants were streaked onto *Trichoderma* minimal medium agar with 0.1% (v/v) Triton X-100 and 150 μg/ml Hygromycin B and cultivated at +28° C. Transformants growing on selective plates were screened by PCR for correct 5' and 3'integration or for the presence of the IspS expression cassette (FIG. 20) somewhere else in the genome using the primers shown in Table 2. FIG. 20. shows PCR analysis for the presence of the IspS expression cassette in *T. reesei* transformed with pCIL105. Wild type strain QM6a, parent and DDIW are negative controls. For PCR, internal primers (SEQ ID NO: 31 and SEQ ID: NO 32) shown in Table 2 were used. The expected product size was approximately 1.1 kb.

TABLE 1

Primers used to generate fragments for cloning the expression vector pCIL105 for *I. batatas* IspS-C-StrepII.

| Primer | Sequence | Product |
| --- | --- | --- |
| 77579_5f | TCAGGTCAACCACCGAGGAC (SEQ ID NO: 13) | pep4 5'flank |
| 77579_5r | TGAATGGGATGGTTCGATTG (SEQ ID NO: 14) | |

TABLE 1-continued

Primers used to generate fragments for cloning the expression vector pCIL105 for *I. batatas* IspS-C-StrepII.

| Primer | Sequence | Product |
|---|---|---|
| 77579_3f | AGGTAGACGCTTTGCGAGTG (SEQ ID NO: 15) | pep4 3'flank |
| 77579_3r | TGAACTGACGCGGACTGA (SEQ ID NO: 16) | |
| C017_gpdA_rec_for | CCTCTGGCAGCAATCGAACCATCCCATTCATTAATTAA GCTCCTTATTGAAGTCGGAGG (SEQ ID NO: 17) | gdpA prom |
| C018_gpdA_rec_rev | ATGAGGAGGGTTGATAGTTTGCTGAGCGGCGGGCAGT CATGATGTCTGCTCAAGCGGG (SEQ ID NO: 18) | |
| C019_trpC_rec_for | TAATCCAGTGGAATCTGTCCCACCCACAATTTGAAAAG TAAGATCCACTTAACGTTACTGAAATCA (SEQ ID NO: 19) | trpC term |
| C020_trpC_rec_rev | AAGGGGACCGGCCGCTAGTCTCACCGTTATGCGGCCG CTTAATTAAGAGTGGAGATGTGGAGTGGG (SEQ ID NO: 20) | |
| C021_pep4_3frec_for | GATAACCCATCGGCAGCAGATGATAATGATTCCGCAG CACGCGGCCGCAGGTAGACGCTT (SEQ ID NO: 21) | pep4 bridge |
| C022_pep4_3f_rev | GAGGTGCCAAAGCCGTTTCG (SEQ ID NO: 22) | |

TABLE 2

Primers used to screen for correct integration of the expression cassette or the presence of the IspS cassette in the *T. reesei* genome.

| Primer | Sequence | Product |
|---|---|---|
| T302_77579_5int | GATTCATCACAGGGGCAGTC (SEQ ID NO: 23) | 5'integration |
| T624_gpdA_seqR1 | CTCCATATTCTCCGATGATGC (SEQ ID NO: 24) | |
| T302_77579_5int | GATTCATCACAGGGGCAGTC (SEQ ID NO: 25) | 5'integration |
| C046_gpdA_rev | TATCCTCTTGACACCGCTCC (SEQ ID NO: 26) | |
| T415_77579_3screen | ACGCCGTTGCTGAGCCTTG (SEQ ID NO: 27) | 3'integration |
| T1411_cbh2t_end_f | CCAATAGCCCGGTGATAGTC (SEQ ID NO: 28) | |
| T415_77579_3screen | ACGCCGTTGCTGAGCCTTG (SEQ ID NO: 29) | 3'integration |
| T1404_cbh2term_for | CCGTCTAGCGCTGTTGATTG (SEQ ID NO: 30) | |
| C009_Ibat_for1 | GATCAACTTAGCACGCATTG (SEQ ID NO: 31) | internal |
| C029_PKIp_rev | TTTGCTCCAACTCAGGCG (SEQ ID NO: 32) | |

Example 13

Construction of *Aspergillus niger* Strains Overexpressing an Isoprene Synthase for Isoprene Production The codon optimized isoprene synthase polynucleotide of example 3 was cloned into an expression vector containing the *A. nidulans* gpdA promoter-isoprene synthase polynucleotide-*A. nidulans* trpC terminator-*A. nidulans* gpdA promoter hygromycin resistance marker (hph) and *A. nidulans* trpC terminator (FIG. 17). The resulting construct was transformed into *A. niger*. Transformation was performed using the PEG-mediated protoplast transformation. The transformants were selected based on hygromycin resistance. The presence of the transforming DNA was confirmed by PCR.

*A. niger* was grown in the production medium (The defined medium of Vogel described by Mojzita et al., 2010, with 20 g/L glucose or xylose as a carbon source). Pre-cultures were grown in the medium containing 10 g/L yeast extract, 20 g/L peptone and 30 g/L gelatine (50 ml medium in 250 ml flasks). Mycelium from 50 ml cultures was collected by filtration, washed with sterile $H_2O$ and re-suspended in 20 ml of the production medium in 250 ml flasks. Cultures were incubated at 30° C., 250 rpm. The culture medium was sampled periodically and the samples were transferred into GC-MS vials, heated at 40° C., and isoprene was measured off-line from the head space of the bottle using the GC-MS method described earlier for *E. coli*. Alternatively, for isoprene production, aliquots of the culture were transferred into fresh medium in tightly sealed GC-MS bottles. The bottles were incubated at 30° C. with 250 rpm shaking for up to 96 h. Samples were taken at regular intervals during the cultivation. At each time point a bottle was removed, the cultivation was heated at 40° C. and isoprene was measured from the head space of the bottle using the GC-MS method described earlier for *E. coli*.

Example 14

*Ipomoea batatas* IspS Expression in Plant Cell Cultures

The *I. batatas* isoprene synthase polynucleotide was cloned into an over expression vector functional in various plant species under the control of the CaMV35S promoter for expression in plant cells. The expression vector had the hygromycin or kanamycin resistance marker for the selection of transformants. *Nicotiana tabacum* bright yellow (BY-2) cell suspension cultures or hairy root cultures were maintained and transformed with the isoprene synthase expression construct essentially as described in (Hakkinen et al. 2007 Phytochemistry 68:2773-2785). Transformants were selected based on antibiotic resistance. The presence of the transforming DNA was confirmed by PCR. For isoprene accumulation analysis, hairy roots were incubated in 20 ml medium in 100 ml shake flasks and cultivated in a rotary shaker (70 rpm, 24° C.) in modified Gamborg B5 medium without casein (Jouhikainen et al., Planta, 208:545-551, 1999) for up to 28 days. The culture medium was sampled periodically and the samples were transferred into GC-MS vials, heated at 40° C., and isoprene was measured off-line from the head space of the bottle using the GC-MS method described earlier for *E. coli*.

Although specific embodiments of the present invention are described in detail, it will be apparent to those skilled in the art that the specific description is merely desirable exemplary embodiment and should not be construed as limiting the scope of the present invention. Therefore, the substantial scope of the present invention is defined by the accompanying claims and equivalent thereof.

Sequence Listing Free Text

Attach the electronic file.

The invention claimed is:

1. A recombinant vector comprising a codon-optimized polynucleotide encoding an isoprene synthase operably introduced therein, wherein the codon-optimized polynucleotide has a nucleotide sequence having at least 90% sequence identity to SEQ ID NO: 3 or SEQ ID NO: 33.

2. The recombinant vector of claim 1, wherein the recombinant vector comprises a promoter for expressing said polynucleotide.

3. The recombinant vector of claim 2, wherein the promoter is selected from the group consisting of psbA2, trc, rbcL, petJ, psaA, psaB, tac, cpcB, petC and lac for expressing in cyanobacteria, wherein the promoter is selected from the group consisting of PGK1, TPI1, TDH, PDC1, FBA1, ENO1, ENO2, PYK1, ADH1, and TEF1 for expressing in yeast, wherein the promoter is selected from the group consisting of cbhl, gpdA, glaA, pdc and exlA for expressing in filamentous fungi, or wherein the promoter is CMV35S for expressing in plant cells.

4. The recombinant vector of claim 1, wherein the codon-optimized polynucleotide has the nucleotide sequence of SEQ ID NO: 3.

5. The recombinant vector of claim 1, wherein the codon-optimized polynucleotide has the nucleotide sequence of SEQ ID NO: 33.

6. A recombinant host cell comprising a recombinant vector comprising a codon-optimized polynucleotide encoding an isoprene synthase operably introduced therein, wherein the codon-optimized polynucleotide has a nucleotide sequence having at least 90% sequence identity to SEQ ID NO: 3 or SEQ ID NO: 33.

7. The recombinant host cell of claim 6, wherein the host cell is selected from the group consisting of cyanobacteria, yeast, filamentous fungi and plant cell.

8. The recombinant host cell of claim 7, wherein the cyanobacterium is unicellular cyanobacterium or multicellular cyanobacterium.

9. The recombinant host cell of claim 8, wherein the unicellular cyanobacterium is *Synechocystis* sp. or *Synechococcus* sp.

10. The recombinant host cell of claim 8, wherein the multicellular cyanobacterium is *Gloeocapsa* sp. or filamentous cyanobacterium sp.

11. The recombinant host cell of claim 10, wherein the filamentous cyanobacterium is selected from the group consisting of *Nostoc* sp., Anabaena sp., and *Arthrospira* sp.

12. The recombinant host cell of claim 7, wherein the yeast is selected from the group consisting of *Saccharomyces* sp., *Pichia* sp., Candida sp., *Kazachstania* sp., *Kluyveromyces* sp., *Hansenula* sp., *Rhodosporidium* sp., *Cryptococcus* sp., and *Yarrowia* sp.

13. The recombinant host cell of claim 7, wherein the filamentous fungus is selected from the group consisting of *Trichoderma* sp., *Mucor* sp., *Mortierella* sp., *Neurospora* sp., and *Aspergillus* sp.

14. The recombinant host cell of claim 7, wherein the plant cell is selected from the group consisting of *Nicotiana* sp., *Catharantus* sp., and *Hyoscyamus* sp.

15. The recombinant host cell of claim 6, further comprising one or more genes, which are introduced thereto, selected from the group of:
   (i) genes coding for the mevalonate pathway components, selected from the group of gene coding for mevalonate kinase (EC2.7.1.36), *phosphomevalonate* kinase (EC2.7.4.2), *pyrophoshomevalonate* decarboxylase (EC 4.1.1.33), acetoacetyl-CoA thiolase (EC2.3.1.9), HMG-CoA synthase (EC2.3.3.10), and HMG-CoA reductase (EC1.1.1.34); and
   (ii) genes coding for isopentenyl-diphosphate delta-isomerase (EC 5.3.3.2).

16. The recombinant host cell of claim 6, further comprising a gene which is introduced thereto, wherein the gene is an idi gene coding for isopentenyl-diphosphate delta-isomerase (EC 5.3.3.2) and/or a gene coding for HMG-CoA reductase (EC1.1.1.34).

17. A method for preparing isoprene comprising:
   (a) culturing the recombinant host cell of claim 6, thereby producing isoprene; and
   (b) recovering the isoprene.

18. The method of claim 17, wherein the culturing of step (a) is performed on a medium comprising a carbon source selected from the group consisting of $CO_2$, bicarbonate, glucose, glycerol, glycerin, dihydroxyacetone, yeast extract, biomass, molasses, sucrose, galactose, sorbose, sorbitol, xylose, arabinose, cellulose, xylan, lactose and oil.

* * * * *

```
                         SEQUENCE LISTING

<160> NUMBER OF SEQ ID NOS: 96

<210> SEQ ID NO 1
<211> LENGTH: 588
<212> TYPE: PRT
<213> ORGANISM: Ipomoea batatas

<400> SEQUENCE: 1

Pro Asn Phe Gly Cys Tyr Leu Ile His Asn Asn Leu Pro Asn Pro Lys
1               5                   10                  15

Asp Ala Lys Pro Leu Thr Leu Leu Leu Asn Arg Asn Ser Gly Val Ser
            20                  25                  30

Cys Pro Arg Gln Leu Arg Cys Leu Ala Ser Ser Ala Gln Asn Gln Glu
        35                  40                  45

Thr Ala Arg Arg Ser Ala Asn Tyr Gln Pro Ser Ser Trp Ser Tyr Asp
    50                  55                  60

Glu Tyr Leu Val Asp Thr Thr Asn Asp Ser Lys Leu Arg Ile Gln
65                  70                  75                  80

Glu Asp Ala Arg Lys Lys Leu Glu Glu Val Arg Asn Val Leu Glu
                85                  90                  95

Asp Gly Lys Leu Glu Thr Leu Ala Leu Leu Glu Leu Ile Asp Asp Ile
            100                 105                 110

Gln Arg Leu Gly Leu Gly Tyr Lys Phe Arg Glu Ser Thr Ser Thr Ser
        115                 120                 125

Leu Ala Met Leu Lys Met Ser Val Gly Gln Glu Ala Ser Asn Ser Ser
    130                 135                 140

Leu His Ser Cys Ser Leu Tyr Phe Arg Leu Leu Arg Glu His Gly Phe
145                 150                 155                 160

Asp Ile Thr Pro Asp Val Phe Glu Lys Phe Lys Asp Glu Asn Gly Lys
                165                 170                 175

Phe Lys Asp Ser Ile Ala Lys Asp Val Arg Gly Leu Leu Ser Leu Tyr
            180                 185                 190

Glu Ala Ser Phe Leu Gly Phe Glu Gly Glu Asn Ile Leu Asp Glu Ala
        195                 200                 205

Arg Glu Phe Thr Thr Met His Leu Asn Asn Ile Lys Asp Lys Val Asn
    210                 215                 220

Pro Arg Ile Ala Glu Glu Val Asn His Ala Leu Glu Leu Pro Leu His
225                 230                 235                 240

Arg Arg Val Glu Arg Leu Glu Ala Arg Arg Ile Gln Ser Tyr Ser
                245                 250                 255

Lys Ser Gly Glu Thr Asn Gln Ala Leu Leu Thr Leu Ala Lys Ile Asp
            260                 265                 270

Phe Asn Thr Val Gln Ala Val Tyr Gln Arg Asp Leu Gln Asp Val Ser
        275                 280                 285
```

```
Lys Trp Trp Lys Asp Thr Ala Leu Ala Asp Lys Leu Ser Phe Ala Arg
    290                 295                 300
Asp Arg Leu Met Glu Ser Phe Phe Trp Ala Ile Gly Met Ser Tyr Asp
305                 310                 315                 320
Pro Gln His Ser Lys Ser Arg Glu Ala Val Thr Lys Thr Phe Lys Leu
                325                 330                 335
Val Thr Val Leu Asp Asp Val Tyr Asp Val Tyr Gly Ser Leu Asp Glu
            340                 345                 350
Leu Glu Lys Phe Thr Ala Ala Ala Glu Arg Trp Asp Val Asp Ala Ile
        355                 360                 365
Lys Asp Leu Pro Asp Tyr Met Lys Leu Cys Tyr Leu Ser Leu Phe Asn
370                 375                 380
Thr Val Asn Asp Leu Ala Tyr Asp Thr Leu Lys Asp Lys Gly Glu Thr
385                 390                 395                 400
Val Ile Pro Ile Met Lys Ala Trp Ala Asp Leu Leu Lys Ala Phe
                405                 410                 415
Leu Gln Glu Ala Gln Trp Ile Tyr Asn Lys Tyr Thr Pro Thr Phe Asp
            420                 425                 430
Glu Tyr Leu Asn Asn Ala Arg Phe Ser Val Ser Gly Cys Val Met Leu
        435                 440                 445
Val His Ser Tyr Phe Thr Thr Gln Asn Ile Thr Lys Glu Ala Ile His
    450                 455                 460
Ser Leu Glu Asn Tyr His Asp Leu Leu Ile Trp Pro Ser Ile Val Phe
465                 470                 475                 480
Arg Leu Ala Asn Asp Leu Ser Ser Ser Lys Ala Glu Ile Glu Arg Gly
                485                 490                 495
Glu Thr Ala Asn Ser Ile Thr Cys Tyr Met Asn Glu Thr Gly Gln Ser
            500                 505                 510
Glu Glu Gln Ala Arg Glu His Ile Ser Lys Leu Ile Asp Glu Cys Phe
        515                 520                 525
Lys Lys Met Asn Lys Glu Met Leu Ala Thr Ser Thr Ser Pro Phe Glu
530                 535                 540
Lys Ser Phe Ile Glu Thr Ala Ile Asn Leu Ala Arg Ile Ala Leu Cys
545                 550                 555                 560
Gln Tyr Gln Tyr Gly Asp Ala His Ser Asp Pro Asp Val Arg Ala Arg
                565                 570                 575
Asn Arg Ile Val Ser Val Ile Ile Asn Pro Val Glu
            580                 585

<210> SEQ ID NO 2
<211> LENGTH: 1767
<212> TYPE: DNA
<213> ORGANISM: Ipomoea batatas

<400> SEQUENCE: 2
ccaaacttcg gttgctactt aattcacaac aatctcccta accctaaaga tgctaagcca      60
ctaacattac tccttaaccg taacagtggt gttagctgcc cacgacaact tcgatgtctt     120
gctagcagtg cacagaatca agaaactgcc agacgttccg ccaattacca acctagttct     180
tggagttacg atgaatattt ggtggacact acaaccaatg actcaaagtt gagaatacaa     240
gaggatgcta gaaagaagtt ggaggaagaa gtgagaaacg tccttgagga tgggaaattg     300
gaaacgttag cctgcttga gctaattgac gatattcaac gtttagggtt gggttacaaa     360
ttcagagaaa gtactagtac atcccttgct atgctaaaga tgtctgttgg acaagaagcc     420
```

| | |
|---|---:|
| tcaaactcta gcctccattc ttgttctctc tattttagat tattaagaga gcatggcttt | 480 |
| gacattactc cagatgtttt tgaaaaattc aaggatgaaa atgggaaatt caaggacagc | 540 |
| atagctaaag acgttcgtgg gttgttgagt ttgtacgagg cttcctttct gggatttgaa | 600 |
| ggggagaaca tcttagacga ggcaagagaa ttcacaacta tgcatctaaa caacattaag | 660 |
| gataaggtta atccaagaat tgcagaagaa gtgaaccacg cattggagct tccacttcac | 720 |
| cgaagagtgg agaggctaga ggccaggcgt agaatccaat cctactccaa atcgggagag | 780 |
| acaaatcaag cgttattaac actagcaaag atcgatttca acactgttca agccgtgtat | 840 |
| caaagagatc tacaagatgt ttcaaagtgg tggaaagata ccgcgttagc agataagttg | 900 |
| agctttgcta gggacaggct aatggagagc ttcttttggg caattggaat gtcttatgat | 960 |
| cctcaacata gtaaaagtcg agaagcggtg acaaaaacat tcaagcttgt cacggtcctt | 1020 |
| gatgatgttt acgatgtgta tggctctctc gatgaacttg agaaattcac tgctgctgct | 1080 |
| gaaagatggg atgttgatgc aataaaagac cttccagact acatgaagtt gtgctatctt | 1140 |
| tctcttttca acactgtcaa cgacttagca tatgataccT aaaggacaa aggagaaact | 1200 |
| gtcattccta tcatgaagaa agcgtgggca gatttattga agcattctt gcaagaagca | 1260 |
| caatggatct acaacaaata cactcctacc tttgatgaat acctcaacaa tgcacgtttt | 1320 |
| tctgtgtctg ttgtgtcat gttagttcac tcctacttca ccactcagaa catcacaaag | 1380 |
| gaagcaattc attccttgga gaactaccat gatcttttaa tctggccgtc catagttttc | 1440 |
| cgccttgcta acgatttgag ctcttctaag gcggagatag agagaggaga aacagcaaac | 1500 |
| tcgattacat gctatatgaa tgagactgga cagtcggagg agcaagctcg ggaacacatt | 1560 |
| agtaaactaa ttgacgagtg ctttaagaag atgaacaaag agatgctagc tacttcaact | 1620 |
| tcaccatttg agaaatcctt catagagact gcaataaatc ttgctcgaat tgctctgtgc | 1680 |
| caatatcagt atggtgacgc tcacagtgac cctgatgtta gagcaagaaa tcggatcgtg | 1740 |
| tcagttatca taaatccggt tgaataa | 1767 |

<210> SEQ ID NO 3
<211> LENGTH: 1626
<212> TYPE: DNA
<213> ORGANISM: Artificial
<220> FEATURE:
<223> OTHER INFORMATION: optimized sequence of IspS

<400> SEQUENCE: 3

| | |
|---|---:|
| atgactgccc gccgctcagc aaactatcaa ccctcctcat ggtcttacga cgaatacttg | 60 |
| gtggacacta ctactaacga cagcaaactg cgcattcaag aagacgctcg taaaaaattg | 120 |
| gaagaagaag tgcgtaacgt tctggaagat ggcaaattgg aaaccttagc actgttggaa | 180 |
| ctgattgatg acatccaacg gctgggcttg ggttataaat ttcgcgaaag caccagtact | 240 |
| tccctggcta tgttgaaaat gagtgtgggg caggaagcat ccaacagcag tttgcattct | 300 |
| tgttcattgt actttcgttt actgcgggaa cacggcttcg atattacccc cgacgtgttc | 360 |
| gaaaaattca agatgaaaaa cggtaaattt aaagatagca tcgctaaaga tgttcgcggg | 420 |
| ttgttatcat tgtatgaagc aagctttta gggttcgaag cgaaaacat tttggacgaa | 480 |
| gcccgcgaat tcaccactat gcatctgaat aacatcaaag ataaagtgaa tccccgtatc | 540 |
| gcggaagaag ttaaccatgc tttagaactg ccgttgcacc gccgtgtgga acgtctggaa | 600 |
| gctcggcgcc gtattcaaag ctatagtaaa tccggtgaaa ccaatcaggc cctgctgacc | 660 |
| ctggctaaaa tcgattttaa caccgtgcag gcggtttacc aacgggatct gcaggacgtt | 720 |

```
agtaaatggt ggaaagacac tgcattggcc gataaattat ccttcgcccg ggatcgcctg    780
atggaaagct ttttctgggc gattggtatg agctatgatc cccaacactc taaatcacgg    840
gaagccgtga ccaaaacttt taaactggtg accgttttgg atgacgtgta tgacgtttac    900
gggtctttag atgaactgga aaaattcacc gccgccgccg aacgttggga tgttgacgcg    960
attaaagatc tgccggacta catgaaattg tgttacttat ccctgtttaa taccgtgaac   1020
gatctggctt atgacacctt gaaagataaa ggcgaaactg ttattcctat catgaagaaa   1080
gcctgggctg atttactgaa agcatttctg caggaagccc aatggatcta caacaaatac   1140
accccaactt cgatgaata cctgaataac gcccgtttca gcgtgagtgg ttgcgtgatg   1200
ttggttcata gctactttac cactcagaac atcaccaaag aagcgatcca ttctctggaa   1260
aactaccacg acttgttaat ttggcctagc atcgttttcc gtttagcaaa tgatctgtcc   1320
tcttcaaaag ccgaaattga acggggcgaa accgcgaata gcatcacttg ttatatgaac   1380
gaaaccggtc aaagtgaaga acaggcccgt gaacacattt ccaaactgat cgatgaatgc   1440
ttcaagaaaa tgaacaaaga aatgctggcc acctccactt ctccgtttga aaaatccttc   1500
attgaaaccg cgatcaactt agcacgcatt gccctgtgcc agtatcaata cggcgatgcc   1560
catagcgatc cagatgttcg ggcacgcaac cgcattgtgt cagttatcat taatccagtg   1620
gaatag                                                             1626

<210> SEQ ID NO 4
<211> LENGTH: 62
<212> TYPE: DNA
<213> ORGANISM: Artificial
<220> FEATURE:
<223> OTHER INFORMATION: primer

<400> SEQUENCE: 4
tagcaatcta atctaagttt taattacaaa ctcgagtaaa atggaccaat tggtgaaaac    60
tg                                                                   62

<210> SEQ ID NO 5
<211> LENGTH: 53
<212> TYPE: DNA
<213> ORGANISM: Artificial
<220> FEATURE:
<223> OTHER INFORMATION: primer

<400> SEQUENCE: 5
ccaaacctct ggcgaagaag tccaaagctg tcgacggatt taatgcaggt gac          53

<210> SEQ ID NO 6
<211> LENGTH: 9167
<212> TYPE: DNA
<213> ORGANISM: Artificial
<220> FEATURE:
<223> OTHER INFORMATION: expression vector for an N-terminally truncated
      S. cerevisiae HMG1 named pPK-HMG
<220> FEATURE:
<221> NAME/KEY: misc_feature
<222> LOCATION: (1189)..(1189)
<223> OTHER INFORMATION: n is a, c, g, or t
<220> FEATURE:
<221> NAME/KEY: misc_feature
<222> LOCATION: (6696)..(6696)
<223> OTHER INFORMATION: n is a, c, g, or t

<400> SEQUENCE: 6
ggccgcaata gagagtgacc tatccaagct ttgggggtct aagttttaat ggcccaggga    60
```

```
atcattactt tttttctca atccttgatg gataaaagta ttacatacgt acaggattgt      120
gtattagtgt atttcgttat atgattaaac aaagtttata gattgtaaag tagacgtaaa      180
gtttagtaat tcattttaat gttcatttta cattcagatg tcattaagcg gctttagagt      240
tgatttcatc agataattta gcttgagcaa ccaagatttc tggagcatcg aattcatcca      300
agaataattc aatgactcta atcttatctt ccttgttgaa tgcttcatcc ttcatcaaag      360
cgtccaagtc cttagcggat ttaacaacat ggttttcata ttgggtcttg tcagcaaaga      420
gcttcaataa caattggtga tcccatggtt gaatttggtt gtagtcctca tgacgaccgt      480
ggatcaactt ttcgatagtg taacctctgt tgtttaagat gaagatgtat ggcttgatgt      540
tccatcttgc agcatctgag attgattgga cagtcaattg taaagaacca tcaccaataa      600
acaaaacagt tcttctttct tgttcgccag tttgtttgtg tgcatcttca gcagcaaatg      660
cagcaccaac tgcagctggt aaggagaaac caatggaacc ccataagact tgggagatag      720
actttgaatc tcttggtatg ggtagccaag actagtcgat atcacctaat aacttcgtat      780
agcatacatt atacgaagtt atattaaggg ttctcgagaa ttcttgctgc aacggcaaca      840
tcaatgtcca cgtttacaca cctacattta tatctatatt tatatttata tttatttatt      900
tatgctactt agcttctata gttagttaat gcactcacga tattcaaaat tgacacccett      960 caactactcc ctactattgt ctactactgt ctactactcc tctttactat agctgctccc     1020
aataggctcc accaataggc tctgtcaata cattttgcgc cgccacctt caggttgtgt     1080 cactcctgaa ggaccatatt gggtaatcgt gcaatttctg gaagagagtg ccgcgagaag     1140
tgaggccccc actgtaaatc ctcgagggg catggagtat ggggcatgna ggatggagga     1200
tggggggggg gggggaaaat aggtagcgaa aggacccgct atcacccacc ccggagaact     1260
cgttgccggg aagtcatatt tcgacactcc ggggagtcta taaaaggcgg ttttgtctt     1320 ttgccagttg atgttgctga gaggacttgt ttgccgtttc ttccgattta acagtataga     1380
atcaaccact gttaattata cacgttatac taacacaaca aaaacaaaaa caacgacaac     1440
aacaacaaca atgtttgctt tctactttct caccgcatgc accactttga agggtgtttt     1500 cggagttct ccgagttaca atggtcttgg tctcacccca cagatgggtt gggacagctg     1560
gaatacgttt gcctgcgatg tcagtgaaca gctacttcta gacactgctg atagaatttc     1620
tgacttgggg ctaaaggata tgggttacaa gtatgtcatc ctagatgact gttggtctag     1680
cggcagggat tccgacggtt tcctcgttgc agacaagcac aaatttccca acggtatggg     1740
ccatgttgca gaccacctgc ataataacag ctttcttttc ggtatgtatt cgtctgctgg     1800
tgagtacacc tgtgctgggt accctgggtc tctgggcgt gaggaagaag atgctcaatt     1860
ctttgcaaat aaccgcgttg actacttgaa gtatgataat tgttacaata aaggtcaatt     1920
tggtacacca gacgtttctt accaccgtta caaggccatg tcagatgctt tgaataaaac     1980
tggtaggcct attttctatt ctctatgtaa ctggggtcag gatttgacat ttactgggg     2040 ctctggtatc gccaattctt ggagaatgag cggagatatt actgctgagt tcacccgtcc     2100
agatagcaga tgtccctgtg acggtgacga atatgattgc aagtacgccg gtttccattg     2160
ttctattatg aatattctta acaaggcagc tccaatgggg caaatgcag gtgttggtgg     2220 ttggaacgat ctggacaatc tagaggtcgg agtcggtaat ttgactgacg atgaggaaaa     2280
ggcccatttc tctatgtggg caatggtaaa gtccccactt atcattggtg ccgacgtgaa     2340
tcacttaaag gcatcttcgt actcgatcta cagtcaagcc tctgtcatcg caattaatca     2400
```

```
agatccaaag ggtattccag ccacaagagt ctggagatat tatgtttcag acaccgatga    2460
atatggacaa ggtgaaattc aaatgtggag tggtccgctt gacaatgtg accaagtggt     2520 tgctttattg aatggaggaa gcgtagcaag accaatgaac acgaccttgg aagagatttt    2580
ctttgacagc aatttggggtt caaaggaact gacatcgact tgggatattt acgacttatg   2640
ggccaacaga gttgacaact ctacggcgtc tgctatcctt gaacagaata aggcagccac    2700
cggtattctc tacaatgcta cagagcagtc ttataaagac ggtttgtcta agaatgatac    2760
aagactgttt ggccagaaaa ttggtagtct ttctccaaat gctatactta acacaactgt    2820
tccagctcat ggtatcgcct tctataggtt gagaccctcg gcttaagctc aatgttgagc    2880
aaagcaggac gagaaaaaaa aaaataatga ttgttaagaa gttcatgaaa aaaaaaagga    2940
aaaatactca aatacttata acagagtgat taaataataa acggcagtat accctatcag    3000
gtattgagat agttttattt ttgtaggtat ataatctgaa gcctttgaac tattttctcg    3060
tatatatcat ggagtataca ttgcattagc aacattacat actaggatct ctagacctaa    3120
taacttcgta tagcatacat tatacgaagt tatattaagg gttgtcgacg gatccttgct    3180
gcaacggcaa catcaatgtc cacgtttaca cacctacatt tatatctata tttatattta    3240
tatttattta tttatgctac ttagcttcta tagttagtta atgcactcac gatattcaaa    3300
attgacaccc ttcaactact ccctactatt gtctactact gtctactact cctctttact    3360
atagctgctc ccaataggct ccaccaatag gctctgccaa tacattttgc gccgccacct    3420
ttcaggttgt gtcactcctg aaggaccata ttgggtaatc gtgcaatttc tggaagagag    3480
tccgcgagaa gtgaggcccc cactgtaaat cctcgagggg gcatggagta tggggcatgg    3540
aggatggagg atgggggggg gcgaaaaata ggtagcgaaa ggacccgcta tcaccccacc    3600
cggagaactc gttgccggga agtcatattt cgacactccg gggagtctat aaaaggcggg    3660
ttttgtcttt tgccagttga tgttgctgag aggacttgtt tgccgtttct tccgatttaa    3720
cagtatagaa tcaaccactg ttaattatac acgttatact aacacaacaa aaacaaaaac    3780
aacgacaaca acaacaacaa gatccatgga ccaattggtg aaaactgaag tcaccaagaa    3840 gtctttact gctcctgtac aaaaggcttc tacaccagtt ttaaccaata aaacagtcat     3900
ttctggatcg aaagtcaaaa gtttatcatc tgcgcaatcg agctcatcag gaccttcatc    3960
atctagtgag gaagatgatt cccgcgatat tgaaagcttg gataagaaaa tacgtccttt    4020
agaagaatta gaagcattat taagtagtgg aaatacaaaa caattgaaga acaaagaggt    4080
cgctgccttg gttattcacg gtaagttacc tttgtacgct ttggagaaaa aattaggtga    4140
tactacgaga gcggttgcgg tacgtaggaa ggctctttca attttggcag aagctcctgt    4200
attagcatct gatcgtttac catataaaaa ttatgactac gaccgcgtat ttggcgcttg    4260
ttgtgaaaat gttataggtt acatgccttt gcccgttggt gttataggcc ccttggttat    4320
cgatggtaca tcttatcata taccaatggc aactacagag ggttgtttgg tagcttctgc    4380
catgcgtggc tgtaaggcaa tcaatgctgg cggtggtgca acaactgttt taactaagga    4440
tggtatgaca agaggcccag tagtccgttt cccaacttg aaaagatctg gtgcctgtaa     4500
gatatggtta gactcagaag agggacaaaa cgcaattaaa aaagctttta actctacatc    4560
aagatttgca cgtctgcaac atattcaaac ttgtctagca ggagatttac tcttcatgag    4620
atttagaaca actactggtg acgcaatggg tatgaatatg atttctaaag gtgtcgaata    4680
ctcattaaag caaatggtag aagagtatgg ctggaagat atggaggttg tctccgtttc     4740
tggtaactac tgtaccgaca aaaaaccagc tgccatcaac tggatcgaag gtcgtggtaa    4800
```

```
gagtgtcgtc gcagaagcta ctattcctgg tgatgttgtc agaaaagtgt taaaaagtga    4860
tgtttccgca ttggttgagt tgaacattgc taagaatttg gttggatctg caatggctgg    4920
gtctgttggt ggatttaacg cacatgcagc taatttagtg acagctgttt tcttggcatt    4980
aggacaagat cctgcacaaa atgttgaaag ttccaactgt ataacattga tgaaagaagt    5040
ggacggtgat ttgagaattt ccgtatccat gccatccatc gaagtaggta ccatcggtgg    5100
tggtactgtt ctagaaccac aaggtgccat gttggactta ttaggtgtaa gaggcccgca    5160
tgctaccgct cctggtacca acgcacgtca attagcaaga atagttgcct gtgccgtctt    5220
ggcaggtgaa ttatccttat gtgctgccct agcagccggc catttggttc aaagtcatat    5280
gacccacaac aggaaacctg ctgaaccaac aaaacctaac aatttggacg ccactgatat    5340
aaatcgtttg aaagatgggt ccgtcacctg cattaaatcc taaacttagt catacgtcat    5400
tggtattctc ttgaaaaaga agcacaacag caccatgtgg gatcttccaa gctttggact    5460
tcttcgccag aggtttggtc aagtctccaa tcaaggttgt cggcttgtct accttgccag    5520
aaatttacga aagatggaa aagggtcaaa tcgttggtag atacgttgtt gacacttcta    5580
aataagcgaa tttcttatga tttatgattt ttattattaa ataagttata aaaaaaataa    5640
gtgtatacaa attttaaagt gactcttagg ttttaaaacg aaaattctta ttcttgagta    5700
actctttcct gtaggtcagg ttgctttctc aggtatagca tgaggtcgct cttattgacc    5760
acacctctac cggcatgccg agcaaatgcc tgcaaatcgc tccccatttc acccaattgt    5820
agatatgcta actccagcaa tgagttgatg aatctcggtg tgtattttat gtcctcagag    5880
gacaacacct gttgtaatcg ttcttccaca cggatccgta tcatttgtag cccacgccac    5940
ccggaaaaac caccattgtc ctcagcagtc cgccaaaata tggatgcgct caatcaactt    6000
tccctccccc gtcaatgcca aaggataac gacacactat taagagcgca tcatttgtaa    6060
aagccgagga aggggatac gctaaccgga gacgtctcgc ctcactctcg gagctgagcc    6120
gccctcctta agaaattcat gggaagaaca cccttcgcgg cttctgaacg gctcgccctc    6180
gtccattggt cacctcacag tggcaactaa taaggacatt atagcaatag aaattaaaat    6240
ggtgcacaga aatacaatag gatcgaatag gataggatac aataagatac ggaatattag    6300
actatactgt gatacggtac ggtacgatac gctacgatac gatacgatag aggataccac    6360
ggatataacg tagtattatt tttcattatt gggggttttt ttctgtttga attttccacg    6420
tcaagagtat cccatctgac aggaaccgat ggactcgtca cagtacctat cgcccgagtt    6480
caatccatgg acgcttcggg tgaaggatct tcgtccgctg ttggcaagcc atgggatcag    6540
ggcgtcgcca agggacagaa aggcggatct tgtacgtctc ttcaacacag agctgcgtcc    6600
gaaacttact gagagtctta acaccaataa tcccaaaaac aacaacaaca atacagatac    6660
tatagacact atagacacta tagacactac taacancect ttaaagcgcc gccgattaag    6720
caatgttgat gagccgtcaa ttccatatac tctgcagcgt acgaagcttc agctggcggc    6780
cgcgttctat agtgtcacct aaatcgtatg tgtatgatac ataaggttat gtattaattg    6840
tagccgcgtt ctaacgacaa tatgtccata tggtgcactc tcagtacaat ctgctctgat    6900
gccgcatagt taagccagcc ccgacacccg ccaacacccg ctgacgcgcc ctgacgggct    6960
tgtctgctcc cggcatccgc ttacagacaa gctgtgaccg tctccgggag ctgcatgtgt    7020
cagaggtttt caccgtcatc accgaaacgc gcgagacgaa agggcctcgt gatacgccta    7080
tttttatagg ttaatgtcat gataataatg gtttcttaga cgtcaggtgg cacttttcgg    7140
```

```
ggaaatgtgc gcggaacccc tatttgttta tttttctaaa tacattcaaa tatgtatccg    7200
ctcatgagac aataaccctg ataaatgctt caataatatt gaaaaaggaa gagtatgagt    7260
attcaacatt tccgtgtcgc ccttattccc tttttgcgg cattttgcct tcctgttttt    7320
gctcacccag aaacgctggt gaaagtaaaa gatgctgaag atcagttggg tgcacgagtg    7380
ggttacatcg aactggatct caacagcggt aagatccttg agagttttcg ccccgaagaa    7440
cgttttccaa tgatgagcac ttttaaagtt ctgctatgtg gcgcggtatt atcccgtatt    7500
gacgccgggc aagagcaact cggtcgccgc atacactatt ctcagaatga cttggttgag    7560
tactcaccag tcacagaaaa gcatcttacg gatggcatga cagtaagaga attatgcagt    7620
gctgccataa ccatgagtga taacactgcg gccaacttac ttctgacaac gatcggagga    7680
ccgaaggagc taaccgcttt tttgcacaac atggggatc atgtaactcg ccttgatcgt    7740
tgggaaccgg agctgaatga agccatacca aacgacgagc gtgacaccac gatgcctgta    7800
gcaatggcaa caacgttgcg caaactatta actggcgaac tacttactct agcttcccgg    7860
caacaattaa tagactggat ggaggcggat aaagttgcag gaccacttct gcgctcggcc    7920
cttccggctg gctggtttat tgctgataaa tctggagccg gtgagcgtgg gtctcgcggt    7980
atcattgcag cactggggcc agatggtaag ccctcccgta tcgtagttat ctacacgacg    8040
gggagtcagg caactatgga tgaacgaaat agacagatcg ctgagatagg tgcctcactg    8100
attaagcatt ggtaactgtc agaccaagtt tactcatata ctttagat tgatttaaaa    8160
cttcattttt aatttaaaag gatctaggtg aagatccttt ttgataatct catgaccaaa    8220
atcccttaac gtgagttttc gttccactga gcgtcagacc ccgtagaaaa gatcaaagga    8280
tcttcttgag atccttttt tctgcgcgta atctgctgct tgcaaacaaa aaaaccaccg    8340
ctaccagcgg tggtttgttt gccggatcaa gagctaccaa ctcttttcc gaaggtaact    8400
ggcttcagca gagcgcagat accaaatact gtccttctag tgtagccgta gttaggccac    8460
cacttcaaga actctgtagc accgcctaca tacctcgctc tgctaatcct gttaccagtg    8520
gctgctgcca gtggcgataa gtcgtgtctt accgggttgg actcaagacg atagttaccg    8580
gataaggcgc agcggtcggg ctgaacgggg gttcgtgca cacagcccag cttggagcga    8640
acgacctaca ccgaactgag atacctacag cgtgagcatt gagaaagcgc cacgcttccc    8700
gaagggagaa aggcggacag gtatccggta agcggcaggg tcggaacagg agagcgcacg    8760
agggagcttc caggggggaaa cgcctggtat ctttatagtc ctgtcgggtt cgccacctc    8820
tgacttgagc gtcgattttt gtgatgctcg tcagggggc ggagcctatg gaaaaacgcc    8880
agcaacgcgg cctttttacg gttcctggcc ttttgctggc cttttgctca catgttcttt    8940
cctgcgttat cccctgattc tgtggataac cgtattaccg cctttgagtg agctgatacc    9000
gctcgccgca gccgaacgac cgagcgcagc gagtcagtga gcgaggaagc ggaagagcgc    9060
ccaatacgca aaccgcctct ccccgcgcgt tggccgattc attaatgcag gttaacctgg    9120
cttatcgaaa ttaatacgac tcactatagg gagaccggca gatccgc              9167
```

```
<210> SEQ ID NO 7
<211> LENGTH: 36
<212> TYPE: DNA
<213> ORGANISM: Artificial
<220> FEATURE:
<223> OTHER INFORMATION: primer

<400> SEQUENCE: 7
agcgcggatc catggaccaa ttggtgaaaa ctgaag                              36
```

<210> SEQ ID NO 8
<211> LENGTH: 32
<212> TYPE: DNA
<213> ORGANISM: Artificial
<220> FEATURE:
<223> OTHER INFORMATION: primer

<400> SEQUENCE: 8
agcgcggatc ccacatggtg ctgttgtgct tc         32

<210> SEQ ID NO 9
<211> LENGTH: 9935
<212> TYPE: DNA
<213> ORGANISM: Artificial
<220> FEATURE:
<223> OTHER INFORMATION: vector for expression of I. batatas IspS and S.
      cerevisiae IDI1 was named pPK-IspS-IDI
<220> FEATURE:
<221> NAME/KEY: misc_feature
<222> LOCATION: (957)..(957)
<223> OTHER INFORMATION: n is a, c, g, or t

<400> SEQUENCE: 9
ggccgcatag gccactagtt caaagggaat gtgataatgc aaggttaggt ttaacaagaa      60
tgggttggcg gactcgtcaa tggagagtac aatgccaaag ttctccttga ggttatttaa     120
tcttccacag gttcaaggca ttctggcagc ttctcaattg ggaagttttc gtagatgata     180
cggtaggtgg tggtaaatag tgggaactca tctgtcctgc ccatgttgga gaggaactcg     240
taaacttccc tagttgtgtg gataccttga caggattggc cattcaacaa ctttctcttca    300 gcctccgttg cagagacaga atgttgtgcc atatatctac caactctaac gttacggccg     360
ccggcacagg tagtgattag gtcggcaaca cctgcagatt catgagtaaa ggttgcagca     420
tgacagccat cgaaaaaagt cttggcaaat tgaatggttt ccaccaaacc tattctcatg     480
actgcagcct ttgcattatc accccaacct aaaccttcga caaatgatat cacctaataa     540
cttcgtatag catacattat acgaagttat attaagggtt ctcgagaatt cttgctgcaa     600
cggcaacatc aatgtccacg tttacacacc tacatttata tctatattta tatttatatt     660
tatttattta tgctacttag cttctatagt tagttaatgc actcacgata ttcaaaattg     720
acacccttca actactccct actattgtct actactgtct actactcctc tttactatag     780
ctgctcccaa taggctccac caataggctc tgtcaataca ttttgcgccg ccacctttca     840
ggttgtgtca ctcctgaagg accatattgg gtaatcgtgc aatttctgga agagagtgcc     900
gcgagaagtg aggcccccac tgtaaatcct cgaggggggca tggagtatgg ggcatgnagg    960
atggaggatg ggggggggggg gggaaaatag gtagcgaaag gacccgctat cacccaccc    1020 ggagaactcg ttgccgggaa gtcatatttc gacactccgg ggagtctata aaaggcgggt    1080
tttgtctttt gccagttgat gttgctgaga ggacttgttt gccgtttctt ccgatttaac    1140
agtatagaat caaccactgt taattataca cgttatacta acacaacaaa acaaaaaaca    1200
acgacaacaa caacaacaat gcctgaactc accgcgacgt ctgtcgagaa gtttctgatc    1260
gaaaagttcg acagcgtctc cgacctgatg cagctctcgg agggcgaaga atctcgtgct    1320
ttcagcttcg atgtaggagg gcgtggatat gtcctgcggg taaatagctg cgccgatggt    1380
ttctacaaag atcgttatgt ttatcggcac tttgcatcgg ccgcgctccc gattccggaa    1440
gtgcttgaca ttggggaatt cagcgagagc ctgacctatt gcatctcccg ccgtgcacag    1500
ggtgtcacgt tgcaagacct gcctgaaacc gaactgcccg ctgttctgca gccggtcgcg    1560

```
gaggccatgg atgcgatcgc tgcggccgat cttagccaga cgagcgggtt cggcccattc    1620
ggaccgcaag gaatcggtca atacactaca tggcgtgatt tcatatgcgc gattgctgat    1680
ccccatgtgt atcactggca aactgtgatg gacgacaccg tcagtgcgtc cgtcgcgcag    1740
gctctcgatg agctgatgct ttgggccgag gactgccccg aagtccggca cctcgtgcac    1800
gcggatttcg gctccaacaa tgtcctgacg gacaatggcc gcataacagc ggtcattgac    1860
tggagcgagg cgatgttcgg ggattcccaa tacgaggtcg ccaacatctt cttctggagg    1920
ccgtggttgg cttgtatgga gcagcagacg cgctacttcg agcggaggca tccggagctt    1980
gcaggatcgc cgcggctccg ggcgtatatg ctccgcattg gtcttgacca actctatcag    2040
agcttggttg acggcaattt cgatgatgca gcttgggcgc agggtcgatg cgacgcaatc    2100
gtccgatccg gagccgggac tgtcgggcgt acacaaatcg cccgcagaag cgcggccgtc    2160
tggaccgatg gctgtgtaga agtactcgcc gatagtggaa accgacgccc cagcactcgt    2220
ccgagggcaa aggaatagag tagtaagctc aatgttgagc aaagcaggac gagaaaaaaa    2280
aaaataatga ttgttaagaa gttcatgaaa aaaaaagga aaaatactca aatacttata    2340
acagagtgat taaataataa acggcagtat accctatcag gtattgagat agttttattt    2400
ttgtaggtat ataatctgaa gcctttgaac tattttctcg tatatatcat ggagtataca    2460
ttgcattagc aacattacat actaggatct ctagacctaa taacttcgta tagcatacat    2520
tatacgaagt tatattaagg gttgtcgacg gatccttgct gcaacggcaa catcaatgtc    2580
cacgtttaca cacctacatt tatatctata tttatattta tatttattta tttatgctac    2640
ttagcttcta tagttagtta atgcactcac gatattcaaa attgacaccc ttcaactact    2700
ccctactatt gtctactact gtctactact cctctttact atagctgctc ccaataggct    2760
ccaccaatag gctctgccaa tacattttgc gccgccacct ttcaggttgt gtcactcctg    2820
aaggaccata ttgggtaatc gtgcaatttc tggaagagag tccgcgagaa gtgaggcccc    2880
cactgtaaat cctcgagggg gcatggagta tgggcatgg aggatggagg atgggggggg    2940
gcgaaaaata ggtagcgaaa ggacccgcta tcaccccacc cggagaactc gttgccggga    3000
agtcatattt cgacactccg gggagtctat aaaaggcggg ttttgtcttt tgccagttga    3060
tgttgctgag aggacttgtt tgccgttttct tccgatttaa cagtatagaa tcaaccactg    3120
ttaattatac acgttatact aacacaacaa aaacaaaaac aacgacaaca acaacaacaa    3180
gatccaaaat gacagccaga agatcagcaa actatcaacc ttcatcatgg tcctacgacg    3240
aatacttggt cgatacaaca acaaacgatt ctaaattaag aatacaagaa gacgcaagaa    3300
agaaattgga agaagaagta agaaacgttt tggaagatgg taaattagaa actttggcct    3360
tgttggaatt gatcgatgac attcaaagat tgggtttagg ttacaagttt agagaatcaa    3420
catccaccag tttagccatg ttgaagatgt cagttggtca agaagcatct aattcttctt    3480
tgcattcttg ttcattgtac tttagattgt tgagagaaca cggtttcgat ataacaccag    3540
acgtattcga aaaattcaag gatgaaaacg gtaaattcaa agattctatc gctaaggatg    3600
ttagaggttt gttaagttta tatgaagcat cattttttggg tttcgaaggt gaaaacatat    3660
tggatgaagc tagagagttt actacaatgc acttgaataa catcaaggat aaggtcaacc    3720
caagaatagc agaagaagta aaccatgcct tggaattacc tttgcacaga agagttgaaa    3780
gattagaagc tagaagaaga atacaatcct acagtaagtc tggtgaaacc aatcaagcat    3840
tgttgacttt ggcaaagatc gatttcaaca ctgtccaagc agtataccaa agagatttgc    3900
```

```
aagacgtttc aaaatggtgg aaggacacag ctttagcaga taaattgtcc ttcgcaagag    3960
atagattgat ggaatctttc ttttgggcca tcggcatgtc ttacgatcca caacactcaa    4020
agtccagaga agctgtcact aagactttta aattggttac cgtcttggat gacgtttatg    4080
acgtctacgg ttcttttagat gaattggaaa aattcactgc tgcagccgaa agatgggatg   4140
tagacgctat aaaagatttg cctgactaca tgaagttgtg ttacttatca ttgtttaata    4200
ctgttaacga tttggcatat gacacattga agataaggg tgaaaccgtc attccaataa     4260 tgaaaaggc ttgggctgat ttgttaaaag ccttcttaca agaagctcaa tggatctata     4320
ataagtacac ccctactttc gatgaatact taaataacgc tagattcagt gtttctggtt    4380
gcgtaatgtt ggttcattct tactttacca ctcaaaacat cacaaaggaa gcaatccata    4440
gtttggaaaa ctaccacgac ttgttaatat ggccttctat cgtcttcaga ttagctaatg    4500
atttgtccag ttctaaggca gaaatcgaaa gaggtgaaac tgccaattct atcacatgtt    4560
acatgaacga aacaggtcaa tcagaagaac aagctagaga acatatctcc aaattgatcg    4620
atgaatgctt caaaaagatg aataaggaaa tgttggccac atcaacctcc ccatttgaaa    4680
aatcattcat cgaaaccgct attaacttag caagaattgc cttgtgccaa tatcaatacg    4740
gtgacgctca ctctgatcct gacgttagag caagaaatag aatcgtaagt gtcatcatta    4800
atccagtcga atggtcacat ccacaatttg aaaagtaata gggatcttcc aagctttgga    4860
cttcttcgcc agaggtttgg tcaagtctcc aatcaaggtt gtcggcttgt ctaccttgcc    4920
agaaatttac gaaagatgg aaaagggtca atcgttggt agatacgttg ttgacacttc      4980
taaataagcg aatttcttat gatttatgat tttattatt aaataagtta taaaaaaaat     5040
aagtgtatac aaattttaaa gtgactctta ggttttaaaa cgaaaattct tattcttgag    5100
taactctttc ctgtaggtca ggttgctttc tcaggtatag catgaggtcg ctcttattga    5160
ccacacctct accggcatgc gatatggata tggatatgga tatggagatg aatttgaatt    5220
tagatttggg tcttgatttg gggttggaat taaaagggga taacaatgag ggttttcctg    5280
ttgatttaaa caatggacgt gggaggtgat tgatttaacc tgatccaaaa ggggtatgtc    5340
tattttttag agagtgtttt tgtgtcaaat tatggtagaa tgtgtaaagt agtataaact    5400
ttcctctcaa atgacgaggt ttaaaacacc ccccgggtga gccgagccga aatgggca      5460 attgttcaat gtgaaataga agtatcgagt gagaaacttg ggtgttggcc agccaagggg    5520
gggggggaag gaaaatggcg cgaatgctca ggtgagattg ttttggaatt gggtgaagcg    5580
aggaaatgag cgacccggag gttgtgactt tagtggcgga ggaggacgga ggaaaagcca   5640
agagggaagt gtatataagg ggagcaattt gccaccagga tagaattgga tgagttataa    5700
ttctactgta tttattgtat aatttatttc tccttttgta tcaaacacat tacaaaaacac   5760 acaaaacaca caaacaaaca caattacaaa aattaattaa aaaatgactg ccgacaacaa    5820
tagtatgccc catggtgcag tatctagtta cgccaaatta gtgcaaaacc aaacacctga    5880
agacattttg gaagagtttc ctgaaattat tccattacaa caaagaccta atacccgatc    5940
tagtgagacg tcaaatgacg aaagcggaga acatgttttt tctggtcatg atgaggagca    6000
aattaagtta atgaatgaaa attgtattgt tttggattgg gacgataatg ctattggtgc    6060
cggtaccaag aaagtttgtc atttaatgga aaatattgaa aagggtttac tacatcgtgc    6120
attctccgtc tttatttttca atgaacaagg tgaattactt ttacaacaaa gagccactga    6180
aaaaataact ttccctgatc tttggactaa cacatgctgc tctcatccac tatgtattga    6240
tgacgaatta ggtttgaagg gtaagctaga cgataagatt aagggcgcta ttactgcggc    6300
```

```
ggtgagaaaa ctagatcatg aattaggtat tccagaagat gaaactaaga caagggtaa    6360
gtttcacttt ttaaacagaa tccattacat ggcaccaagc aatgaaccat ggggtgaaca   6420
tgaaattgat tacatcctat tttataagat caacgctaaa gaaaacttga ctgtcaaccc   6480
aaacgtcaat gaagttagag acttcaaatg ggtttcacca aatgatttga aaactatgtt   6540
tgctgaccca agttacaagt ttacgccttg gtttaagatt atttgcgaga attacttatt   6600
caactggtgg gagcaattag atgacctttc tgaagtggaa aatgacaggc aaattcatag   6660
aatgctataa ttaattaacc catgtctcta ctggtggtgg tgcttctttg gaattattgg   6720
aaggtaagga attgccaggt gttgctttct tatccgaaaa gaaataaatt gaattgaatt   6780
gaaatcgata gatcaatttt tttctttttct ctttccccat cctttacgct aaaataatag   6840
tttattttat ttttgaata tttttttattt atatacgtat atatagacta ttatttatct   6900
tttaatgatt attaagattt ttattaaaaa aaaattcgct cctcttttaa tgcctttatg   6960
cagtttttt tcccattcg atatttctat gttcgggttc agcgtatttt aagtttaata   7020
actcgaaaat tctgcgttcg ttaacctgca gggatccatt cttggtaaaa attggtgagg   7080
aatattaaag acaatcaagt ctgagcctgc acaagcctca acaatgtctg gaactgcaac   7140
aacgttaact ggcaacttga tacctggcaa gtacttgacg ttttcgtgtt tggtatttat   7200
gatttcagtc aacttttcgc cttcaatcaa ttcttcatag acccacatat taacatctct   7260
ttgaaattga cgaggtctct caacggtgtt ttccgctata accttggcaa ttgtacaccc   7320
ccagttaccg gaaccaacaa ccgtcacctt gaacggatgt tccggatagt cttctggttg   7380
taatgatgta gaatcttttc tgtttggctt gattgtggac gcaatagtag ataatctttc   7440
agcaggggac accattttaa tgtttgatct attcaatgtc ttgatagtat ttgagaaact   7500
ccttgtaaag tgtaaactct ttgagattag aaacatacag ctggcggccg cgttctatag   7560
tgtcacctaa atcgtatgtg tatgatacat aaggttatgt attaattgta gccgcgttct   7620
aacgacaata tgtccatatg gtgcactctc agtacaatct gctctgatgc cgcatagtta   7680
agccagcccc gacacccgcc aacaccgct gacgcgccct gacgggcttg tctgctcccg   7740
gcatccgctt acagacaagc tgtgaccgtc tccgggagct gcatgtgtca gaggttttca   7800
ccgtcatcac cgaaacgcgc gagacgaaag ggcctcgtga tacgcctatt tttataggtt   7860
aatgtcatga taataatggt ttcttagacg tcaggtggca cttttcgggg aaatgtgcgc   7920
ggaaccccta tttgtttatt tttctaaata cattcaaata tgtatccgct catgagacaa   7980
taaccctgat aaatgcttca ataatattga aaaggaaga gtatgagtat tcaacatttc   8040
cgtgtcgccc ttattccctt ttttgcggca ttttgccttc ctgtttttgc tcacccagaa   8100
acgctggtga aagtaaaaga tgctgaagat cagttgggtg cacgagtggg ttacatcgaa   8160
ctggatctca acagcggtaa gatccttgag agttttcgcc ccgaagaacg ttttccaatg   8220
atgagcactt ttaaagttct gctatgtggc gcggtattat cccgtattga cgccgggcaa   8280
gagcaactcg gtcgccgcat acactattct cagaatgact tggttgagta ctcaccagtc   8340
acagaaaagc atcttacgga tggcatgaca gtaagagaat tatgcagtgc tgccataacc   8400
atgagtgata acactgcggc caacttactt ctgacaacga tcggaggacc gaaggagcta   8460
accgcttttt tgcacaacat gggggatcat gtaactcgcc ttgatcgttg ggaaccggag   8520
ctgaatgaag ccataccaaa cgacgagcgt gacaccacga tgcctgtagc aatggcaaca   8580
acgttgcgca aactattaac tggcgaacta cttactctag cttcccggca acaattaata   8640
```

```
gactggatgg aggcggataa agttgcagga ccacttctgc gctcggccct tccggctggc      8700
tggtttattg ctgataaatc tggagccggt gagcgtgggt ctcgcggtat cattgcagca      8760
ctggggccag atggtaagcc ctcccgtatc gtagttatct acacgacggg gagtcaggca      8820
actatggatg aacgaaatag acagatcgct gagataggtg cctcactgat taagcattgg      8880
taactgtcag accaagttta ctcatatata ctttagattg atttaaaact tcattttaa      8940 tttaaaagga tctaggtgaa gatccttttt gataatctca tgaccaaaat cccttaacgt      9000
gagttttcgt tccactgagc gtcagacccc gtagaaaaga tcaaggatc ttcttgagat      9060 cctttttttc tgcgcgtaat ctgctgcttg caaacaaaaa aaccaccgct accagcggtg      9120
gtttgtttgc cggatcaaga gctaccaact cttttccga aggtaactgg cttcagcaga      9180
gcgcagatac caaatactgt ccttctagtg tagccgtagt taggccacca cttcaagaac      9240
tctgtagcac cgcctacata cctcgctctg ctaatcctgt taccagtggc tgctgccagt      9300
ggcgataagt cgtgtcttac cgggttggac tcaagacgat agttaccgga taaggcgcag      9360
cggtcgggct gaacgggggg ttcgtgcaca gcccagct tggagcgaac gacctacacc      9420
gaactgagat acctacagcg tgagcattga gaaagcgcca cgcttcccga agggagaaag      9480
gcggacaggt atccggtaag cggcagggtc ggaacaggag agcgcacgag ggagcttcca      9540
gggggaaacg cctggtatct ttatagtcct gtcgggtttc gccacctctg acttgagcgt      9600 cgattttttgt gatgctcgtc agggggggcgg agcctatgga aaaacgccag caacgcggcc      9660
tttttacggt tcctggcctt ttgctggcct tttgctcaca tgttctttcc tgcgttatcc      9720
cctgattctg tggataaccg tattaccgcc tttgagtgag ctgataccgc tcgccgcagc      9780
cgaacgaccg agcgcagcga gtcagtgagc gaggaagcgg aagagcgccc aatacgcaaa      9840
ccgcctctcc ccgcgcgttg gccgattcat taatgcaggt taacctggct tatcgaaatt      9900
aatacgactc actataggga gaccggcaga tccgc                                9935

<210> SEQ ID NO 10
<211> LENGTH: 70
<212> TYPE: DNA
<213> ORGANISM: Artificial
<220> FEATURE:
<223> OTHER INFORMATION: Primer

<400> SEQUENCE: 10 cttttttacaa caaatataaa accaaaagcg gccgcttaat taaaaaatga ctgccgacaa       60
caatagtatg                                                             70

<210> SEQ ID NO 11
<211> LENGTH: 61
<212> TYPE: DNA
<213> ORGANISM: Artificial
<220> FEATURE:
<223> OTHER INFORMATION: Primer

<400> SEQUENCE: 11
agagacatgg gagatcccgc gggcggccgc ttaattaatt atagcattct atgaatttgc       60
c                                                                      61

<210> SEQ ID NO 12
<211> LENGTH: 14515
<212> TYPE: DNA
<213> ORGANISM: Artificial
<220> FEATURE:
<223> OTHER INFORMATION: vector for expression of I. batatas IspS in T.
``` reesei named pCIL-105

<400> SEQUENCE: 12

```
gtttaaactc aggtcaacca ccgaggacca gcctttgacc gccattgctc ccgttcgtgc      60
cggcagagtt gggtctggat acgccgtctt catacctatc cagctctcac catgcagggt     120
ttccatctgt ttgaagcatc cattcgcagc gcgcgagacc gctactgctt cgtgactata     180
cagtacatgt aataccaaca ggagtcgagg atacgagtac taagtaccac ctattaatct     240
gctgctcgtg cctcgtccgc attgaaagcg aggtaaggta ggcagaaccg ctgacccgtc     300
ccccatcagg tgatgataca acagggtagt actgcggtga cctcgagata aagtacacct     360
cgtgctctgg acgccggcaa cggtaccccta atccgaggtc caaatctgct cgcgcggcct     420
gaggcagaga caccaccgtt tgttgatctc ggttgcccca tcagccagcc agcgcacctc     480
agttaggctc ggacctgggc aaaagttggg gtaacaaagg ccggcggcca aagcacccaa     540
gtacctctgc ccgccattgc gggtgcagag gtgacttccg cgggccatca cggtggcgcc     600
ccttgcaggg agtggtgcgt catcggctcg tcagcacggc caatagacgc aaccggcggc     660
cctgctttca atgttgactg ccccaggccg agtccagtga ccaccgata gcaccatcgc      720
agccacccca aatgcgacct gcaccgcgct ggccagggcc cttcggggcg cctgttagtg     780
cctgcggttg ctcggcgggc gggctgctta acgtgctttg cgtgctgagc tgcctgcctg     840
ccgcccgctc gccttatcta atgcccgcta cctctcctcc gtactccgtc cctacaaaga     900
ggctggttcc tagcttcgtc atcctccaag ttcccttcct ctggcagcaa tcgaaccatc     960
ccattcatta attaagctcc ttattgaagt cggaggacgg agcggtgtca agaggatatt    1020
cttcgactct gtattataga taagatgatg aggaattgga ggtagcatag cttcatttgg    1080
atttgctttc caggctgaga ctctagcttg gagcatagag ggtcctttgg cttttcaatat   1140
tctcaagtat ctcgagtttg aacttattcc ctgtgaacct tttattcacc aatgagcatt    1200
ggaatgaaca tgaatctgag gactgcaatc gccatgaggt tttcgaaata catccggatg    1260
tcgaaggctt ggggcacctg cgttggttga atttagaacg tggcactatt gatcatccga    1320
tagctctgca aagggcgttg cacaatgcaa gtcaaacgtt gctagcagtt ccaggtggaa    1380
tgttatgatg agcattgtat taaatcagga gatatagcat gatctctagt tagctcacca    1440
caaaagtcag acggcgtaac caaaagtcac acaacacaag ctgtaaggat ttcggcacgg    1500
ctacggaaga cggagaagcc accttcagtg gactcgagta ccatttaatt ctatttgtgt    1560
ttgatcgaga cctaatacag cccctacaac gaccatcaaa gtcgtatagc taccagtgag    1620
gaagtggact caaatcgact tcagcaacat ctcctggata aactttaagc ctaaactata    1680
cagaataaga taggtggaga gcttataccg agctcccaaa tctgtccaga tcatggttga    1740
ccggtgcctg gatcttccta tagaatcatc cttattcgtt gacctagctg attctggagt    1800
gacccagagg gtcatgactt gagcctaaaa tccgccgcct ccaccattttg tagaaaaatg    1860
tgacgaactc gtgagctctg tacagtgacc ggtgactctt tctggcatgc ggagagacgg    1920
acggacgcag agagaagggc tgagtaataa gccactggcc agacagctct ggcggctctg    1980
aggtgcagtg gatgattatt aatccgggac cggccgcccc tccgcccgga gtggaaagg     2040
ctggtgtgcc cctcgttgac caagaatcta ttgcatcatc ggagaatatg gagcttcatc    2100
gaatcaccgg cagtaagcga aggagaatgt gaagccaggg gtgtatagcc gtcggcgaaa    2160
tagcatgcca ttaacctagg tacagaagtc caattgcttc cgatctggta aaagattcac    2220
gagatagtac cttctccgaa gtaggtagag cgagtacccg gcgcgtaagc tccctaattg    2280
```

```
gcccatccgg catctgtagg gcgtccaaat atcgtgcctc tcctgctttg cccggtgtat   2340
gaaaccggaa aggccgctca ggagctggcc agcggcgcag accgggaaca caagctggca   2400
gtcgacccat ccggtgctct gcactcgacc tgctgaggtc cctcagtccc tggtaggcag   2460 cttttgccccg tctgtccgcc cggtgtgtcg gcggggttga caaggtcgtt gcgtcagtcc   2520
aacatttgtt gccatatttt cctgctctcc ccaccagctg ctcttttctt ttctctttct   2580
tttcccatct tcagtatatt catcttccca tccaagaacc tttatttccc ctaagtaagt   2640
actttgctac atccatactc catccttccc atcccttatt cctttgaacc tttcagttcg   2700
agctttccca cttcatcgca gcttgactaa cagctacccc gcttgagcag acatcatgac   2760
tgcccgccgc tcagcaaact atcaaccctc tcatggtct tacgacgaat acttggtgga   2820
cactactact aacgcacagca aactgcgcat tcaagaagac gctcgtaaaa aattggaaga   2880
agaagtgcgt aacgttctgg aagatggcaa attggaaacc ttagcactgt tggaactgat   2940
tgatgacatc caacggctgg gcttgggtta taaatttcgc gaaagcacca gtacttccct   3000
ggctatgttg aaaatgagtg tggggcagga agcatccaac agcagtttgc attcttgttc   3060
attgtacttt cgtttactgc gggaacacg cttcgatatt accccccgacg tgttcgaaaa   3120 attcaaagat gaaaacggta aatttaaaga tagcatcgct aaagatgttc gcgggttgtt   3180
atcattgtat gaagcaagct ttttagggtt cgaaggcgaa acatttttgg acgaagcccg   3240
cgaattcacc actatgcatc tgaataacat caaagataaa gtgaatcccc gtatcgcgga   3300
agaagttaac catgctttag aactgccgtt gcaccgccgt gtggaacgtc tggaagctcg   3360
gcgccgtatt caaagctata gtaaatccgg tgaaaccaat caggccctgc tgaccctggc   3420
taaaatcgat tttaacaccg tgcaggcggt ttaccaacgg atctgcagg acgttagtaa   3480 atggtggaaa gacactgcat tggccgataa attatccttc gcccgggatc gctgatgga   3540 aagcttttc tgggcgattg gtatgagcta tgatccccaa cactctaaat cacgggaagc   3600
cgtgaccaaa acttttaaac tggtgaccgt tttggatgac gtgtatgacg tttacgggtc   3660
tttagatgaa ctggaaaaat tcaccgccgc cgccgaacgt tgggatgttg acgcgattaa   3720
agatctgccg gactacatga aattgtgtta cttatccctg tttaataccg tgaacgatct   3780
ggcttatgac accttgaaag ataaaggcga aactgttatt cctatcatga agaaagcctg   3840
ggctgattta ctgaaagcat ttctgcagga agcccaatgg atctacaaca aatacacccc   3900
aactttcgat gaatacctga ataacgcccg tttcagcgtg agtggttgcg tgatgttggt   3960
tcatagctac tttaccactc agaacatcac caaagaagcg atccattctc tggaaaaacta   4020 ccacgacttg ttaatttggc ctagcatcgt tttccgttta gcaaatgatc tgtcctcttc   4080
aaaagccgaa attgaacggg gcgaaaccgc gaatagcatc acttgttata tgaacgaaac   4140
cggtcaaagt gaagaacagg cccgtgaaca catttccaaa ctgatcgatg aatgcttcaa   4200
gaaaatgaac aaagaaatgc tggccaccctc cacttctccg tttgaaaaat ccttcattga   4260
aaccgcgatc aacttagcac gcattgccct gtgccagtat caatacggcg atgcccatag   4320
cgatccagat gttcgggcac gcaaccgcat tgtgtcagtt atcattaatc cagtggaatg   4380
gtcccaccca caatttgaaa agtaagatcc acttaacgtt actgaaatca tcaaacagct   4440
tgacgaatct ggatataaga tcgttggtgt cgatgtcagc tccggagttg agacaaatgg   4500
tgttcaggat ctcgataaga tacgttcatt tgtccaagca gcaaagagtg ccttctagtg   4560
atttaatagc tccatgtcaa caagaataaa acgcgtttcg ggtttaccte ttccagatac   4620
```

```
agctcatctg caatgcatta atgcattgga cctcgcaacc ctagtacgcc cttcaggctc   4680
cggcgaagca gaagaatagc ttagcagagt ctattttcat tttcgggaga cgagatcaag   4740
cagatcaacg gtcgtcaaga gacctacgag actgaggaat ccgctcttgg ctccacgcga   4800
ctatatattt gtctctaatt gtactttgac atgctcctct tctttactct gatagcttga   4860
ctatgaaaat tccgtcacca gcccctgggt tcgcaaagat aattgcactg tttcttcctt   4920
gaactctcaa gcctcaggat cacacattca tcgtaggtat aaacctcgaa aatcattcct   4980
actaagatgg gtatacaata gtaaccatgc atggttgcct agtgaatgct ccgtaacacc   5040
caatacgccg gccgaaactt ttttacaact ctcctatgag tcgtttaccc agaatgcaca   5100
ggtacacttg tttagaggta atccttcttt ctagaagtcc tcgtgtactg tgtaagcgcc   5160
cactccacat ctccactctt aattaagcgg ccgcataacg gtgagactag cggccggtcc   5220
ccttatccca gctgttccac gttggcctgc ccctcagtta gcgctcaact caatgcccct   5280
cactggcgag gcgagggcaa ggatggaggg gcagcatcgc ctgagttgga gcaaagcggc   5340
cccatgggag cagcgaacca acggagggat gccgtgcttt gtcgtggctg ctgtggccaa   5400
tccgggccct tggttggctc acagagcgtt gctgtgagac catgagctat tattgctagg   5460
tacagtatag agagaggaga gagagagaga gagagagaga ggggaaaaaa ggtgaggttg   5520
aagtgagaaa aaaaaaaaaa aaaaaaatc caaccactga cggctgccgg ctctgccacc   5580
cccctccctc caccccagac cacctgcaca ctcagcgcgc agcatcacct aatcttggct   5640
cgccttcccg cagctcaggt tgtttttttt ttctctctcc ctcgtcgaag ccgcccttgt   5700
tcccttattt atttccctct ccatccttgt ctgcctttgg tccatctgcc cctttgtctg   5760
catctctttt gcacgcatcg ccttatcgtc gtctcttttt tcactcacgg gagcttgacg   5820
aagacctgac tcgtgagcct cacctgctga tttctctccc ccctcccga ccggcttgac   5880
ttttgtttct cctccagtac cttatcgcga agccggaaga acctcttaac ctctagatga   5940
aaaagcctga actcaccgcg acgtctgtcg agaagttcct gatcgaaaag ttcgacagcg   6000
tctccgacct gatgcagctc tcggagggcg aagaatctcg tgctttcagc ttcgatgtag   6060
gagggcgtgg atatgtcctg cgggtaaata gctgcgccga tggtttctac aaagatcgtt   6120
atgtttatcg gcactttgca tcggccgcgc tcccgattcc ggaagtgctt gacattgggg   6180
aattcagcga gagcctgacc tattgcatct cccgccgtgc acagggtgtc acgttgcaag   6240
acctgcctga aaccgaactg cccgctgttc tgcagccggt cgcggaggcc atggatgcga   6300
tcgctgcggc cgatctcagc cagacgagcg ggttcggccc attcggaccg caaggaatcg   6360
gtcaatacac tacatggcgt gatttcatat gcgcgattgc tgatccccat gtgtatcact   6420
ggcaaactgt gatggacgac accgtcagtg cgtccgtcgc gcaggctctc gatgagctga   6480
tgctttgggc cgaggactgc cccgaagtcc ggcacctcgt gcacgcggat ttcggctcca   6540
acaatgtcct gacggacaat ggccgcataa cagcggtcat tgactggagc gaggcgatgt   6600
tcggggattc ccaatacgag gtcgccaaca tcttcttctg gaggccgtgg ttggcttgta   6660
tggagcagca gacgcgctac ttcgagcgga ggcacccgga gcttgcagga tcgccgcggc   6720
tccggcgta tatgctccgc attggtcttg accaactcta tcagagcttg gttgacggca   6780
atttcgatga tgcagcttgg gcgcagggtc gatgcgacgc aatcgtccga tccggagccg   6840
ggactgtcgg gcgtacacaa atcgcccgca gaagcgcggc cgtctggacc gatggctgtg   6900
tagaagtact cgccgatagt ggaaaccgac gccccagcac tcgtccgagg gcaaaggaat   6960
agatgcatgg ctttcgtgac cgggcttcaa acaatgatgt gcgatggtgt ggttcccggt   7020
```

```
tggcggagtc tttgtctact ttggttgtct gtcgcaggtc ggtagaccgc aaatgagcaa    7080
ctgatggatt gttgccagcg atactataat tcacatggat ggtctttgtc gatcagtagc    7140
tagtgagaga gagagaacat ctatccacaa tgtcgagtgt ctattagaca tactccgaga    7200
ataaagtcaa ctgtgtctgt gatctaaaga tcgattcggc agtcgagtag cgtataacaa    7260
ctccgagtac cagcgaaagc acgtcgtgac aggagcaggg ctttgccaac tgcgcaacct    7320
tgcttgaatg aggatacacg gggtgcaaca tggctgtact gatccatcgc aaccaaaatt    7380
tctgtttata gatcaagctg gtagattcca attactccac ctcttgcgct tctccatgac    7440
atgtaagtgc acgtggaaac catacccaaa ttgcctacag ctgcggagca tgagcctatg    7500
gcgatcagtc tggtcatgtt aaccagcctg tgctctgacg ttaatgcaga atagaaagcc    7560
gcggttgcaa tgcaaatgat gatgcctttg cagaaatggc ttgctcgctg actgatacca    7620
gtaacaactt tgcttggccg tctagcgctg ttgattgtat tcatcacaac ctcgtctccc    7680
tcctttgggt tgagctcttt ggatggcttt ccaaacgtta atagcgcgtt tttctccaca    7740
aagtattcgt atggacgcgc ttttgcgtgt attgcgtgag ctaccagcag cccaattggc    7800
gaagtcttga gccgcatcgc atagaataat tgattgcgca tttgatgcga tttttgagcg    7860
gctgtttcag gcgacatttc gcccgccctt atttgctcca ttatatcatc gacggcatgt    7920
ccaatagccc ggtgatagtc ttgtcgaata tggctgtcgt ggataaccca tcggcagcag    7980
atgataatga ttccgcagca cgcggccgca ggtagacgct tgcgagtgt gtgtgtatct    8040 aagaagtgca catcctgtat gtttgcagaa tgctgggtag ttttggttat ttgggcagtt    8100
tgagagcgga agacagtcct actgctgcgg aggagtctgg atcaagattg caacgtcgtt    8160
tatgtaataa ctataatgga gactggccgt cgtctgctgc cgctatttgg ttcggtgtca    8220
tgatctcgtg cctttgcgag gcgctcatct cgattgattg attgattggc ctgtctcgac    8280
atgtcgatac taaccttgcc gcggccgaac gattccattt ttgcttgctt ggtcaattgt    8340
actggtgtcg ccgggacctt tgtcagagcg agctgcccgt acctaccaac tacctagtag    8400
gtgccatcaa atgacgtgct gcaagctatc gcgaccagcc aggtcagccg cgtgtcacat    8460
gtaaggtcag agctaataag atgcgacatt ctgtgcattg ctagcaccgc caatactagc    8520
acgaaacggc tttggcacct cagtggcagg ccgaagttcg cgtgggatgg gatccattta    8580
ttaccctgca ttatacgggg agagctacag gtcttgagcg agtatcatcc aacgggcagt    8640
tgtttataag gatcaaagga caggttgtta ataccgaatt tacattaaga agtagaatgc    8700
aagatgagtt gtgaactgta atctcctgtg tttactgccc aaggtaggtg gcttagcatg    8760
ttagcagcaa tacattctta cctgtagcat ctggcgccgc tacctagtat caatatgatc    8820
caggcactaa ggcgtgttcc gcctcgacta cctcacagat gcatgatgca agttttgatg    8880
gaaaatgtcc gcgtctctgc tttcaacaaa ggccgccaac cgcccgctcc agccaaacaa    8940
gaacgcggct gcaataccca tcatctttca cagacaagcc gaatcagtcc gcgtcagttc    9000
agtttaaacg ctgtttcctg tgtgaaattg ttatccgctc acaattccac acaacatagg    9060
agccggaagc ataaagtgta aagcctgggg tgcctaatga gtgaggtaac tcacattaat    9120
tgcgttcgcg tcactgcccg ctttccagtc gggaaacctg tcgtgccagc tgcattaatg    9180
aatcggccaa cgcgcgggga gaggcggttt gcgtattggg cgctcttccg cttcctcgct    9240
cactgactcg ctgcgctcgg tcgttcggct gcggcgagcg gtatcagctc actcaaaggc    9300
ggtaatacgg ttatccacag aatcagggga taacgcagga aagaacatgt gagcaaaagg    9360
```

```
ccagcaaaag gccaggaacc gtaaaaaggc cgcgttgctg gcgttttttcc ataggctccg    9420
cccccctgac gagcatcaca aaaatcgacg ctcaagtcag aggtggcgaa acccgacagg    9480
actataaaga taccaggcgt ttccccctgg aagctccctc gtgcgctctc ctgttccgac    9540
cctgccgctt accggatacc tgtccgcctt tctcccttcg ggaagcgtgg cgctttctca    9600
tagctcacgc tgtaggtatc tcagttcggt gtaggtcgtt cgctccaagc tgggctgtgt    9660
gcacgaaccc cccgttcagc ccgaccgctg cgccttatcc ggtaactatc gtcttgagtc    9720
caacccggta agacacgact tatcgccact ggcagcagcc actggtaaca ggattagcag    9780
agcgaggtat gtaggcggtg ctacagagtt cttgaagtgg tggcctaact acggctacac    9840
tagaaggaca gtatttggta tctgcgctct gctgaagcca gttaccttcg gaaaaagagt    9900
tggtagctct tgatccggca aacaaaccac cgctggtagc ggtggttttt tgtttgcaa     9960
gcagcagatt acgcgcagaa aaaaggatc tcaagaagat cctttgatct tttctacggg    10020
gtctgacgct cagtggaacg aaaactcacg ttaagggatt ttggtcatga gattatcaaa    10080
aaggatcttc acctagatcc ttttaaatta aaaatgaagt tttaaatcaa tctaaagtat    10140
atatgagtaa acttggtctg acagttacca atgcttaatc agtgaggcac ctatctcagc    10200
gatctgtcta tttcgttcat ccatagttgc ctgactcccc gtcgtgtaga taactacgat    10260
acggggagggc ttaccatctg gccccagtgc tgcaatgata ccgcgagacc cacgctcacc    10320
ggctccagat ttatcagcaa taaaccagcc agccggaagg gccgagcgca gaagtggtcc    10380
tgcaacttta tccgcctcca tccagtctat taattgttgc cgggaagcta gagtaagtag    10440
ttcgccagtt aatagtttgc gcaacgttgt tgccattgct acaggcatcg tggtgtcacg    10500
ctcgtcgttt ggtatggctt cattcagctc cggttcccaa cgatcaaggc gagttacatg    10560
atccccccatg ttgtgcaaaa aagcggttag ctccttcggt cctccgatcg ttgtcagaag    10620
taagttggcc gcagtgttat cactcatggt tatggcagca ctgcataatt ctcttactgt    10680
catgccatcc gtaagatgct tttctgtgac tggtgagtac tcaaccaagt cattctgaga    10740
atagtgtatg cggcgaccga gttgctcttg cccggcgtca atacgggata ataccgcgcc    10800
acatagcaga actttaaaag tgctcatcat tggaaaacgt tcttcgggcc gaaaactctc    10860
aaggatctta ccgctgttga tccagttc gatgtaaccc actcgtgcac ccaactgatc    10920
ttcagcatct tttactttca ccagcgtttc tgggtgagca aaaacaggaa ggcaaaatgc    10980
cgcaaaaaag ggaataaggg cgacacggaa atgttgaata ctcatactct tcctttttca    11040
atattattga agcatttatc agggttattg tctcatgagc ggatacatat ttgaatgtat    11100
ttagaaaaat aaacaaatag gggttccgcg cacatttccc cgaaaagtgc cacctgaacg    11160
aagcatctgt gcttcatttt gtagaacaaa aatgcaacgc gagagcgcta attttttcaaa    11220
caaagaatct gagctgcatt tttacagaac agaaatgcaa cgcgaaagcg ctattttacc    11280
aacgaagaat ctgtgcttca tttttgtaaa acaaaaatgc aacgcgagag cgctaatttt    11340
tcaaacaaag aatctgagct gcattttttac agaacagaaa tgcaacgcga gagcgctatt    11400
ttaccaacaa agaatctata cttctttttt gttctacaaa aatgcatccc gagagcgcta    11460
tttttctaac aaagcatctt agattacttt ttttctcctt tgtgcgctct ataatgcagt    11520
ctcttgataa cttttttgcac tgtaggtccg ttaaggttag aagaaggcta ctttggtgtc    11580
tattttctct tccataaaaa aagcctgact ccacttcccg cgtttactga ttactagcga    11640
agctgcgggt gcatttttttc aagataaagg catccccgat tatattctat accgatgtgg    11700
attgcgcata cttttgtgaac agaaagtgat agcgttgatg attcttcatt ggtcagaaaa    11760
```

```
ttatgaacgg tttcttctat tttgtctcta tatactacgt ataggaaatg tttacatttt    11820
cgtattgttt tcgattcact ctatgaatag ttcttactac aattttttg tctaaagagt     11880 aatactagag ataaacataa aaaatgtaga ggtcgagttt agatgcaagt tcaaggagcg    11940
aaaggtggat gggtaggtta tatagggata tagcacagag atatatagca aagagatact   12000
tttgagcaat gtttgtggaa gcggtattcg caatatttta gtagctcgtt acagtccggt   12060 gcgttttttgg ttttttgaaa gtgcgtcttc agagcgcttt tggttttcaa aagcgctctg  12120
aagttcctat actttctaga gaataggaac ttcggaatag gaacttcaaa gcgtttccga   12180
aaacgagcgc ttccgaaaat gcaacgcgag ctgcgcacat acagctcact gttcacgtcg   12240
cacctatatc tgcgtgttgc ctgtatatat atatacatga gaagaacggc atagtgcgtg   12300
tttatgctta aatgcgtact tatatgcgtc tatttatgta ggatgaaagg tagtctagta   12360
cctcctgtga tattatccca ttccatgcgg ggtatcgtat gcttccttca gcactaccct   12420
ttagctgttc tatatgctgc cactcctcaa ttggattagt ctcatccttc aatgctatca   12480
tttcctttga tattggatca tactaagaaa ccattattat catgacatta acctataaaa   12540
ataggcgtat cacgaggccc tttcgtctcg cgcgtttcgg tgatgacggt gaaaacctct   12600
gacacatgca gctcccggag acggtcacag cttgtctgta agcggatgcc gggagcagac   12660
aagcccgtca gggcgcgtca gcgggtgttg gcgggtgtcg gggctggctt aactatgcgg   12720
catcagagca gattgtactg agagtgcacc ataccacagc ttttcaattc aattcatcat   12780
ttttttttta ttctttttttt tgatttcggt ttctttgaaa ttttttttgat tcggtaatct  12840 ccgaacagaa ggaagaacga aggaaggagc acagacttag attggtatat atacgcatat   12900
gtagtgttga agaaacatga aattgcccag tattcttaac ccaactgcac agaacaaaaa   12960
cctgcaggaa acgaagataa atcatgtcga aagctacata taaggaacgt gctgctactc   13020
atcctagtcc tgttgctgcc aagctattta atatcatgca cgaaaagcaa acaaacttgt   13080
gtgcttcatt ggatgttcgt accaccaagg aattactgga gttagttgaa gcattaggtc   13140
ccaaaatttg tttactaaaa acacatgtgg atatcttgac tgattttcc atggagggca    13200 cagttaagcc gctaaaggca ttatccgcca agtacaattt tttactcttc gaagacagaa   13260
aatttgctga cattggtaat acagtcaaat tgcagtactc tgcgggtgta tacagaatag   13320
cagaatgggc agacattacg aatgcacacg gtgtggtggg cccaggtatt gttagcggtt   13380
tgaagcaggc ggcagaagaa gtaacaaagg aacctagagg ccttttgatg ttagcagaat   13440
tgtcatgcaa gggctcccta tctactggag aatatactaa gggtactgtt gacattgcga   13500
agagcgacaa agattttgtt atcggcttta ttgctcaaag agacatgggt ggaagagatg   13560
aaggttacga ttggttgatt atgacacccg gtgtgggttt agatgacaag ggagacgcat   13620
tgggtcaaca gtatagaacc gtggatgatg tggtctctac aggatctgac attattattg   13680
ttggaagagg actatttgca aagggaaggg atgctaaggt agagggtgaa cgttacgaaa   13740
aagcaggctg ggaagcatat ttgagaagat gcggccagca aaactaaaaa actgtattat   13800
aagtaaatgc atgtatacta aactcacaaa ttagagcttc aatttaatta tatcagttat   13860
taccctatgc ggtgtgaaat accgcacaga tgcgtaagga gaaaataccg catcaggaaa   13920
ttgtaaacgt taatattttg ttaaaattcg cgttaaattt tgttaaatc agctcatttt    13980 ttaaccaata ggccgaaatc ggcaaaatcc cttataaatc aaaagaatag accgagatag   14040
ggttgagtgt tgttccagtt tggaacaaga gtccactatt aaagaacgtg gactccaacg   14100
```

-continued

```
tcaaagggcg aaaaaccgtc tatcagggcg atggcccact acgtgaacca tcaccctaat    14160 caagttttt ggggtcgagg tgccgtaaag cactaaatcg gaaccctaaa gggagccccc    14220
gatttagagc ttgacgggga aagccggcga acgtggcgag aaaggaaggg aagaaagcga    14280
aaggagcggg cgctagggcg ctggcaagtg tagcggtcac gctgcgcgta accaccacac    14340
ccgccgcgct taatgcgccg ctacagggcg cgtcgcgcca ttcgccattc aggctgcgca    14400
actgttggga agggcgatcg gtgcgggcct cttcgctatt acgccagctg gcgaaagggg    14460
gatgtgctgc aaggcgatta agttgggtaa cgccagggtt tcccagtca cgacg         14515
```

<210> SEQ ID NO 13
<211> LENGTH: 20
<212> TYPE: DNA
<213> ORGANISM: Artificial
<220> FEATURE:
<223> OTHER INFORMATION: 77579_5f primer

<400> SEQUENCE: 13
tcaggtcaac caccgaggac                                                20

<210> SEQ ID NO 14
<211> LENGTH: 20
<212> TYPE: DNA
<213> ORGANISM: Artificial
<220> FEATURE:
<223> OTHER INFORMATION: 77579_5r primer

<400> SEQUENCE: 14
tgaatgggat ggttcgattg                                                20

<210> SEQ ID NO 15
<211> LENGTH: 20
<212> TYPE: DNA
<213> ORGANISM: Artificial
<220> FEATURE:
<223> OTHER INFORMATION: 77579_3f primer

<400> SEQUENCE: 15
aggtagacgc tttgcgagtg                                                20

<210> SEQ ID NO 16
<211> LENGTH: 18
<212> TYPE: DNA
<213> ORGANISM: Artificial
<220> FEATURE:
<223> OTHER INFORMATION: 77579_3r primer

<400> SEQUENCE: 16
tgaactgacg cggactga                                                  18

<210> SEQ ID NO 17
<211> LENGTH: 59
<212> TYPE: DNA
<213> ORGANISM: Artificial
<220> FEATURE:
<223> OTHER INFORMATION: C017_gpdA_rec_for primer

<400> SEQUENCE: 17
cctctggcag caatcgaacc atcccattca ttaattaagc tccttattga agtcggagg     59

<210> SEQ ID NO 18
<211> LENGTH: 58
<212> TYPE: DNA
<213> ORGANISM: Artificial

```
<220> FEATURE:
<223> OTHER INFORMATION: C018_gpdA_rec_rev primer

<400> SEQUENCE: 18
atgaggaggg ttgatagttt gctgagcggc gggcagtcat gatgtctgct caagcggg      58

<210> SEQ ID NO 19
<211> LENGTH: 65
<212> TYPE: DNA
<213> ORGANISM: Artificial
<220> FEATURE:
<223> OTHER INFORMATION: C019_trpC_rec_for primer

<400> SEQUENCE: 19
taatccagtg gaatggtccc acccacaatt tgaaaagtaa gatccactta acgttactga    60
aatca                                                                65

<210> SEQ ID NO 20
<211> LENGTH: 66
<212> TYPE: DNA
<213> ORGANISM: Artificial
<220> FEATURE:
<223> OTHER INFORMATION: C020_trpC_rec_rev primer

<400> SEQUENCE: 20
aaggggaccg gccgctagtc tcaccgttat gcggccgctt aattaagagt ggagatgtgg    60
agtggg                                                               66

<210> SEQ ID NO 21
<211> LENGTH: 60
<212> TYPE: DNA
<213> ORGANISM: Artificial
<220> FEATURE:
<223> OTHER INFORMATION: C021_pep4_3frec_for primer

<400> SEQUENCE: 21
gataacccat cggcagcaga tgataatgat tccgcagcac gcggccgcag gtagacgctt    60

<210> SEQ ID NO 22
<211> LENGTH: 20
<212> TYPE: DNA
<213> ORGANISM: Artificial
<220> FEATURE:
<223> OTHER INFORMATION: C022_pep4_3f_rev primer

<400> SEQUENCE: 22
gaggtgccaa agccgtttcg                                                20

<210> SEQ ID NO 23
<211> LENGTH: 20
<212> TYPE: DNA
<213> ORGANISM: Artificial
<220> FEATURE:
<223> OTHER INFORMATION: T302_77579_5int primer

<400> SEQUENCE: 23
gattcatcac aggggcagtc                                                20

<210> SEQ ID NO 24
<211> LENGTH: 21
<212> TYPE: DNA
<213> ORGANISM: Artificial
<220> FEATURE:
<223> OTHER INFORMATION: T624_gpdA_seqR1 primer
```

-continued

<400> SEQUENCE: 24
ctccatattc tccgatgatg c                                              21

<210> SEQ ID NO 25
<211> LENGTH: 20
<212> TYPE: DNA
<213> ORGANISM: Artificial
<220> FEATURE:
<223> OTHER INFORMATION: T302_77579_5int primer

<400> SEQUENCE: 25
gattcatcac aggggcagtc                                                20

<210> SEQ ID NO 26
<211> LENGTH: 20
<212> TYPE: DNA
<213> ORGANISM: Artificial
<220> FEATURE:
<223> OTHER INFORMATION: C046_gpdA_rev primer

<400> SEQUENCE: 26
tatcctcttg acaccgctcc                                                20

<210> SEQ ID NO 27
<211> LENGTH: 19
<212> TYPE: DNA
<213> ORGANISM: Artificial
<220> FEATURE:
<223> OTHER INFORMATION: T415_77579_3screen primer

<400> SEQUENCE: 27
acgccgttgc tgagccttg                                                 19

<210> SEQ ID NO 28
<211> LENGTH: 20
<212> TYPE: DNA
<213> ORGANISM: Artificial
<220> FEATURE:
<223> OTHER INFORMATION: T1411_cbh2t_end_f primer

<400> SEQUENCE: 28
ccaatagccc ggtgatagtc                                                20

<210> SEQ ID NO 29
<211> LENGTH: 19
<212> TYPE: DNA
<213> ORGANISM: Artificial
<220> FEATURE:
<223> OTHER INFORMATION: T415_77579_3screen primer

<400> SEQUENCE: 29
acgccgttgc tgagccttg                                                 19

<210> SEQ ID NO 30
<211> LENGTH: 20
<212> TYPE: DNA
<213> ORGANISM: Artificial
<220> FEATURE:
<223> OTHER INFORMATION: T1404_cbh2term_for primer

<400> SEQUENCE: 30
ccgtctagcg ctgttgattg                                                20

<210> SEQ ID NO 31
<211> LENGTH: 20

```
<212> TYPE: DNA
<213> ORGANISM: Artificial
<220> FEATURE:
<223> OTHER INFORMATION: C009_Ibat_for1 primer

<400> SEQUENCE: 31
gatcaactta gcacgcattg                                            20

<210> SEQ ID NO 32
<211> LENGTH: 18
<212> TYPE: DNA
<213> ORGANISM: Artificial
<220> FEATURE:
<223> OTHER INFORMATION: C029_PKIp_rev primer

<400> SEQUENCE: 32
tttgctccaa ctcaggcg                                              18

<210> SEQ ID NO 33
<211> LENGTH: 1650
<212> TYPE: DNA
<213> ORGANISM: Artificial
<220> FEATURE:
<223> OTHER INFORMATION: polynucleotide sequence encoding the isoprene
      synthase optimized by codon optimization for yeast

<400> SEQUENCE: 33
atgacagcca gaagatcagc aaactatcaa ccttcatcat ggtcctacga cgaatacttg     60
gtcgatacaa caacaaacga ttctaaatta agaatacaag aagacgcaag aaagaaattg    120
gaagaagaag taagaaacgt tttggaagat ggtaaattag aaactttggc cttgttggaa    180
ttgatcgatg acattcaaag attgggttta ggttacaagt ttagagaatc aacatccacc    240
agtttagcca tgttgaagat gtcagttggt caagaagcat taattcttc tttgcattct    300 tgttcattgt actttagatt gttgagagaa cacggtttcg atataacacc agacgtattc    360
gaaaaattca aggatgaaaa cggtaaattc aaagattcta cgctaaagga tgttagaggt    420
ttgttaagtt tatatgaagc atcatttttg ggtttcgaag gtgaaaacat attggatgaa    480
gctagagagt ttactacaat gcacttgaat aacatcaagg ataaggtcaa cccaagaata    540
gcagaagaag taaaccatgc cttggaatta cctttgcaca aagagttga agattagaa     600 gctagaagaa gaatacaatc ctacagtaag tctggtgaaa ccaatcaagc attgttgact    660
ttggcaaaga tcgatttcaa cactgtccaa gcagtatacc aaagagattt gcaagacgtt    720
tcaaaatggt ggaaggacac agcttttagca gataaattgt ccttcgcaag agatagattg    780
atggaatctt tcttttgggc catcggcatg tcttacgatc cacaacactc aaagtccaga    840
gaagctgtca ctaagacttt taaattggtt accgtcttgg atgacgttta tgacgtctac    900
ggttctttag atgaattgga aaaattcact gctgcagccg aaagatggga tgtagacgct    960
ataaaagatt tgcctgacta catgaagttg tgttacttat cattgtttaa tactgttaac   1020
gatttggcat atgacacatt gaaagataag ggtgaaaccg tcattccaat aatgaaaaag   1080
gcttgggctg atttgttaaa agccttctta caagaagctc aatggatcta taataagtac   1140
acccctactt tcgatgaata cttaaataac gctagattca gtgtttctgg ttgcgtaatg   1200
ttggttcatt cttactttac cactcaaaac atcacaaagg aagcaatcca tagtttggaa   1260
aactaccacg acttgttaat atggcccttct atcgtcttca gattagctaa tgatttgtcc   1320
agttctaagg cagaaatcga aagaggtgaa actgccaatt ctatcacatg ttacatgaac   1380
gaaacaggtc aatcagaaga acaagctaga gaacatatct ccaaattgat cgatgaatgc   1440
```

| ttcaaaaaga tgaataagga aatgttggcc acatcaacct ccccatttga aaaatcattc | 1500 |
| atcgaaaccg ctattaactt agcaagaatt gccttgtgcc aatatcaata cggtgacgct | 1560 |
| cactctgatc ctgacgttag agcaagaaat agaatcgtaa gtgtcatcat taatccagtc | 1620 |
| gaatggtcac atccacaatt tgaaaagtaa | 1650 |

<210> SEQ ID NO 34
<211> LENGTH: 1578
<212> TYPE: DNA
<213> ORGANISM: Artificial
<220> FEATURE:
<223> OTHER INFORMATION: Truncated S. cerevisiae HMG1 ORF

<400> SEQUENCE: 34

| atggaccaat tggtgaaaac tgaagtcacc aagaagtctt ttactgctcc tgtacaaaag | 60 |
| gcttctacac cagttttaac caataaaaca gtcatttctg gatcgaaagt caaaagttta | 120 |
| tcatctgcgc aatcgagctc atcaggacct tcatcatcta gtgaggaaga tgattcccgc | 180 |
| gatattgaaa gcttggataa gaaaatacgt cctttagaag aattagaagc attattaagt | 240 |
| agtggaaata caaacaatt gaagaacaaa gaggtcgctg ccttggttat tcacggtaag | 300 |
| ttacctttgt acgctttgga gaaaaaatta ggtgatacta cgagagcggt tgcggtacgt | 360 |
| aggaaggctc tttcaattt ggcagaagct cctgtattag catctgatcg tttaccatat | 420 |
| aaaaattatg actacgaccg cgtatttggc gcttgttgtg aaaatgttat aggttacatg | 480 |
| cctttgcccg ttggtgttat aggccccttg gttatcgatg gtacatctta tcatatacca | 540 |
| atggcaacta cagagggttg tttggtagct tctgccatgc gtggctgtaa ggcaatcaat | 600 |
| gctggcggtg gtgcaacaac tgttttaact aaggatggta tgacaagagg cccagtagtc | 660 |
| cgtttcccaa cttttgaaaag atctggtgcc tgtaagatat ggttagactc agaagaggga | 720 |
| caaaacgcaa ttaaaaaagc ttttaactct acatcaagat tgcacgtct gcaacatatt | 780 |
| caaacttgtc tagcaggaga tttactcttc atgagattta gaacaactac tggtgacgca | 840 |
| atgggtatga atatgatttc taaaggtgtc gaatactcat taagcaaat ggtagaagag | 900 |
| tatggctggg aagatatgga ggttgtctcc gtttctggta actactgtac cgacaaaaaa | 960 |
| ccagctgcca tcaactggat cgaaggtcgt ggtaagagtg tcgtcgcaga agctactatt | 1020 |
| cctggtgatg ttgtcagaaa agtgttaaaa agtgatgttt ccgcattggt tgagttgaac | 1080 |
| attgctaaga atttggttgg atctgcaatg gctgggtctg ttggtggatt aacgcacat | 1140 |
| gcagctaatt tagtgacagc tgttttcttg gcattaggac aagatcctgc acaaaatgtt | 1200 |
| gaaagttcca actgtataac attgatgaaa gaagtggacg gtgatttgag aatttccgta | 1260 |
| tccatgccat ccatcgaagt aggtaccatc ggtggtggta ctgttctaga accacaaggt | 1320 |
| gccatgttgg acttattagg tgtaagaggc ccgcatgcta ccgctcctgg taccaacgca | 1380 |
| cgtcaattag caagaatagt tgcctgtgcc gtcttggcag gtgaattatc cttatgtgct | 1440 |
| gccctagcag ccggccattt ggttcaaagt catatgaccc acaacaggaa acctgctgaa | 1500 |
| ccaacaaaac ctaacaattt ggacgccact gatataaatc gtttgaaaga tgggtccgtc | 1560 |
| acctgcatta aatcctaa | 1578 |

<210> SEQ ID NO 35
<211> LENGTH: 867
<212> TYPE: DNA
<213> ORGANISM: Artificial
<220> FEATURE:

<223> OTHER INFORMATION: S. cerevisiae IDI1 ORF

<400> SEQUENCE: 35

```
atgactgccg acaacaatag tatgccccat ggtgcagtat ctagttacgc caaattagtg      60
caaaaccaaa cacctgaaga cattttggaa gagtttcctg aaattattcc attacaacaa     120
agacctaata cccgatctag tgagacgtca aatgacgaaa gcggagaaac atgtttttct     180
ggtcatgatg aggagcaaat taagttaatg aatgaaaatt gtattgtttt ggattgggac     240
gataatgcta ttggtgccgg taccaagaaa gtttgtcatt taatggaaaa tattgaaaag     300
ggtttactac atcgtgcatt ctccgtcttt attttcaatg aacaaggtga attactttta     360
caacaaagag ccactgaaaa aataactttc cctgatcttt ggactaacac atgctgctct     420
catccactat gtattgatga cgaattaggt ttgaagggta agctagacga taagattaag     480
ggcgctatta ctgcggcggt gagaaaacta gatcatgaat taggtattcc agaagatgaa     540
actaagacaa ggggtaagtt tcactttta aacagaatcc attacatggc accaagcaat     600
gaaccatggg gtgaacatga aattgattac atcctatttt ataagatcaa cgctaaagaa     660
aacttgactg tcaacccaaa cgtcaatgaa gttagagact tcaaatgggt ttcaccaaat     720
gatttgaaaa ctatgtttgc tgacccaagt tacaagttta cgccttggtt taagattatt     780
tgcgagaatt acttattcaa ctggtgggag caattagatg acctttctga agtggaaaat     840
gacaggcaaa ttcatagaat gctataa                                          867
```

<210> SEQ ID NO 36
<211> LENGTH: 1650
<212> TYPE: DNA
<213> ORGANISM: Artificial
<220> FEATURE:
<223> OTHER INFORMATION: I. batatas IspS with C-terminal strepII tag
      (underlined) for expression in T. reesei

<400> SEQUENCE: 36

```
atgactgccc gccgctcagc aaactatcaa ccctcctcat ggtcttacga cgaatacttg      60
gtggacacta ctactaacga cagcaaactg cgcattcaag aagacgctcg taaaaaattg     120
gaagaagaag tgcgtaacgt tctggaagat ggcaaattgg aaaccttagc actgttggaa     180
ctgattgatg acatccaacg gctgggcttg ggttataaat ttcgcgaaag caccagtact     240
tccctggcta tgttgaaaat gagtgtgggg caggaagcat ccaacagcag tttgcattct     300
tgttcattgt actttcgttt actgcgggaa cacggcttcg atattacccc cgacgtgttc     360
gaaaaattca agatgaaaaa cggtaaattt aagatagca tcgctaaaga tgttcgcggg     420
ttgttatcat tgtatgaagc aagcttttta gggttcgaag gcgaaaacat tttggacgaa     480
gcccgcgaat tcaccactat gcatctgaat aacatcaaag ataaagtgaa tcccgcgtatc     540
gcggaagaag ttaaccatgc tttagaactg ccgttgcacc gccgtgtgga acgtctggaa     600
gctcggcgcc gtattcaaag ctatagtaaa tccggtgaaa ccaatcaggc cctgctgacc     660
ctggctaaaa tcgattttaa caccgtgcag gcggtttacc aacgggatct gcaggacgtt     720
agtaaatggt ggaaagacac tgcattggcc gataaattat ccttcgcccg ggatcgcctg     780
atggaaagct ttttctgggc gattggtatg agctatgatc cccaacactc taaatcacgg     840
gaagccgtga ccaaaacttt taaactggtg accgttttgg atgacgtgta tgacgtttac     900
gggtctttag atgaactgga aaaattcacc gccgccgccg aacgttggga tgttgacgcg     960
attaaagatc tgccggacta catgaaattg tgttacttat ccctgtttaa taccgtgaac    1020
```

```
gatctggctt atgacacctt gaaagataaa ggcgaaactg ttattcctat catgaagaaa    1080
gcctgggctg atttactgaa agcatttctg caggaagccc aatggatcta caacaaatac    1140
accccaactt tcgatgaata cctgaataac gcccgtttca gcgtgagtgg ttgcgtgatg    1200
ttggttcata gctactttac cactcagaac atcaccaaag aagcgatcca ttctctggaa    1260
aactaccacg acttgttaat ttggcctagc atcgttttcc gtttagcaaa tgatctgtcc    1320
tcttcaaaag ccgaaattga acggggcgaa accgcgaata gcatcacttg ttatatgaac    1380
gaaaccggtc aaagtgaaga acaggcccgt gaacacattt ccaaactgat cgatgaatgc    1440
ttcaagaaaa tgaacaaaga atgctggcc acctccactt ctccgtttga aaaatccttc    1500
attgaaaccg cgatcaactt agcacgcatt gccctgtgcc agtatcaata cggcgatgcc    1560
catagcgatc cagatgttcg ggcacgcaac cgcattgtgt cagttatcat taatccagtg    1620
gaatggtccc acccacaatt tgaaaagtaa                                     1650
```

<210> SEQ ID NO 37
<211> LENGTH: 553
<212> TYPE: PRT
<213> ORGANISM: Quercus petraea

<400> SEQUENCE: 37

```
Met Thr Glu Arg Gln Ser Ala Asn Phe Gln Pro Ser Leu Trp Ser Tyr
1               5                   10                  15

Glu Tyr Ile Gln Ser Leu Lys Asn Gly Tyr Glu Ala Asp Leu Tyr Glu
            20                  25                  30

Asp Arg Ala Lys Lys Leu Gly Glu Glu Val Arg Arg Met Ile Asn Asn
        35                  40                  45

Lys Asp Thr Lys Leu Leu Thr Thr Leu Glu Leu Ile Asp Asp Ile Glu
    50                  55                  60

Arg Leu Gly Leu Gly Tyr Arg Phe Lys Glu Glu Ile Met Arg Ala Leu
65                  70                  75                  80

Asp Arg Phe Val Thr Leu Lys Gly Cys Glu Glu Phe Thr Asn Gly Ser
                85                  90                  95

Ile His Asp Thr Ala Leu Ser Phe Arg Leu Leu Arg Gln His Gly Phe
            100                 105                 110

Gly Val Ser Gln Asp Met Phe Asn Cys Phe Lys Asp Gln Lys Gly Asn
        115                 120                 125

Phe Lys Glu Cys Leu Ser Lys Asp Ile Lys Gly Leu Leu Ser Leu Tyr
    130                 135                 140

Glu Ala Ser Tyr Leu Gly Phe Glu Gly Glu Asn Leu Leu Asp Glu Ala
145                 150                 155                 160

Arg Glu Phe Thr Thr Met His Leu Lys Asp Leu Lys Gly Asp Val Ser
                165                 170                 175

Arg Thr Leu Lys Glu Glu Val Arg His Ser Leu Glu Met Pro Leu His
            180                 185                 190

Arg Arg Met Arg Arg Leu Glu Gln Arg Trp Tyr Ile Asp Ala Tyr Asn
        195                 200                 205

Met Lys Glu Ala His Asp Arg Lys Leu Leu Glu Leu Ala Lys Leu Asp
    210                 215                 220

Phe Asn Ile Val Gln Ser Val His Gln Arg Asp Leu Lys Asp Met Ser
225                 230                 235                 240

Arg Trp Trp Gln Glu Met Gly Leu Gly Asn Lys Leu Ser Phe Ala Arg
                245                 250                 255

Asp Arg Leu Met Glu Cys Phe Phe Phe Ser Val Gly Met Ala Phe Glu
```

```
            260                 265                 270
Pro Gln Phe Ser Asn Ser Arg Lys Ala Val Thr Lys Met Phe Ser Phe
            275                 280                 285

Ile Thr Val Ile Asp Asp Ile Tyr Asp Val Tyr Ala Thr Leu Glu Glu
            290                 295                 300

Leu Glu Met Phe Thr Asp Ile Val Gln Arg Trp Asp Val Lys Ala Val
305                 310                 315                 320

Lys Asp Leu Pro Glu Tyr Met Lys Leu Cys Phe Leu Ala Leu Phe Asn
                    325                 330                 335

Thr Val Asn Glu Met Val Tyr Asp Thr Leu Lys Glu Gln Gly Val Asp
                340                 345                 350

Ile Leu Pro Tyr Leu Thr Lys Ala Trp Gly Asp Ile Cys Lys Ala Phe
            355                 360                 365

Leu Gln Glu Thr Lys Trp Arg Tyr Tyr Lys Arg Thr Pro Ser Ser Glu
        370                 375                 380

Asp Tyr Leu Asp Asn Ala Trp Ile Ser Val Ser Gly Ala Leu Leu Leu
385                 390                 395                 400

Ile His Ala Tyr Phe Leu Met Ser Pro Ser Ile Thr Asp Arg Ala Leu
                    405                 410                 415

Lys Gly Leu Glu Asp Tyr His Asn Ile Leu Arg Trp Pro Ser Ile Ile
                420                 425                 430

Phe Arg Leu Thr Asn Asp Leu Gly Thr Ser Thr Ala Glu Leu Glu Arg
            435                 440                 445

Gly Glu Thr Ala Asn Ser Ile Leu Cys Tyr Met Arg Glu Thr Ser Arg
450                 455                 460

Ser Glu Asp Phe Ala Arg Glu His Ile Ser Asn Leu Ile Asp Lys Thr
465                 470                 475                 480

Trp Lys Lys Met Asn Lys Asp Arg Phe Ser Asp Ser Pro Phe Glu Glu
                    485                 490                 495

Pro Phe Leu Glu Thr Ala Ile Asn Leu Ala Arg Ile Ser His Cys Ile
                500                 505                 510

Tyr Gln His Gly Asp Gly His Gly Ala Pro Asp Thr Arg Thr Lys Asp
            515                 520                 525

Arg Val Leu Ser Leu Ile Ile Glu Pro Ile Pro Cys Tyr Asp Pro Ser
        530                 535                 540

Thr Asn Phe His Ser Gln Ile His Leu
545                 550

<210> SEQ ID NO 38
<211> LENGTH: 583
<212> TYPE: PRT
<213> ORGANISM: Melaleuca alternifolia

<400> SEQUENCE: 38

Met Ala Leu Arg Leu Leu Ser Thr Pro His Leu Pro Gln Leu Cys Ser
1               5                   10                  15

Arg Arg Val Ser Gly Arg Val His Cys Ser Ala Ser Thr Gln Val Ser
                20                  25                  30

Asp Ala Gln Gly Gly Arg Arg Ser Ala Asn Tyr Gln Pro Ser Val Trp
            35                  40                  45

Thr Tyr Asn Tyr Leu Gln Ser Leu Val Ala Asp Asp Ile Arg Arg Ser
        50                  55                  60

Arg Arg Glu Val Glu Gln Glu Arg Glu Lys Ala Gln Ile Leu Glu Glu
65                  70                  75                  80
```

Asp Val Arg Gly Ala Leu Asn Asp Gly Asn Ala Glu Pro Met Ala Ile
                    85                  90                  95

Phe Ala Leu Val Asp Asp Ile Gln Arg Leu Gly Leu Gly Arg Tyr Phe
                100                 105                 110

Glu Glu Asp Ile Ser Lys Ala Leu Arg Arg Cys Leu Ser Gln Tyr Ala
                115                 120                 125

Val Thr Gly Ser Leu Gln Lys Ser Leu His Gly Thr Ala Leu Ser Phe
            130                 135                 140

Arg Val Leu Arg Gln His Gly Phe Glu Val Ser Gln Asp Val Phe Lys
145                 150                 155                 160

Ile Phe Met Asp Glu Ser Gly Ser Phe Met Lys Thr Leu Gly Gly Asp
                165                 170                 175

Val Gln Gly Met Leu Ser Leu Tyr Glu Ala Ser His Leu Ala Phe Glu
            180                 185                 190

Glu Glu Asp Ile Leu His Lys Ala Lys Thr Phe Ala Ile Lys His Leu
            195                 200                 205

Glu Asn Leu Asn His Asp Ile Asp Gln Asp Leu Gln Asp His Val Asn
        210                 215                 220

His Glu Leu Glu Leu Pro Leu His Arg Arg Met Pro Leu Leu Glu Ala
225                 230                 235                 240

Arg Arg Phe Ile Glu Ala Tyr Ser Arg Ser Asn Val Asn Pro Arg
                245                 250                 255

Ile Leu Glu Leu Ala Val Met Lys Phe Asn Ser Ser Gln Leu Thr Leu
                260                 265                 270

Gln Arg Asp Leu Gln Asp Met Leu Gly Trp Trp Asn Asn Val Gly Leu
            275                 280                 285

Ala Lys Arg Leu Ser Phe Ala Arg Asp Arg Leu Met Glu Cys Phe Phe
        290                 295                 300

Trp Ala Val Gly Ile Ala Arg Glu Pro Ala Leu Ser Asn Cys Arg Lys
305                 310                 315                 320

Gly Val Thr Lys Ala Phe Ser Leu Ile Leu Val Leu Asp Asp Val Tyr
                325                 330                 335

Asp Val Phe Gly Thr Leu Asp Glu Leu Glu Leu Phe Thr Asp Ala Val
                340                 345                 350

Arg Arg Trp His Glu Asp Ala Val Glu Asn Leu Pro Gly Tyr Met Lys
            355                 360                 365

Leu Cys Phe Leu Ala Leu Tyr Asn Ser Val Asn Asp Met Ala Tyr Glu
        370                 375                 380

Thr Leu Lys Glu Thr Gly Glu Asn Val Thr Pro Tyr Leu Thr Lys Val
385                 390                 395                 400

Trp Tyr Asp Leu Cys Lys Ala Phe Leu Gln Glu Ala Lys Trp Ser Tyr
                405                 410                 415

Asn Lys Ile Thr Pro Gly Val Glu Glu Tyr Leu Asn Asn Gly Trp Val
                420                 425                 430

Ser Ser Ser Gly Gln Val Met Leu Thr His Ala Tyr Phe Leu Ser Ser
            435                 440                 445

Pro Ser Leu Arg Lys Glu Glu Leu Glu Ser Leu Glu His Tyr His Asp
        450                 455                 460

Leu Leu Arg Leu Pro Ser Leu Ile Phe Arg Leu Thr Asn Asp Leu Ala
465                 470                 475                 480

Thr Ser Ser Ala Glu Leu Gly Arg Gly Glu Thr Thr Asn Ser Ile Leu
                485                 490                 495

Cys Tyr Met Arg Glu Lys Gly Phe Ser Glu Ser Glu Ala Arg Lys Gln

```
                    500                 505                 510
Val Ile Glu Gln Ile Asp Thr Ala Trp Arg Gln Met Asn Lys Tyr Met
                515                 520                 525

Val Asp His Ser Thr Phe Asn Arg Ser Phe Met Gln Met Thr Tyr Asn
            530                 535                 540

Leu Ala Arg Met Ala His Cys Val Tyr Gln Asp Gly Asp Ala Ile Gly
545                 550                 555                 560

Ala Pro Asp Asp Gln Ser Trp Asn Arg Val His Ser Leu Ile Ile Lys
                565                 570                 575

Pro Val Ser Leu Ala Pro Cys
            580

<210> SEQ ID NO 39
<211> LENGTH: 582
<212> TYPE: PRT
<213> ORGANISM: Eucalyptus globulus

<400> SEQUENCE: 39

Met Ala Leu Arg Leu Phe Thr Pro His Leu Pro Val Leu Ser Ser
1               5                   10                  15

Arg Arg Ala Asn Gly Arg Val Arg Cys Ser Ala Ser Thr Gln Ile Ser
                20                  25                  30

Asp Pro Gln Glu Gly Arg Arg Ser Ala Asn Tyr Gln Pro Ser Val Trp
            35                  40                  45

Thr Tyr Asn Tyr Leu Gln Ser Ile Val Ala Gly Glu Gly Arg Gln Ser
        50                  55                  60

Arg Arg Glu Val Glu Gln Lys Glu Lys Val Gln Ile Leu Glu Glu
65                  70                  75                  80

Glu Val Arg Gly Ala Leu Asn Asp Glu Lys Ala Glu Thr Phe Thr Ile
                85                  90                  95

Phe Ala Thr Val Asp Asp Ile Gln Arg Leu Gly Leu Gly Asp His Phe
            100                 105                 110

Glu Glu Asp Ile Ser Asn Ala Leu Arg Arg Cys Val Ser Lys Gly Ala
        115                 120                 125

Val Phe Met Ser Leu Gln Lys Ser Leu His Gly Thr Ala Leu Gly Phe
    130                 135                 140

Arg Leu Leu Arg Gln His Gly Tyr Glu Val Ser Gln Asp Val Phe Lys
145                 150                 155                 160

Ile Phe Leu Asp Glu Ser Gly Ser Phe Val Lys Thr Leu Gly Gly Asp
                165                 170                 175

Val Gln Gly Val Leu Ser Leu Tyr Glu Ala Ser His Leu Ala Phe Glu
            180                 185                 190

Glu Glu His Ile Leu His Lys Ala Arg Ser Phe Ala Ile Lys His Leu
        195                 200                 205

Glu Asn Leu Asn Ser Asp Val Asp Lys Asp Leu Gln Asp Gln Val Lys
    210                 215                 220

His Glu Leu Glu Leu Pro Leu His Arg Arg Met Pro Leu Leu Glu Ala
225                 230                 235                 240

Arg Arg Ser Ile Glu Ala Tyr Ser Arg Arg Gly Tyr Thr Asn Pro Gln
                245                 250                 255

Ile Leu Glu Leu Ala Leu Thr Asp Phe Asn Val Ser Gln Ser Tyr Leu
            260                 265                 270

Gln Arg Asp Leu Gln Glu Met Leu Gly Trp Trp Asn Asn Thr Gly Leu
        275                 280                 285
```

```
Ala Lys Arg Leu Ser Phe Ala Arg Asp Arg Leu Ile Glu Cys Phe Phe
    290                 295                 300

Trp Ala Val Gly Ile Ala His Glu Pro Ser Leu Ser Ile Cys Arg Lys
305                 310                 315                 320

Ala Val Thr Lys Ala Phe Ala Leu Ile Leu Val Leu Asp Asp Val Tyr
                325                 330                 335

Asp Val Phe Gly Thr Leu Glu Glu Leu Glu Leu Phe Thr Asp Ala Val
            340                 345                 350

Arg Arg Trp Asp Leu Asn Ala Val Glu Asp Leu Pro Val Tyr Met Lys
        355                 360                 365

Leu Cys Tyr Leu Ala Leu Tyr Asn Ser Val Asn Glu Met Ala Tyr Glu
    370                 375                 380

Thr Leu Lys Glu Lys Gly Glu Asn Val Ile Pro Tyr Leu Ala Lys Ala
385                 390                 395                 400

Trp Tyr Asp Leu Cys Lys Ala Phe Leu Gln Glu Ala Lys Trp Ser Asn
                405                 410                 415

Ser Arg Ile Ile Pro Gly Val Glu Glu Tyr Leu Asn Asn Gly Trp Val
            420                 425                 430

Ser Ser Ser Gly Ser Val Met Leu Ile His Ala Tyr Phe Leu Ala Ser
        435                 440                 445

Pro Ser Ile Arg Lys Glu Glu Leu Glu Ser Leu Glu His Tyr His Asp
    450                 455                 460

Leu Leu Arg Leu Pro Ser Leu Ile Phe Arg Leu Thr Asn Asp Ile Ala
465                 470                 475                 480

Ser Ser Ser Ala Glu Leu Glu Arg Gly Glu Thr Thr Asn Ser Ile Arg
                485                 490                 495

Cys Phe Met Gln Glu Lys Gly Ile Ser Glu Leu Glu Ala Arg Glu Cys
            500                 505                 510

Val Lys Glu Glu Ile Asp Thr Ala Trp Lys Lys Met Asn Lys Tyr Met
        515                 520                 525

Val Asp Arg Ser Thr Phe Asn Gln Ser Phe Val Arg Met Thr Tyr Asn
    530                 535                 540

Leu Ala Arg Met Ala His Cys Val Tyr Gln Asp Gly Asp Ala Ile Gly
545                 550                 555                 560

Ser Pro Asp Asp Leu Ser Trp Asn Arg Val His Ser Leu Ile Ile Lys
                565                 570                 575

Pro Ile Ser Pro Ala Ala
            580

<210> SEQ ID NO 40
<211> LENGTH: 595
<212> TYPE: PRT
<213> ORGANISM: Populus alba

<400> SEQUENCE: 40

Met Ala Thr Glu Leu Leu Cys Leu His Arg Pro Ile Ser Leu Thr His
1               5                   10                  15

Lys Leu Phe Arg Asn Pro Leu Pro Lys Val Ile Gln Ala Thr Pro Leu
            20                  25                  30

Thr Leu Lys Leu Arg Cys Ser Val Ser Thr Glu Asn Val Ser Phe Thr
        35                  40                  45

Glu Thr Glu Thr Glu Ala Arg Arg Ser Ala Asn Tyr Glu Pro Asn Ser
    50                  55                  60

Trp Asp Tyr Asp Tyr Leu Leu Ser Ser Asp Thr Asp Glu Ser Ile Glu
65                  70                  75                  80
```

```
Val Tyr Lys Asp Lys Ala Lys Lys Leu Glu Ala Glu Val Arg Arg Glu
                85                  90                  95
Ile Asn Asn Glu Lys Ala Glu Phe Leu Thr Leu Leu Glu Leu Ile Asp
               100                 105                 110
Asn Val Gln Arg Leu Gly Leu Gly Tyr Arg Phe Glu Ser Asp Ile Arg
           115                 120                 125
Gly Ala Leu Asp Arg Phe Val Ser Ser Gly Phe Asp Ala Val Thr
130                 135                 140
Lys Thr Ser Leu His Gly Thr Ala Leu Ser Phe Arg Leu Leu Arg Gln
145                 150                 155                 160
His Gly Phe Glu Val Ser Gln Glu Ala Phe Ser Gly Phe Lys Asp Gln
               165                 170                 175
Asn Gly Asn Phe Leu Glu Asn Leu Lys Glu Asp Ile Lys Ala Ile Leu
           180                 185                 190
Ser Leu Tyr Glu Ala Ser Phe Leu Ala Leu Glu Gly Glu Asn Ile Leu
       195                 200                 205
Asp Glu Ala Lys Val Phe Ala Ile Ser His Leu Lys Glu Leu Ser Glu
   210                 215                 220
Glu Lys Ile Gly Lys Glu Leu Ala Glu Gln Val Asn His Ala Leu Glu
225                 230                 235                 240
Leu Pro Leu His Arg Arg Thr Gln Arg Leu Glu Ala Val Trp Ser Ile
               245                 250                 255
Glu Ala Tyr Arg Lys Lys Glu Asp Ala Asn Gln Val Leu Leu Glu Leu
           260                 265                 270
Ala Ile Leu Asp Tyr Asn Met Ile Gln Ser Val Tyr Gln Arg Asp Leu
       275                 280                 285
Arg Glu Thr Ser Arg Trp Trp Arg Arg Val Gly Leu Ala Thr Lys Leu
   290                 295                 300
His Phe Ala Arg Asp Arg Leu Ile Glu Ser Phe Tyr Trp Ala Val Gly
305                 310                 315                 320
Val Ala Phe Glu Pro Gln Tyr Ser Asp Cys Arg Asn Ser Val Ala Lys
               325                 330                 335
Met Phe Ser Phe Val Thr Ile Ile Asp Asp Ile Tyr Asp Val Tyr Gly
           340                 345                 350
Thr Leu Asp Glu Leu Glu Leu Phe Thr Asp Ala Val Glu Arg Trp Asp
       355                 360                 365
Val Asn Ala Ile Asn Asp Leu Pro Asp Tyr Met Lys Leu Cys Phe Leu
   370                 375                 380
Ala Leu Tyr Asn Thr Ile Asn Glu Ile Ala Tyr Asp Asn Leu Lys Asp
385                 390                 395                 400
Lys Gly Glu Asn Ile Leu Pro Tyr Leu Thr Lys Ala Trp Ala Asp Leu
               405                 410                 415
Cys Asn Ala Phe Leu Gln Glu Ala Lys Trp Leu Tyr Asn Lys Ser Thr
           420                 425                 430
Pro Thr Phe Asp Asp Tyr Phe Gly Asn Ala Trp Lys Ser Ser Ser Gly
       435                 440                 445
Pro Leu Gln Leu Val Phe Ala Tyr Phe Ala Val Val Gln Asn Ile Lys
   450                 455                 460
Lys Glu Glu Ile Glu Asn Leu Gln Lys Tyr His Asp Thr Ile Ser Arg
465                 470                 475                 480
Pro Ser His Ile Phe Arg Leu Cys Asn Asp Leu Ala Ser Ala Ser Ala
               485                 490                 495
```

```
Glu Ile Ala Arg Gly Glu Thr Ala Asn Ser Val Ser Cys Tyr Met Arg
                500                 505                 510

Thr Lys Gly Ile Ser Glu Glu Leu Ala Thr Glu Ser Val Met Asn Leu
            515                 520                 525

Ile Asp Glu Thr Trp Lys Lys Met Asn Lys Glu Lys Leu Gly Gly Ser
        530                 535                 540

Leu Phe Ala Lys Pro Phe Val Glu Thr Ala Ile Asn Leu Ala Arg Gln
545                 550                 555                 560

Ser His Cys Thr Tyr His Asn Gly Asp Ala His Thr Ser Pro Asp Glu
                565                 570                 575

Leu Thr Arg Lys Arg Val Leu Ser Val Ile Thr Glu Pro Ile Leu Pro
            580                 585                 590

Phe Glu Arg
        595

<210> SEQ ID NO 41
<211> LENGTH: 595
<212> TYPE: PRT
<213> ORGANISM: Populus canescens

<400> SEQUENCE: 41

Met Ala Thr Glu Leu Leu Cys Leu His Arg Pro Ile Ser Leu Thr His
1               5                   10                  15

Lys Leu Phe Arg Asn Pro Leu Pro Lys Val Ile Gln Ala Thr Pro Leu
            20                  25                  30

Thr Leu Lys Leu Arg Cys Ser Val Ser Thr Glu Asn Val Ser Phe Thr
        35                  40                  45

Glu Thr Glu Thr Glu Ala Arg Arg Ser Ala Asn Tyr Glu Pro Asn Ser
    50                  55                  60

Trp Asp Tyr Asp Phe Leu Leu Ser Ser Asp Thr Asp Glu Ser Ile Glu
65                  70                  75                  80

Val Tyr Lys Asp Lys Ala Lys Lys Leu Glu Ala Glu Val Arg Arg Glu
                85                  90                  95

Ile Asn Asn Glu Lys Ala Glu Phe Leu Thr Leu Leu Glu Leu Ile Asp
            100                 105                 110

Asn Val Gln Arg Leu Gly Leu Gly Tyr Arg Phe Glu Ser Asp Ile Arg
        115                 120                 125

Arg Ala Leu Asp Arg Phe Val Ser Ser Gly Gly Phe Asp Gly Val Thr
    130                 135                 140

Lys Thr Ser Leu His Ala Thr Ala Leu Ser Phe Arg Leu Leu Arg Gln
145                 150                 155                 160

His Gly Phe Glu Val Ser Gln Glu Ala Phe Ser Gly Phe Lys Asp Gln
                165                 170                 175

Asn Gly Asn Phe Leu Glu Asn Leu Lys Glu Asp Thr Lys Ala Ile Leu
            180                 185                 190

Ser Leu Tyr Glu Ala Ser Phe Leu Ala Leu Glu Gly Glu Asn Ile Leu
        195                 200                 205

Asp Glu Ala Arg Val Phe Ala Ile Ser His Leu Lys Glu Leu Ser Glu
    210                 215                 220

Glu Lys Ile Gly Lys Glu Leu Ala Glu Gln Val Asn His Ala Leu Glu
225                 230                 235                 240

Leu Pro Leu His Arg Arg Thr Gln Arg Leu Glu Ala Val Trp Ser Ile
                245                 250                 255

Glu Ala Tyr Arg Lys Lys Glu Asp Ala Asn Gln Val Leu Leu Glu Leu
            260                 265                 270
```

```
Ala Ile Leu Asp Tyr Asn Met Ile Gln Ser Val Tyr Gln Arg Asp Leu
            275                 280                 285

Arg Glu Thr Ser Arg Trp Trp Arg Val Gly Leu Ala Thr Lys Leu
290                 295                 300

His Phe Ala Lys Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
            325                 330                 335

Met Phe Ser Phe Val Thr Ile Ile Asp Asp Ile Tyr Asp Val Tyr Gly
            340                 345                 350

Thr Leu Asp Glu Leu Glu Leu Phe Thr Asp Ala Val Glu Arg Trp Asp
            355                 360                 365

Val Asn Ala Ile Asn Asp Leu Pro Asp Tyr Met Lys Leu Cys Phe Leu
370                 375                 380

Ala Leu Tyr Asn Thr Ile Asn Glu Ile Ala Tyr Asp Asn Leu Lys Asp
385                 390                 395                 400

Lys Gly Glu Asn Ile Leu Pro Tyr Leu Thr Lys Ala Trp Ala Asp Leu
                405                 410                 415

Cys Asn Ala Phe Leu Gln Glu Ala Lys Trp Leu Tyr Asn Lys Ser Thr
                420                 425                 430

Pro Thr Phe Asp Asp Tyr Phe Gly Asn Ala Trp Lys Ser Ser Ser Gly
            435                 440                 445

Pro Leu Gln Leu Ile Phe Ala Tyr Phe Ala Val Val Gln Asn Ile Lys
            450                 455                 460

Lys Glu Glu Ile Glu Asn Leu Gln Lys Tyr His Asp Ile Ile Ser Arg
465                 470                 475                 480

Pro Ser His Ile Phe Arg Leu Cys Asn Asp Leu Ala Ser Ala Ser Ala
                485                 490                 495

Glu Ile Ala Arg Gly Glu Thr Ala Asn Ser Val Ser Cys Tyr Met Arg
                500                 505                 510

Thr Lys Gly Ile Ser Glu Glu Leu Ala Thr Glu Ser Val Met Asn Leu
                515                 520                 525

Ile Asp Glu Thr Cys Lys Lys Met Asn Lys Glu Lys Leu Gly Gly Ser
            530                 535                 540

Leu Phe Ala Lys Pro Phe Val Glu Thr Ala Ile Asn Leu Ala Arg Gln
545                 550                 555                 560

Ser His Cys Thr Tyr His Asn Gly Asp Ala His Thr Ser Pro Asp Glu
                565                 570                 575

Leu Thr Arg Lys Arg Val Leu Ser Val Ile Thr Glu Pro Ile Leu Pro
                580                 585                 590

Phe Glu Arg
            595

<210> SEQ ID NO 42
<211> LENGTH: 595
<212> TYPE: PRT
<213> ORGANISM: Salix sp.

<400> SEQUENCE: 42

Met Ala Thr Glu Leu Leu Cys Leu His Arg Pro Ile Ser Leu Thr Pro
1               5                   10                  15

Lys Leu Phe Arg Asn Pro Leu Pro Lys Val Ile Leu Ala Thr Pro Leu
                20                  25                  30

Thr Leu Lys Leu Arg Cys Ser Val Ser Thr Glu Asn Val Ser Phe Thr
```

-continued

```
                35                  40                  45
Glu Thr Glu Thr Glu Thr Arg Arg Ser Ala Asn Tyr Glu Pro Asn Ser
 50                  55                  60

Trp Asp Tyr Asp Tyr Leu Leu Ser Ser Asp Thr Asp Glu Ser Ile Glu
 65                  70                  75                  80

Val Tyr Lys Asp Lys Ala Lys Lys Leu Glu Ala Glu Val Arg Arg Glu
                 85                  90                  95

Ile Asn Asn Glu Lys Ala Glu Phe Leu Thr Leu Leu Glu Leu Ile Asp
                100                 105                 110

Asn Val Gln Arg Leu Gly Leu Gly Tyr Arg Phe Glu Ser Asp Ile Arg
                115                 120                 125

Arg Ala Leu Asp Arg Phe Val Ser Ser Gly Gly Phe Asp Ala Val Thr
                130                 135                 140

Lys Thr Ser Leu His Ala Thr Ala Leu Ser Phe Arg Phe Leu Arg Gln
145                 150                 155                 160

His Gly Phe Glu Val Ser Gln Glu Ala Phe Gly Gly Phe Lys Asp Gln
                165                 170                 175

Asn Gly Asn Phe Leu Glu Asn Leu Lys Glu Asp Ile Lys Ala Ile Leu
                180                 185                 190

Ser Leu Tyr Glu Ala Ser Phe Leu Ala Leu Glu Gly Glu Asn Ile Leu
                195                 200                 205

Asp Glu Ala Lys Val Phe Ala Ile Ser His Leu Lys Glu Leu Ser Glu
                210                 215                 220

Glu Lys Ile Gly Lys Asp Leu Ala Glu Gln Val Asn His Ala Leu Glu
225                 230                 235                 240

Leu Pro Leu His Arg Arg Thr Gln Arg Leu Glu Ala Val Trp Ser Ile
                245                 250                 255

Glu Ala Tyr Arg Lys Lys Glu Asp Ala Asn Gln Val Leu Leu Glu Leu
                260                 265                 270

Ala Ile Leu Asp Tyr Asn Met Ile Gln Ser Val Tyr Gln Arg Asp Leu
                275                 280                 285

Arg Glu Thr Ser Arg Trp Trp Arg Arg Val Gly Leu Ala Thr Lys Leu
                290                 295                 300

His Phe Ala Arg Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
                325                 330                 335

Met Phe Ser Phe Val Thr Ile Ile Asp Asp Ile Tyr Asp Val Tyr Gly
                340                 345                 350

Thr Leu Asp Glu Leu Glu Leu Phe Thr Asp Ala Val Glu Arg Trp Asp
                355                 360                 365

Val Asn Ala Ile Asn Asp Leu Pro Asp Tyr Met Lys Leu Cys Phe Leu
                370                 375                 380

Ala Leu Tyr Asn Thr Ile Asn Glu Ile Ala Tyr Asp Asn Leu Lys Glu
385                 390                 395                 400

Lys Gly Glu Asn Ile Leu Pro Tyr Leu Thr Lys Ala Trp Ala Asp Leu
                405                 410                 415

Cys Asn Ala Phe Leu Gln Glu Ala Lys Trp Leu Tyr Asn Lys Ser Thr
                420                 425                 430

Pro Thr Phe Asp Asp Tyr Phe Gly Asn Ala Trp Lys Ser Ser Ser Gly
                435                 440                 445

Pro Leu Gln Leu Val Phe Ala Tyr Phe Ala Val Val Gln Asn Ile Lys
                450                 455                 460
```

```
Lys Glu Glu Ile Glu Asn Leu Gln Lys Tyr His Asp Ile Ile Ser Arg
465                 470                 475                 480

Pro Ser His Ile Phe Arg Leu Cys Asn Asp Leu Ala Ser Ala Ser Ala
            485                 490                 495

Glu Ile Ala Arg Gly Glu Thr Ala Asn Ser Val Ser Cys Tyr Met Arg
        500                 505                 510

Thr Lys Gly Ile Ser Glu Glu Leu Ala Thr Glu Ser Val Met Asn Leu
            515                 520                 525

Ile Asp Glu Thr Trp Lys Lys Met Asn Lys Glu Lys Leu Gly Gly Ser
530                 535                 540

Leu Phe Pro Lys Pro Phe Val Glu Thr Ala Ile Asn Leu Ala Arg Gln
545                 550                 555                 560

Ser His Cys Thr Tyr His Asn Gly Asp Ala His Thr Ser Pro Asp Glu
            565                 570                 575

Leu Thr Arg Lys Arg Val Leu Ser Val Ile Thr Glu Pro Ile Leu Pro
            580                 585                 590

Phe Glu Arg
        595

<210> SEQ ID NO 43
<211> LENGTH: 541
<212> TYPE: PRT
<213> ORGANISM: Wisteria sp.

<400> SEQUENCE: 43

Arg Arg Ser Gly Asn Tyr Gln Pro Asn Leu Trp Asn Phe Asp Phe Leu
1               5                   10                  15

Gln Ser Gln Lys Asn Asp Leu Lys Glu Glu Met Leu Gln Glu Arg Ala
            20                  25                  30

Gly Lys Leu Glu Glu Glu Val Arg Gly Leu Ile Asn Glu Val Asp Thr
        35                  40                  45

Glu Pro Leu Ser Leu Leu Glu Leu Ile Asp Asn Val Glu Arg Leu Gly
    50                  55                  60

Leu Thr Tyr Lys Phe Gln Glu Asp Ile Asn Lys Ala Leu Gly Arg Ile
65                  70                  75                  80

Val Ser Ser Asp Ile Asn Lys Ser Gly Leu His Ala Ala Leu Thr
                85                  90                  95

Phe Arg Leu Leu Arg Gln His Gly Phe Gln Ile Ser Gln Asp Val Phe
            100                 105                 110

Glu Lys Phe Lys Asp Lys Glu Gly Arg Phe Ser Ala Glu Ile Lys Gly
        115                 120                 125

Asp Val Gln Gly Leu Leu Ser Leu Tyr Glu Ala Ser Tyr Leu Gly Phe
    130                 135                 140

Glu Gly Glu Asn Val Leu Glu Glu Ala Arg Ala Phe Ser Thr Thr His
145                 150                 155                 160

Leu Arg Asn Ile Lys Gln Gly Val Ser Thr Lys Met Ala Glu Gln Ile
            165                 170                 175

Ser His Ala Leu Glu Leu Pro Tyr His Arg Leu Gln Arg Leu Glu
            180                 185                 190

Ala Arg Arg Phe Ile Asp Lys Phe Glu Ile Lys Glu Pro Gln Asp Arg
        195                 200                 205

Leu Leu Leu Glu Leu Ala Lys Leu Asp Phe Asn Met Val Gln Thr Leu
    210                 215                 220

Gln Gln Lys Glu Leu Arg Asp Leu Ser Arg Trp Trp Lys Glu Ile Gly
```

```
            225                 230                 235                 240

Leu Ala Arg Lys Met Glu Phe Val Arg Asp Arg Leu Met Glu Val Tyr
            245                 250                 255

Phe Trp Ala Val Gly Met Ala Pro Asp Pro Leu Leu Ser Asp Cys Arg
            260                 265                 270

Lys Ala Ile Ala Lys Met Phe Gly Leu Val Thr Ile Asp Asp Val
            275                 280                 285

Tyr Asp Val Tyr Gly Thr Leu Asp Glu Leu Gln Leu Phe Thr Asp Ala
            290                 295                 300

Val Glu Arg Trp Asp Val Asn Ala Leu Asp Thr Leu Pro Asp Tyr Met
305                 310                 315                 320

Lys Leu Cys Phe Leu Ala Leu Tyr Asn Thr Val Asn Asp Thr Ala Tyr
            325                 330                 335

Ser Leu Leu Arg Glu Arg Gly Asp Asn Ser Leu Pro Tyr Leu Ala Lys
            340                 345                 350

Ser Trp Ser Glu Leu Cys Lys Ala Phe Leu Gln Glu Ala Lys Trp Ser
            355                 360                 365

Asn Lys Lys Thr Ile Pro Glu Phe Arg Glu Tyr Leu Asp Asn Ala Ser
            370                 375                 380

Val Ser Ser Ser Gly Gly Ala Leu Leu Thr Pro Cys Tyr Phe Ser Leu
385                 390                 395                 400

Leu Thr Gln Asp Val Ala Val Thr Ser Gln Phe His Ser Ser Thr Ile
            405                 410                 415

Asp Ser Leu Thr Asn Phe His Gly Val Val Arg Ser Ser Cys Thr Ile
            420                 425                 430

Phe Arg Leu Cys Asn Asp Leu Ala Thr Ser Ala Ala Glu Leu Glu Arg
            435                 440                 445

Gly Glu Thr Thr Asn Ser Ile Thr Ser Tyr Met Arg Glu Lys Gly Val
            450                 455                 460

Gly Glu Glu Glu Ala Arg Glu Glu Leu Ser Lys Leu Ile Asp Val Glu
465                 470                 475                 480

Trp Met Lys Leu Asn Arg Glu Arg Val Leu Asp Ile Gly Pro Phe Pro
            485                 490                 495

Lys Ala Phe Met Glu Thr Ala Val Asn Met Ala Arg Val Ser His Cys
            500                 505                 510

Thr Tyr Gln His Gly Asp Gly Leu Gly Arg Pro Asp Asn Thr Ala Gln
            515                 520                 525

Asn Arg Ile Lys Leu Leu Leu Asn Pro Ile Pro Ser
530                 535                 540

<210> SEQ ID NO 44
<211> LENGTH: 534
<212> TYPE: PRT
<213> ORGANISM: Robinia pseudoacacia

<400> SEQUENCE: 44

Arg Ser Ala Asn Tyr Gln Pro Asn Leu Trp Asn Phe Glu Phe Leu Gln
1               5                   10                  15

Ser Gln Glu Tyr Asp Leu Met Val Glu Thr Leu Gln Glu Arg Ala Thr
            20                  25                  30

Lys Leu Glu Glu Glu Val Arg Arg Leu Ile Asn Arg Val Asp Ile Glu
            35                  40                  45

Pro Leu Lys Leu Leu Glu Leu Val Asp Asn Val Gln Arg Leu Gly Leu
        50                  55                  60
```

```
Thr Tyr Lys Phe Glu Asp Asp Ile Asn Lys Ala Leu Glu Arg Ile Val
 65                  70                  75                  80

Ser Leu Asp Glu Arg Glu Lys Ser Gly Leu His Ala Thr Ala Leu Ile
                 85                  90                  95

Phe Arg Leu Leu Arg Gln His Gly Phe Glu Val Ser Gln Asp Val Phe
            100                 105                 110

Glu Ser Thr Arg Asp Lys Glu Gly Arg Phe Lys Ala Glu Ile Lys Gly
        115                 120                 125

Asp Val Gln Gly Leu Leu Ser Leu Tyr Glu Ala Ser Tyr Leu Gly Phe
    130                 135                 140

Glu Gly Glu Asn Leu Leu Asp Glu Ala Arg Glu Phe Ser Met Thr His
145                 150                 155                 160

Leu Lys Asn Leu Asn Glu Gly Val Val Thr Pro Lys Leu Ala Glu Gln
                165                 170                 175

Ile Asn His Ala Leu Glu Leu Pro Tyr His Arg Arg Phe Gln Arg Leu
            180                 185                 190

Glu Ala Arg Trp Phe Ile Glu Asn Tyr Glu Val Lys Glu Pro His Asp
        195                 200                 205

Arg Leu Leu Val Glu Leu Ala Lys Leu Asp Phe Asn Met Val Gln Ser
    210                 215                 220

Leu Gln Lys Lys Glu Val Gly Glu Leu Ser Arg Trp Trp Lys Glu Ile
225                 230                 235                 240

Gly Leu Thr Ser Lys Leu Asp Phe Val Arg Asp Arg Leu Val Glu Val
                245                 250                 255

Tyr Phe Trp Ala Ser Gly Met Ala Pro Asp Pro Gln Leu Ser Glu Cys
            260                 265                 270

Arg Lys Ala Val Thr Lys Met Phe Gly Leu Val Thr Ile Ile Asp Asp
        275                 280                 285

Val Tyr Asp Val Tyr Gly Thr Leu Asp Glu Leu Glu Leu Phe Thr Asn
    290                 295                 300

Ala Val Glu Arg Trp Asp Val Asn Ala Val Asp Thr Leu Pro Asp Tyr
305                 310                 315                 320

Met Lys Leu Cys Phe Phe Ala Leu Tyr Asn Thr Val Asn Asp Thr Ala
                325                 330                 335

Tyr Asn Leu Leu Lys Glu Lys Gly Asp Asn Asn Leu Pro Tyr Leu Ala
            340                 345                 350

Lys Ser Trp Ser Asp Leu Cys Lys Ala Phe Leu Gln Glu Ala Lys Trp
        355                 360                 365

Ser Asn Asn Lys Ile Ile Pro Ser Phe Asn Lys Tyr Ile Glu Asn Ala
    370                 375                 380

Ser Val Ser Ser Gly Gly Ala Leu Leu Thr Pro Cys Tyr Phe Ser
385                 390                 395                 400

Ile Arg Gln Asp Ile Thr Asn Gln Ala Leu Asp Ser Leu Thr Asn Tyr
                405                 410                 415

His Gly Pro Val Arg Ser Ser Cys Ala Ile Phe Arg Leu Cys Asn Asp
            420                 425                 430

Leu Ala Thr Ser Ala Ala Glu Leu Glu Arg Gly Glu Thr Thr Asn Ser
        435                 440                 445

Ile Thr Ser Tyr Met Gln Asp Asn Gly Ile Ser Glu Glu Gln Ala Arg
    450                 455                 460

Asp Glu Leu Arg Asn Leu Ile Asp Ala Glu Trp Lys Gln Ile Asn Arg
465                 470                 475                 480

Glu Arg Val Phe Asp Gln Thr Phe Pro Lys Ala Phe Ile Glu Thr Ala
```

```
                        485                 490                 495
Ile Asn Met Ala Arg Val Ser His Cys Thr Tyr Gln Tyr Gly Asp Gly
                500                 505                 510

Leu Gly Arg Pro Asp Asn Thr Ala Glu Asn Arg Ile Lys Leu Leu Leu
                515                 520                 525

Ile Asp Pro Phe Pro Ile
    530

<210> SEQ ID NO 45
<211> LENGTH: 544
<212> TYPE: PRT
<213> ORGANISM: Arachis hypogaea

<400> SEQUENCE: 45

Met Asn Thr Arg Arg Ser Ala Asn Tyr Gln Pro Asn Leu Trp Asp Phe
1               5                   10                  15

Glu Phe Leu Gln Ser Val Glu Asn Asp Leu Gln Val Glu Arg Leu Glu
                20                  25                  30

Glu Arg Ala Arg Lys Leu Glu Glu Val Arg Gly Leu Met Lys Lys
            35                  40                  45

Val Glu Ile Glu Pro Leu Ser Leu Leu Glu Leu Met Asp Asn Val Glu
    50                  55                  60

Arg Leu Gly Leu Thr Tyr Lys Phe Glu Glu Asp Ile Lys Ser Ala Leu
65              70                  75                  80

Asn Asn Arg Ile Val Pro Leu Leu His His Thr Ile Asn Lys Tyr
                85                  90                  95

Gly Leu His Ala Thr Ala Leu Ser Phe Arg Phe Leu Arg Gln His Ala
                100                 105                 110

Phe His Val Ser Pro Asp Val Phe Glu Ser Phe Lys Glu Glu Gly Lys
            115                 120                 125

Phe Lys Lys Glu Ile Ser Gly Asp Val Leu Gly Leu Leu Asn Leu Tyr
        130                 135                 140

Glu Thr Ser Tyr Leu Gly Phe Glu Gly Glu Thr Ile Leu Asp Glu Ala
145                 150                 155                 160

Arg Ala Phe Ser Ala Thr His Leu Lys Asn Leu Leu Gln Thr Asn Gln
                165                 170                 175

Val Gln Asn Lys Val Met Ala Glu Lys Val Arg His Ala Leu Glu Leu
            180                 185                 190

Pro Tyr His Arg Arg Val His Arg Leu Glu Ala Arg Trp Phe Ile Glu
        195                 200                 205

Arg Tyr Glu Gln Lys Glu Ala His Asp Gly Ala Leu Leu Glu Leu Ala
    210                 215                 220

Lys Leu Asp Phe Asn Met Val Gln Ser Val Met Lys Lys Glu Leu Gln
225                 230                 235                 240

Glu Leu Ser Arg Trp Trp Arg Glu Ile Gly Leu Thr Ser Lys Leu Asp
                245                 250                 255

Phe Val Arg Asp Arg Leu Met Glu Val Tyr Phe Trp Ala Leu Gly Met
            260                 265                 270

Ala Pro His Pro Gln Leu Thr Glu Cys Arg Lys Ala Val Thr Lys Met
        275                 280                 285

Phe Gly Leu Val Thr Ile Ile Asp Asp Val Tyr Asp Val Tyr Gly Thr
    290                 295                 300

Leu Asp Glu Leu Gln Leu Phe Thr Asp Ala Val Asp Arg Trp Asp Val
305                 310                 315                 320
```

```
Asn Ala Val Glu Thr Leu Pro Asp Tyr Met Lys Leu Cys Tyr Leu Ala
            325                 330                 335

Leu Tyr Asn Ser Val Asn Asp Thr Ala Tyr Ser Thr Leu Arg Glu Lys
        340                 345                 350

Gly Asp Asn Ser Leu Pro His Leu Ala Lys Ser Trp Arg Asp Leu Cys
        355                 360                 365

Lys Ala Phe Leu Gln Glu Ala Lys Trp Ser Asn Asn Lys Ile Ile Pro
    370                 375                 380

Pro Phe Asp Ala Tyr Ile Arg Asn Ala Ser Val Ser Ser Ser Gly Gly
385                 390                 395                 400

Ala Leu Leu Ala Pro Cys Tyr Phe Ser Val Thr Gln Asp Ser Thr Ser
                405                 410                 415

Gln Ala Ile Asp Ser Ile Thr Asn Tyr His Gly Ile Val Arg Ser Ser
            420                 425                 430

Cys Ala Ile Phe Arg Leu Cys Asn Asp Leu Ala Thr Ser Ala Ala Glu
        435                 440                 445

Leu Glu Arg Gly Glu Thr Thr Asn Ser Ile Thr Ser Tyr Met Thr Glu
    450                 455                 460

Asn Gly Thr Thr Glu Glu Ala Arg Glu Ser Leu Gly Lys Leu Ile
465                 470                 475                 480

Asp Gln Glu Trp Lys Lys Met Asn Arg Asp Val Val Leu Glu Ser Ala
                485                 490                 495

Tyr Pro Asn Val Phe Lys Glu Ile Ala Ile Asn Met Ala Arg Val Ser
            500                 505                 510

His Cys Thr Tyr Gln Tyr Gly Asp Gly Leu Gly Arg Pro Asp Asp Thr
        515                 520                 525

Ala Glu Asn Arg Ile Lys Leu Ser Leu Ile Glu Pro Ile Pro Ile Asn
    530                 535                 540

<210> SEQ ID NO 46
<211> LENGTH: 545
<212> TYPE: PRT
<213> ORGANISM: Glycine max

<400> SEQUENCE: 46

Met Glu Thr Arg Arg Ser Ala Asn Tyr Gln Pro Asn Leu Trp Asn Phe
1               5                   10                  15

Glu Phe Leu Pro Pro Ser Leu Glu Asn Asp His Lys Val Glu Lys Leu
            20                  25                  30

Glu Glu Arg Ala Lys Lys Val Glu Glu Val Arg Lys Val Ile Asn
        35                  40                  45

Gly Ile Asp Thr Lys Pro Leu Leu Glu Leu Ile Asp Asp Val Gln
    50                  55                  60

His Leu Gly Leu Thr Tyr Lys Phe Glu Lys Asp Ile Ile Lys Ala Leu
65                  70                  75                  80

Glu Lys Ile Val Ser Leu Asp Glu Asn Glu Glu His Lys Ser Glu Leu
                85                  90                  95

Tyr Tyr Thr Ala Leu Ser Phe Arg Leu Leu Arg Gln His Gly Phe Glu
            100                 105                 110

Val Ser Gln Asp Val Phe Lys Arg Phe Lys Asp Lys Glu Gly Gly Phe
        115                 120                 125

Ser Gly Glu Leu Lys Gly Asp Val Gln Gly Leu Leu Ser Leu Tyr Glu
    130                 135                 140

Ala Ser Tyr Leu Gly Phe Glu Gly Asp Asn Leu Leu Asp Glu Ala Arg
145                 150                 155                 160
```

```
Ala Phe Ser Thr Thr His Leu Lys Asn Asn Leu Lys Gln Gly Ile Asn
            165                 170                 175

Thr Lys Glu Ala Glu Gln Val Asn His Ala Leu Glu Leu Pro Tyr His
            180                 185                 190

Arg Arg Leu Gln Arg Leu Glu Ala Arg Trp Tyr Leu Lys Tyr Glu
        195                 200                 205

Pro Lys Glu Pro His His Gln Leu Leu Leu Glu Leu Ala Lys Leu Asp
        210                 215                 220

Phe Asn Met Val Gln Leu Leu His Gln Lys Glu Leu Gln Glu Leu Ser
225                 230                 235                 240

Arg Trp Trp Ser Glu Met Gly Leu Ala Ser Lys Leu Glu Phe Ala Arg
                245                 250                 255

Asp Arg Leu Met Glu Val Tyr Phe Trp Ala Leu Gly Met Ala Pro Asp
                260                 265                 270

Pro Gln Phe Arg Glu Cys Arg Lys Ala Val Thr Lys Met Phe Gly Leu
            275                 280                 285

Val Thr Ile Ile Asp Asp Val Tyr Asp Ile Tyr Gly Thr Leu Asp Glu
290                 295                 300

Leu Gln Leu Phe Thr Asp Ala Val Glu Arg Trp Asp Val Asn Val Val
305                 310                 315                 320

Asn Thr Leu Pro Asp Tyr Met Lys Leu Cys Tyr Leu Ala Leu Tyr Asn
                325                 330                 335

Thr Val Asn Asp Thr Ala Tyr Ser Ile Leu Lys Glu Lys Gly Arg Asn
                340                 345                 350

Asn Leu Ser Tyr Leu Lys Lys Ser Trp Cys Glu Leu Cys Lys Ala Phe
            355                 360                 365

Leu Gln Glu Ala Lys Trp Ser Asn Asn Lys Ile Val Pro Ala Phe Ser
370                 375                 380

Lys Tyr Leu Glu Asn Ala Ser Val Ser Ser Gly Val Ala Leu Leu
385                 390                 395                 400

Ala Pro Ser Tyr Phe Ser Val Cys Gln Glu Gln Asp Ile Ser Phe Ser
            405                 410                 415

Asp Lys Thr Leu His Tyr Leu Thr Asn Phe Gly Gly Leu Val Arg Ser
            420                 425                 430

Ser Cys Thr Ile Phe Arg Leu Cys Asn Asp Leu Thr Thr Ser Ala Ala
            435                 440                 445

Glu Leu Glu Arg Gly Glu Thr Thr Asn Ser Ile Met Ser Tyr Met His
450                 455                 460

Glu Asn Gly Thr Ser Glu His Ala Cys Glu Leu Arg Asn Leu
465                 470                 475                 480

Ile Asp Ile Glu Trp Lys Lys Met Asn Arg Gln Arg Val Ser Asp Ser
                485                 490                 495

Thr Leu Pro Lys Ala Phe Arg Glu Ile Ala Met Asn Met Ala Arg Val
            500                 505                 510

Ser His Asn Thr Tyr Gln Tyr Gly Asp Gly Leu Gly Arg Pro Asp Tyr
            515                 520                 525

Asn Ile Glu Asn Arg Ile Lys Phe Leu Leu Ile Asp Pro Val Pro Ile
530                 535                 540

Asn
545

<210> SEQ ID NO 47
<211> LENGTH: 608
```

<212> TYPE: PRT
<213> ORGANISM: Pueraria montana var. lobata

<400> SEQUENCE: 47

```
Met Ala Thr Asn Leu Leu Cys Leu Ser Asn Lys Leu Ser Ser Pro Thr
1               5                   10                  15

Pro Thr Pro Ser Thr Arg Phe Pro Gln Ser Lys Asn Phe Ile Thr Gln
            20                  25                  30

Lys Thr Ser Leu Ala Asn Pro Lys Pro Trp Arg Val Ile Cys Ala Thr
        35                  40                  45

Ser Ser Gln Phe Thr Gln Ile Thr Glu His Asn Ser Arg Arg Ser Ala
    50                  55                  60

Asn Tyr Gln Pro Asn Leu Trp Asn Phe Glu Phe Leu Gln Ser Leu Glu
65                  70                  75                  80

Asn Asp Leu Lys Val Glu Lys Leu Glu Glu Lys Ala Thr Lys Leu Glu
                85                  90                  95

Glu Glu Val Arg Cys Met Ile Asn Arg Val Asp Thr Gln Pro Leu Ser
            100                 105                 110

Leu Leu Glu Leu Ile Asp Asp Val Gln Arg Leu Gly Leu Thr Tyr Lys
        115                 120                 125

Phe Glu Lys Asp Ile Ile Lys Ala Leu Glu Asn Ile Val Leu Leu Asp
130                 135                 140

Glu Asn Lys Lys Asn Lys Ser Asp Leu His Ala Thr Ala Leu Ser Phe
145                 150                 155                 160

Arg Leu Leu Arg Gln His Gly Phe Glu Val Ser Gln Asp Val Phe Glu
                165                 170                 175

Arg Phe Lys Asp Lys Glu Gly Gly Phe Ser Gly Glu Leu Lys Gly Asp
            180                 185                 190

Val Gln Gly Leu Leu Ser Leu Tyr Glu Ala Ser Tyr Leu Gly Phe Glu
        195                 200                 205

Gly Glu Asn Leu Leu Glu Glu Ala Arg Thr Phe Ser Ile Thr His Leu
210                 215                 220

Lys Asn Asn Leu Lys Glu Gly Ile Asn Thr Lys Val Ala Glu Gln Val
225                 230                 235                 240

Ser His Ala Leu Glu Leu Pro Tyr His Gln Arg Leu His Arg Leu Glu
                245                 250                 255

Ala Arg Trp Phe Leu Asp Lys Tyr Glu Pro Lys Glu Pro His His Gln
            260                 265                 270

Leu Leu Leu Glu Leu Ala Lys Leu Asp Phe Asn Met Val Gln Thr Leu
        275                 280                 285

His Gln Lys Glu Leu Gln Asp Leu Ser Arg Trp Trp Thr Glu Met Gly
    290                 295                 300

Leu Ala Ser Lys Leu Asp Phe Val Arg Asp Arg Leu Met Glu Val Tyr
305                 310                 315                 320

Phe Trp Ala Leu Gly Met Ala Pro Asp Pro Gln Phe Gly Glu Cys Arg
                325                 330                 335

Lys Ala Val Thr Lys Met Phe Gly Leu Val Thr Ile Ile Asp Asp Val
            340                 345                 350

Tyr Asp Val Tyr Gly Thr Leu Asp Glu Leu Gln Leu Phe Thr Asp Ala
        355                 360                 365

Val Glu Arg Trp Asp Val Asn Ala Ile Asn Thr Leu Pro Asp Tyr Met
    370                 375                 380

Lys Leu Cys Phe Leu Ala Leu Tyr Asn Thr Val Asn Asp Thr Ser Tyr
385                 390                 395                 400
```

```
Ser Ile Leu Lys Glu Lys Gly His Asn Asn Leu Ser Tyr Leu Thr Lys
            405                 410                 415

Ser Trp Arg Glu Leu Cys Lys Ala Phe Leu Gln Glu Ala Lys Trp Ser
            420                 425                 430

Asn Asn Lys Ile Ile Pro Ala Phe Ser Lys Tyr Leu Glu Asn Ala Ser
            435                 440                 445

Val Ser Ser Ser Gly Val Ala Leu Leu Ala Pro Ser Tyr Phe Ser Val
            450                 455                 460

Cys Gln Gln Gln Glu Asp Ile Ser Asp His Ala Leu Arg Ser Leu Thr
465                 470                 475                 480

Asp Phe His Gly Leu Val Arg Ser Ser Cys Val Ile Phe Arg Leu Cys
            485                 490                 495

Asn Asp Leu Ala Thr Ser Ala Ala Glu Leu Glu Arg Gly Glu Thr Thr
            500                 505                 510

Asn Ser Ile Ile Ser Tyr Met His Glu Asn Asp Gly Thr Ser Glu Glu
            515                 520                 525

Gln Ala Arg Glu Glu Leu Arg Lys Leu Ile Asp Ala Glu Trp Lys Lys
            530                 535                 540

Met Asn Arg Glu Arg Val Ser Asp Ser Thr Leu Leu Pro Lys Ala Phe
545                 550                 555                 560

Met Glu Ile Ala Val Asn Met Ala Arg Val Ser His Cys Thr Tyr Gln
            565                 570                 575

Tyr Gly Asp Gly Leu Gly Arg Pro Asp Tyr Ala Thr Glu Asn Arg Ile
            580                 585                 590

Lys Leu Leu Leu Ile Asp Pro Phe Pro Ile Asn Gln Leu Met Tyr Val
            595                 600                 605
```

<210> SEQ ID NO 48
<211> LENGTH: 600
<212> TYPE: PRT
<213> ORGANISM: Mucuna pruriens

<400> SEQUENCE: 48

```
Met Ala Thr Lys Val Leu Cys Leu Ser Asn Gln Phe Leu Tyr Pro Thr
1               5                   10                  15

Pro Thr Leu Thr Ser Thr Arg Phe Leu Gln Thr Glu Asn Phe Thr Gln
            20                  25                  30

Lys Thr Ser Leu Ile Asn Pro Lys Pro Tyr Pro Leu Phe Cys Val Val
            35                  40                  45

Thr Ser Gln Phe Ser Gln Ile Thr Glu Asp Asn Thr Arg Arg Ser Ala
        50                  55                  60

Asn Tyr His Pro Asn Leu Trp Asn Phe Glu Phe Leu Gln Ser Leu Glu
65                  70                  75                  80

Asn Asp Pro Lys Ile Glu Lys Leu Glu Lys Ala Thr Lys Leu Val
            85                  90                  95

Glu Glu Val Arg His Met Met Asn Lys Ala Glu Thr Glu Pro Leu Ser
            100                 105                 110

Leu Leu Glu Leu Ile Asp Asp Val Gln Arg Leu Gly Leu Thr Tyr Lys
            115                 120                 125

Phe Glu Lys Asp Ile Ile Asn Ala Leu Glu Lys Thr Ile Ser Leu Asp
            130                 135                 140

Glu Asn Gln Lys His Ile Ser Gly Leu His Ala Thr Ser Leu Ser Phe
145                 150                 155                 160

Arg Leu Leu Arg Gln His Gly Phe Glu Val Ser Gln Asp Val Phe Lys
```

-continued

```
                165                 170                 175
Lys Phe Lys Asp Glu Asp Gly Gly Phe Ser Ala Glu Leu Lys Gly Asp
                180                 185                 190

Val Gln Gly Leu Leu Ser Leu Tyr Glu Ala Ser Tyr Leu Gly Phe Glu
                195                 200                 205

Gly Glu Asn Leu Leu Asp Glu Ala Arg Glu Phe Ser Ile Glu His Leu
                210                 215                 220

Lys Asn Asn Leu Asn Lys Gly Ile Thr Thr Lys Val Ala Glu Gln Val
225                 230                 235                 240

Ser His Ala Leu Glu Leu Pro Tyr His Arg Arg Ile His Arg Leu Glu
                245                 250                 255

Ala Arg Trp Phe Leu Asp Lys Tyr Glu Pro Lys Glu Ser Gln His Lys
                260                 265                 270

Leu Leu Leu Glu Leu Ala Lys Leu Asp Phe Asn Met Val Gln Ser Leu
                275                 280                 285

His Gln Lys Glu Leu Arg Glu Leu Ser Met Trp Trp Arg Glu Ile Gly
                290                 295                 300

Leu Thr Ser Lys Leu Asp Phe Val Arg Asp Arg Leu Met Glu Val Tyr
305                 310                 315                 320

Phe Trp Ala Leu Gly Met Ala Pro Asp Pro Gln Phe Ser Glu Cys Arg
                325                 330                 335

Lys Ala Val Thr Lys Met Phe Gly Leu Val Thr Ile Ile Asp Asp Val
                340                 345                 350

Tyr Asp Val Tyr Gly Thr Leu Asp Glu Leu Gln Leu Phe Thr Asp Ala
                355                 360                 365

Val Glu Arg Trp Asp Val Asn Ala Ile Asn Thr Leu Pro Asp Tyr Met
                370                 375                 380

Lys Leu Cys Phe Leu Ala Leu Tyr Asn Thr Val Asn Asp Thr Thr Tyr
385                 390                 395                 400

Ser Ile Leu Lys Glu Lys Gly His Asn Asn Ile Ser Tyr Leu Thr Lys
                405                 410                 415

Ser Trp Cys Glu Leu Cys Lys Ala Phe Leu Gln Glu Ala Lys Trp Ser
                420                 425                 430

Asn Asn Lys Ile Ile Pro Thr Phe Asn Lys Tyr Leu Arg Asn Ala Ser
                435                 440                 445

Val Ser Ser Gly Val Ala Leu Leu Ala Pro Ser Phe Phe Leu Val
                450                 455                 460

Cys Gln Glu Gln Asp Ile Ser Glu Gln Ala Leu His Ser Leu Ile Asn
465                 470                 475                 480

Phe His Gly Leu Val Arg Ser Ser Cys Val Ile Phe Arg Leu Cys Asn
                485                 490                 495

Asp Leu Ala Thr Ser Ala Ala Glu Leu Glu Arg Gly Glu Thr Thr Asn
                500                 505                 510

Ser Ile Thr Ser Tyr Met His Glu Asn Gly Thr Ser Glu Glu Gln Ala
                515                 520                 525

Arg Gln Glu Leu Arg Ile Leu Ile Asp Ala Glu Trp Lys Asn Met Asn
                530                 535                 540

Gln Glu Arg Tyr Leu Asp Ser Thr Leu Pro Asp Ala Phe Met Glu Ile
545                 550                 555                 560

Thr Ile Asn Leu Ala Arg Val Ser His Cys Thr Tyr Gln Tyr Gly Asp
                565                 570                 575

Gly Leu Gly Arg Pro Asp Tyr Thr Thr Lys Asn Arg Ile Lys Leu Leu
                580                 585                 590
```

```
Leu Ile Asp Pro Leu Pro Ile Asn
        595                 600

<210> SEQ ID NO 49
<211> LENGTH: 545
<212> TYPE: PRT
<213> ORGANISM: Glycine max

<400> SEQUENCE: 49

Met Glu Thr Arg Arg Ser Ala Asn Tyr Gln Pro Asn Leu Trp Asn Phe
1               5                   10                  15

Glu Phe Leu Pro Pro Ser Leu Glu Asn Asp His Lys Val Glu Lys Leu
            20                  25                  30

Glu Glu Arg Ala Arg Lys Val Glu Glu Val Arg Arg Met Ile Asn
        35                  40                  45

Gly Ala Asp Thr Glu Ala Leu Arg Leu Leu Glu Leu Ile Asp Glu Ile
50                  55                  60

Gln Arg Leu Gly Leu Thr Tyr Lys Phe Glu Lys Asp Ile Phe Lys Ala
65                  70                  75                  80

Leu Glu Lys Thr Ile Ser Leu Asp Glu Asn Glu Lys His Ile Ser Gly
                85                  90                  95

Leu His Ala Thr Ala Leu Ser Phe Arg Leu Leu Arg Gln His Gly Phe
            100                 105                 110

Glu Val Ser Gln Asp Val Phe Lys Arg Phe Lys Asp Lys Glu Gly Gly
        115                 120                 125

Phe Ile Asn Glu Leu Lys Gly Asp Met Gln Gly Leu Leu Ser Leu Tyr
130                 135                 140

Glu Ala Ser Tyr Leu Gly Phe Glu Gly Glu Thr Leu Leu Asp Glu Ala
145                 150                 155                 160

Arg Ala Tyr Ser Ile Thr His Leu Lys Asn Asn Leu Lys Val Gly Val
                165                 170                 175

Asn Thr Glu Val Lys Glu Gln Val Ser His Ala Leu Glu Leu Pro Tyr
            180                 185                 190

His Arg Gly Leu Asn Arg Leu Glu Ala Arg Trp Phe Leu Glu Lys Tyr
        195                 200                 205

Glu Pro Asn Glu Ser His His Val Leu Leu Glu Leu Ala Lys Ile
210                 215                 220

Asp Phe Asn Leu Val Gln Val Met Tyr Gln Lys Glu Leu Arg Glu Leu
225                 230                 235                 240

Ser Arg Trp Trp Ser Glu Met Gly Leu Thr Ser Lys Leu Lys Phe Val
                245                 250                 255

Arg Asp Arg Leu Met Glu Val Tyr Phe Trp Val Leu Gly Met Ala Pro
            260                 265                 270

Arg Pro Gln Phe Ser Glu Cys Arg Lys Ala Val Thr Lys Thr Phe Ala
        275                 280                 285

Leu Ile Gly Ile Ile Asp Asp Val Tyr Asp Val Tyr Gly Thr Leu Asp
        290                 295                 300

Glu Leu Gln Leu Phe Thr Asp Ala Ile Glu Arg Trp Asp Val Asn Ala
305                 310                 315                 320

Met Asn Thr Leu Pro Asp Tyr Met Lys Leu Cys Tyr Leu Ala Val Tyr
                325                 330                 335

Asn Thr Val Asn Asp Thr Cys Tyr Ser Thr Leu Lys Ala Lys Gly His
            340                 345                 350

Asn Asn Met Ser Tyr Leu Thr Lys Ser Trp Cys Glu Leu Cys Lys Ala
```

```
                355                 360                 365
Phe Leu Gln Glu Ala Lys Trp Ser Asn Asn Lys Ile Val Pro Thr Phe
370                 375                 380

Ser Lys Tyr Leu Glu Asn Ala Ser Val Ser Ser Gly Met Ala Leu
385                 390                 395                 400

Leu Thr Ala Ser Tyr Phe Ser Val Cys Gln Gln Asp Ile Ser Asn
            405                 410                 415

Gln Gln Ala Leu Cys Ser Leu Thr Asn Phe Gln Gly Leu Val Arg Ser
                420                 425                 430

Ser Ser Asn Ile Phe Arg Leu Cys Asn Asp Leu Ala Thr Ser Ala Ala
            435                 440                 445

Glu Leu Glu Thr Gly Glu Thr Ala Asn Ser Ile Thr Cys Tyr Met His
    450                 455                 460

Glu Lys Asp Thr Ser Glu Gln Ala Arg Glu Leu Thr Asn Leu
465                 470                 475                 480

Ile Asp Ala Glu Trp Lys Lys Met Asn Arg Glu Phe Val Ser Asn Ser
                485                 490                 495

Thr Leu Pro Lys Ala Phe Lys Glu Ile Ala Ile Asn Met Ala Arg Val
            500                 505                 510

Ser His Cys Met Tyr Gln Tyr Glu Asp Gly Leu Gly Arg Pro Gly Tyr
        515                 520                 525

Thr Thr Glu Asn Lys Ile Lys Leu Leu Leu Ile Asp Pro Val Pro Ile
    530                 535                 540

Asn
545

<210> SEQ ID NO 50
<211> LENGTH: 598
<212> TYPE: PRT
<213> ORGANISM: Cajanus cajan

<400> SEQUENCE: 50

Met Ala Thr His His Leu Leu Cys Leu Ser Asn Pro Phe Ser Ser Pro
1               5                   10                  15

Ser Pro Thr Leu Ser Thr Ala Thr Arg Ser Phe Pro Leu Thr Asn Asn
                20                  25                  30

Phe Asn His Lys Thr Ser Leu Ala Asn Ser Lys Pro Cys Pro Phe Ile
            35                  40                  45

Cys Ser Gln Ile Thr His His His Thr Arg Arg Ser Ala Asn Tyr
    50                  55                  60

Gln Pro Asn Leu Trp Asn Phe Glu Phe Leu Gln Ser Leu Gln Asn His
65                  70                  75                  80

His Gln Val Phe Thr Met Phe Arg Arg Lys Leu Glu Lys Glu Val Arg
                85                  90                  95

Cys Met Met Asn Lys Ala Asp Ala Glu Ala Leu Ser Leu Leu Glu Leu
            100                 105                 110

Ile Asp Asp Val Gln Arg Leu Gly Leu Thr Tyr Arg Phe Glu Lys Asp
        115                 120                 125

Ile Ile Lys Val Leu Glu Lys Ile Val Ser Leu Asp Glu Ile Glu Lys
    130                 135                 140

His Gln Ser Gly Leu His Ala Thr Ala Leu Thr Phe Arg Leu Leu Arg
145                 150                 155                 160

Gln His Gly Phe His Gln Val Ser Gln Asp Met Phe Lys Arg Phe Lys
                165                 170                 175
```

```
Asp Lys Glu Gly Gly Phe Asn Asp Glu Leu Lys Gly Asp Val Gln Gly
            180                 185                 190

Leu Leu Ser Leu Tyr Glu Ala Ser Tyr Leu Gly Phe Glu Gly Glu Tyr
        195                 200                 205

Leu Leu Asp Glu Ala Arg Ala Phe Ser Ile Thr His Leu Asn Asn Ser
    210                 215                 220

Leu Lys Gln Gly Ile Asn Thr Lys Leu Ala Glu Gln Val Ser His Ala
225                 230                 235                 240

Leu Gln Leu Pro His Arg Arg Leu His Arg Leu Glu Ala Arg Trp
            245                 250                 255

Gln Leu Asp Lys Tyr Glu Pro Lys Glu Pro His His His Leu Leu Leu
        260                 265                 270

His Leu Ala Lys Leu Asp Phe Asn Ile Leu Gln Ser Leu Tyr Gln Asn
    275                 280                 285

Glu Leu Arg Glu Leu Ser Arg Trp Trp Arg Glu Met Gly Leu Thr Ser
290                 295                 300

Lys Leu Glu Phe Val Arg Asp Arg Leu Met Glu Val Tyr Phe Trp Ala
305                 310                 315                 320

Leu Gly Met Ala Pro His Pro Glu Phe Ser Glu Cys Arg Lys Ala Ile
            325                 330                 335

Thr Lys Met Phe Gly Leu Val Thr Ile Ile Asp Asp Val Tyr Asp Val
            340                 345                 350

Tyr Gly Thr Leu Asp Glu Leu Gln Leu Phe Thr Asp Ala Val Glu Arg
        355                 360                 365

Trp Asp Val Asn Val Val Asn Thr Leu Pro Tyr Tyr Met Lys Leu Cys
370                 375                 380

Tyr Leu Ala Leu Tyr Asn Thr Val Asn Glu Thr Ser Tyr Ser Ile Leu
385                 390                 395                 400

Lys Glu Asn Gly His Asn Ser Leu Ser Tyr Leu Ala Lys Ser Trp Cys
            405                 410                 415

Glu Leu Cys Lys Ala Phe Leu Glu Glu Ala Lys Trp Ser Lys Lys
            420                 425                 430

Val Ile Pro Ala Leu Asn Arg Tyr Leu Glu Asn Ala Trp Val Ser Ser
            435                 440                 445

Ser Gly Val Ala Leu Leu Ala Pro Cys Tyr Phe Ser Val Cys Lys Glu
    450                 455                 460

Glu Asp Lys Ile Ser Asp Glu Ala Leu His Ser Leu Thr Asn Phe His
465                 470                 475                 480

Gly Leu Val Arg Ser Ser Cys Ala Ile Phe Arg Leu Tyr Asn Asp Leu
            485                 490                 495

Ala Thr Ser Ala Ala Glu Leu Glu Arg Asp Glu Thr Thr Asn Ser Met
        500                 505                 510

Thr Cys Tyr Met His Glu Asn Gly Ser Cys Glu Glu Gln Ala Arg Glu
    515                 520                 525

Glu Leu Arg Lys Met Ile Glu Val Glu Trp Lys Met Asn Gln Glu
530                 535                 540

Gly Val Leu Asp Cys Thr Leu Pro Thr Ala Phe Lys Glu Ile Ala Met
545                 550                 555                 560

Asn Met Ala Arg Val Ser His Cys Thr Tyr Gln His Gly Asp Gly Leu
            565                 570                 575

Gly Arg Pro Asp Tyr Thr Thr Gln Asn Arg Ile Lys Leu Leu Leu Ile
        580                 585                 590

Asp Pro Leu Pro Ile Asn
```

<210> SEQ ID NO 51
<211> LENGTH: 613
<212> TYPE: PRT
<213> ORGANISM: Humulus lupulus

<400> SEQUENCE: 51

```
Met Gln Cys Met Ala Val His Gln Phe Ala Pro Leu Leu Ser Leu Leu
1               5                   10                  15

Asn Cys Ser Arg Ile Ser Ser Asp Phe Gly Arg Leu Phe Thr Pro Lys
            20                  25                  30

Thr Ser Thr Lys Ser Arg Ser Ser Thr Cys His Pro Ile Gln Cys Thr
        35                  40                  45

Val Val Asn Asn Thr Asp Arg Arg Ser Ala Asn Tyr Glu Pro Ser Ile
    50                  55                  60

Trp Ser Phe Asp Tyr Ile Gln Ser Leu Thr Ser Gln Tyr Lys Gly Lys
65                  70                  75                  80

Ser Tyr Ser Ser Arg Leu Asn Glu Leu Lys Glu Val Lys Met Met
                85                  90                  95

Glu Asp Gly Thr Lys Glu Cys Leu Ala Gln Leu Asp Leu Ile Asp Thr
                100                 105                 110

Leu Gln Arg Leu Gly Ile Ser Tyr His Phe Glu Asp Glu Ile Asn Thr
            115                 120                 125

Ile Leu Lys Arg Lys Tyr Ile Asn Ile Gln Asn Asn Ile Asn His Asn
        130                 135                 140

Tyr Asn Leu Tyr Ser Thr Ala Leu Gln Phe Arg Leu Leu Arg Gln His
145                 150                 155                 160

Gly Tyr Leu Val Thr Gln Glu Val Phe Asn Ala Phe Lys Asp Glu Thr
                165                 170                 175

Gly Lys Phe Lys Thr Tyr Leu Ser Asp Asp Ile Met Gly Val Leu Ser
            180                 185                 190

Leu Tyr Glu Ala Ser Phe Tyr Ala Met Lys His Glu Asn Val Leu Glu
        195                 200                 205

Glu Ala Arg Val Phe Ser Thr Glu Cys Leu Lys Glu Tyr Met Met Lys
    210                 215                 220

Met Glu Gln Asn Lys Val Leu Leu Asp His Asp Leu Asp His Asn Asp
225                 230                 235                 240

Asn Phe Asn Val Asn His His Val Leu Ile Ile Asn His Ala Leu Glu
                245                 250                 255

Leu Pro Leu His Trp Arg Ile Thr Arg Ser Glu Ala Arg Trp Phe Ile
            260                 265                 270

Asp Val Tyr Glu Lys Lys Gln Asp Met Asp Ser Thr Leu Leu Glu Phe
        275                 280                 285

Ala Lys Leu Asp Phe Asn Met Val Gln Ser Thr His Gln Glu Asp Leu
    290                 295                 300

Lys His Leu Ser Arg Trp Trp Arg His Ser Lys Leu Gly Glu Lys Leu
305                 310                 315                 320

Asn Phe Ala Arg Asp Arg Leu Met Glu Ala Phe Leu Trp Glu Val Gly
                325                 330                 335

Leu Lys Phe Glu Pro Glu Phe Ser Tyr Phe Lys Arg Ile Ser Ala Arg
            340                 345                 350

Leu Phe Val Leu Ile Thr Ile Ile Asp Asp Ile Tyr Asp Val Tyr Gly
        355                 360                 365
```

Thr Leu Glu Glu Leu Glu Leu Phe Thr Lys Ala Val Glu Arg Trp Asp
    370             375                 380

Val Asn Ala Ile Asn Glu Leu Pro Glu Tyr Met Lys Met Pro Phe Leu
385                 390                 395                 400

Val Leu His Asn Thr Ile Asn Glu Met Ala Phe Asp Val Leu Gly Asp
                405                 410                 415

Gln Asn Phe Leu Asn Ile Glu Tyr Leu Lys Ser Leu Val Asp Leu
            420             425             430

Cys Lys Cys Tyr Leu Gln Glu Ala Lys Trp Tyr Ser Gly Tyr Gln
        435             440             445

Pro Thr Leu Gln Glu Tyr Ile Glu Met Ala Trp Leu Ser Ile Gly Gly
    450             455                 460

Pro Val Ile Leu Val His Ala Tyr Phe Cys Phe Thr Asn Pro Ile Thr
465             470             475                 480

Lys Glu Ser Met Lys Phe Phe Thr Glu Gly Tyr Pro Asn Ile Ile Gln
                485             490                 495

Gln Ser Cys Leu Ile Val Arg Leu Ala Asp Asp Phe Gly Thr Phe Ser
            500             505             510

Asp Glu Leu Asn Arg Gly Asp Val Pro Lys Ser Ile Gln Cys Tyr Met
        515             520             525

Tyr Asp Thr Gly Ala Ser Glu Asp Glu Ala Arg Glu His Ile Lys Phe
    530             535             540

Leu Ile Cys Glu Thr Trp Lys Asp Met Asn Lys Asn Asp Glu Asp Asn
545             550             555                 560

Ser Cys Phe Ser Glu Thr Phe Val Glu Val Cys Lys Asn Leu Ala Arg
                565             570             575

Thr Ala Leu Phe Met Tyr Gln Tyr Gly Asp Gly His Ala Ser Gln Asn
            580             585             590

Cys Leu Ser Lys Glu Arg Ile Phe Ala Leu Ile Ile Asn Pro Ile Asn
        595             600             605

Phe His Glu Arg Lys
    610

<210> SEQ ID NO 52
<211> LENGTH: 56
<212> TYPE: PRT
<213> ORGANISM: Quercus petraea

<400> SEQUENCE: 52

Arg Asp Arg Leu Met Glu Cys Phe Phe Phe Ser Phe Ile Thr Val
1               5                   10                  15

Ile Asp Asp Ile Tyr Asp Phe Ser Val Ser Phe Arg Leu Thr Asn Asp
                20                  25                  30

Leu Gly Thr Ser Thr Ala Glu Leu Glu Arg Gly Glu Thr Ala Asn Ser
            35                  40                  45

Ile Tyr Gln His Gly Asp Gly His
    50                  55

<210> SEQ ID NO 53
<211> LENGTH: 56
<212> TYPE: PRT
<213> ORGANISM: Populus alba

<400> SEQUENCE: 53

Arg Asp Arg Leu Ile Glu Ser Phe Tyr Trp Phe Ser Phe Val Thr Ile
1               5                   10                  15

Ile Asp Asp Ile Tyr Asp Phe Ser Ser Ser Phe Arg Leu Cys Asn Asp
            20                  25                  30

Leu Ala Ser Ala Ser Ala Glu Ile Ala Arg Gly Glu Thr Ala Asn Ser
        35                  40                  45

Val Tyr His Asn Gly Asp Ala His
    50                  55

<210> SEQ ID NO 54
<211> LENGTH: 56
<212> TYPE: PRT
<213> ORGANISM: Populus canescens

<400> SEQUENCE: 54

Lys Asp Arg Leu Ile Glu Ser Phe Tyr Trp Phe Ser Phe Val Thr Ile
1               5                   10                  15

Ile Asp Asp Ile Tyr Asp Phe Ser Ser Ser Phe Arg Leu Cys Asn Asp
            20                  25                  30

Leu Ala Ser Ala Ser Ala Glu Ile Ala Arg Gly Glu Thr Ala Asn Ser
        35                  40                  45

Val Tyr His Asn Gly Asp Ala His
    50                  55

<210> SEQ ID NO 55
<211> LENGTH: 56
<212> TYPE: PRT
<213> ORGANISM: Salix sp.

<400> SEQUENCE: 55

Arg Asp Arg Leu Ile Glu Ser Phe Tyr Trp Phe Ser Phe Val Thr Ile
1               5                   10                  15

Ile Asp Asp Ile Tyr Asp Phe Ser Ser Ser Phe Arg Leu Cys Asn Asp
            20                  25                  30

Leu Ala Ser Ala Ser Ala Glu Ile Ala Arg Gly Glu Thr Ala Asn Ser
        35                  40                  45

Val Tyr His Asn Gly Asp Ala His
    50                  55

<210> SEQ ID NO 56
<211> LENGTH: 56
<212> TYPE: PRT
<213> ORGANISM: Melaleuca alternifolia

<400> SEQUENCE: 56

Arg Asp Arg Leu Met Glu Cys Phe Phe Trp Phe Ser Leu Ile Leu Val
1               5                   10                  15

Leu Asp Asp Val Tyr Asp Phe Ser Ser Ser Phe Arg Leu Thr Asn Asp
            20                  25                  30

Leu Ala Thr Ser Ser Ala Glu Leu Gly Arg Gly Glu Thr Thr Asn Ser
        35                  40                  45

Ile Tyr Gln Asp Gly Asp Ala Ile
    50                  55

<210> SEQ ID NO 57
<211> LENGTH: 56
<212> TYPE: PRT
<213> ORGANISM: Eucalyptus globulus

<400> SEQUENCE: 57

Arg Asp Arg Leu Ile Glu Cys Phe Phe Trp Phe Ala Leu Ile Leu Val
1               5                   10                  15

Leu Asp Asp Val Tyr Asp Phe Ser Ser Phe Arg Leu Thr Asn Asp
            20                  25                  30

Ile Ala Ser Ser Ala Glu Leu Glu Arg Gly Glu Thr Thr Asn Ser
            35                  40                  45

Ile Tyr Gln Asp Gly Asp Ala Ile
            50                  55

<210> SEQ ID NO 58
<211> LENGTH: 56
<212> TYPE: PRT
<213> ORGANISM: Wisteria sp.

<400> SEQUENCE: 58

Arg Asp Arg Leu Met Glu Val Tyr Phe Trp Phe Gly Leu Val Thr Ile
1               5                   10                  15

Ile Asp Asp Val Tyr Asp Phe Ser Ser Ser Phe Arg Leu Cys Asn Asp
            20                  25                  30

Leu Ala Thr Ser Ala Ala Glu Leu Glu Arg Gly Glu Thr Thr Asn Ser
            35                  40                  45

Ile Tyr Gln His Gly Asp Gly Leu
            50                  55

<210> SEQ ID NO 59
<211> LENGTH: 56
<212> TYPE: PRT
<213> ORGANISM: Robinia pseudoacacia

<400> SEQUENCE: 59

Arg Asp Arg Leu Val Glu Val Tyr Phe Trp Phe Gly Leu Val Thr Ile
1               5                   10                  15

Ile Asp Asp Val Tyr Asp Phe Ser Ser Ser Phe Arg Leu Cys Asn Asp
            20                  25                  30

Leu Ala Thr Ser Ala Ala Glu Leu Glu Arg Gly Glu Thr Thr Asn Ser
            35                  40                  45

Ile Tyr Gln Tyr Gly Asp Gly Leu
            50                  55

<210> SEQ ID NO 60
<211> LENGTH: 56
<212> TYPE: PRT
<213> ORGANISM: Arachis hypogaea

<400> SEQUENCE: 60

Arg Asp Arg Leu Met Glu Val Tyr Phe Trp Phe Gly Leu Val Thr Ile
1               5                   10                  15

Ile Asp Asp Val Tyr Asp Phe Ser Ser Ser Phe Arg Leu Cys Asn Asp
            20                  25                  30

Leu Ala Thr Ser Ala Ala Glu Leu Glu Arg Gly Glu Thr Thr Asn Ser
            35                  40                  45

Ile Tyr Gln Tyr Gly Asp Gly Leu
            50                  55

<210> SEQ ID NO 61
<211> LENGTH: 56
<212> TYPE: PRT
<213> ORGANISM: Glycine max

<400> SEQUENCE: 61

Arg Asp Arg Leu Met Glu Val Tyr Phe Trp Phe Gly Leu Val Thr Ile

```
1               5                  10                 15

Ile Asp Asp Val Tyr Asp Phe Ser Ser Phe Arg Leu Cys Asn Asp
                20                  25                  30

Leu Thr Thr Ser Ala Ala Glu Leu Glu Arg Gly Glu Thr Thr Asn Ser
        35                  40                  45

Ile Tyr Gln Tyr Gly Asp Gly Leu
    50                  55
```

<210> SEQ ID NO 62
<211> LENGTH: 56
<212> TYPE: PRT
<213> ORGANISM: Pueraria montana var. lobata

<400> SEQUENCE: 62

```
Arg Asp Arg Leu Met Glu Val Tyr Phe Trp Phe Gly Leu Val Thr Ile
1               5                  10                  15

Ile Asp Asp Val Tyr Asp Phe Ser Ser Ser Phe Arg Leu Cys Asn Asp
                20                  25                  30

Leu Ala Thr Ser Ala Ala Glu Leu Glu Arg Gly Glu Thr Thr Asn Ser
        35                  40                  45

Ile Tyr Gln Tyr Gly Asp Gly Leu
    50                  55
```

<210> SEQ ID NO 63
<211> LENGTH: 56
<212> TYPE: PRT
<213> ORGANISM: Mucuna pruriens

<400> SEQUENCE: 63

```
Arg Asp Arg Leu Met Glu Val Tyr Phe Trp Phe Gly Leu Val Thr Ile
1               5                  10                  15

Ile Asp Asp Val Tyr Asp Phe Ser Ser Ser Phe Arg Leu Cys Asn Asp
                20                  25                  30

Leu Ala Thr Ser Ala Ala Glu Leu Glu Arg Gly Glu Thr Thr Asn Ser
        35                  40                  45

Ile Tyr Gln Tyr Gly Asp Gly Leu
    50                  55
```

<210> SEQ ID NO 64
<211> LENGTH: 56
<212> TYPE: PRT
<213> ORGANISM: Glycine max

<400> SEQUENCE: 64

```
Arg Asp Arg Leu Met Glu Val Tyr Phe Trp Phe Ala Leu Ile Gly Ile
1               5                  10                  15

Ile Asp Asp Val Tyr Asp Phe Ser Ser Ser Phe Arg Leu Cys Asn Asp
                20                  25                  30

Leu Ala Thr Ser Ala Ala Glu Leu Glu Thr Gly Glu Thr Ala Asn Ser
        35                  40                  45

Ile Tyr Gln Tyr Glu Asp Gly Leu
    50                  55
```

<210> SEQ ID NO 65
<211> LENGTH: 56
<212> TYPE: PRT
<213> ORGANISM: Cajanus cajan

<400> SEQUENCE: 65

Arg Asp Arg Leu Met Glu Val Tyr Phe Trp Phe Gly Leu Val Thr Ile
1               5                   10                  15

Ile Asp Asp Val Tyr Asp Phe Ser Ser Ser Phe Arg Leu Tyr Asn Asp
                20                  25                  30

Leu Ala Thr Ser Ala Ala Glu Leu Glu Arg Asp Glu Thr Thr Asn Ser
                35                  40                  45

Met Tyr Gln His Gly Asp Gly Leu
    50                  55

<210> SEQ ID NO 66
<211> LENGTH: 56
<212> TYPE: PRT
<213> ORGANISM: Humulus lupulus

<400> SEQUENCE: 66

Arg Asp Arg Leu Met Glu Ala Phe Leu Trp Phe Val Leu Ile Thr Ile
1               5                   10                  15

Ile Asp Asp Ile Tyr Asp Tyr Ser Ile Gly Val Arg Leu Ala Asp Asp
                20                  25                  30

Phe Gly Thr Phe Ser Asp Glu Leu Asn Arg Gly Asp Val Pro Lys Ser
                35                  40                  45

Ile Tyr Gln Tyr Gly Asp Gly His
    50                  55

<210> SEQ ID NO 67
<211> LENGTH: 56
<212> TYPE: PRT
<213> ORGANISM: Medicago truncatula

<400> SEQUENCE: 67

Arg Asp Arg Leu Met Glu Cys Phe Phe Trp Cys Ser Leu Ile Thr Leu
1               5                   10                  15

Ile Asp Asp Ile Tyr Asp Phe Ser Val Ser Phe Arg Leu Cys Asn Asp
                20                  25                  30

Leu Ala Thr Ser Ser Ala Glu Leu Glu Arg Gly Glu Gly Ala Asn Ser
                35                  40                  45

Ile Tyr Gln Tyr Gly Asp Gly His
    50                  55

<210> SEQ ID NO 68
<211> LENGTH: 56
<212> TYPE: PRT
<213> ORGANISM: Medicago sativa

<400> SEQUENCE: 68

Arg Asp Arg Leu Met Glu Cys Phe Phe Trp Ser Ser Leu Ile Thr Leu
1               5                   10                  15

Ile Asp Asp Ile Tyr Asp Phe Ser Val Ser Phe Arg Leu Cys Asn Asp
                20                  25                  30

Leu Ala Thr Ser Ser Ala Glu Leu Glu Arg Gly Glu Gly Ala Asn Ser
                35                  40                  45

Ile Tyr Gln Tyr Gly Asp Gly His
    50                  55

<210> SEQ ID NO 69
<211> LENGTH: 56
<212> TYPE: PRT
<213> ORGANISM: Lotus japonicus

<400> SEQUENCE: 69

Arg Asp Arg Leu Met Glu Cys Phe Phe Trp Thr Ser Leu Ile Thr Thr
1               5                   10                  15

Ile Asp Asp Ile Tyr Asp Phe Ser Val Ser Phe Arg Leu Cys Asn Asp
                20                  25                  30

Leu Gly Thr Ser Thr Ala Glu Leu Gln Arg Gly Glu Val Ala Asn Ser
            35                  40                  45

Ile Tyr Gln Thr Gly Asp Gly His
    50                  55

<210> SEQ ID NO 70
<211> LENGTH: 56
<212> TYPE: PRT
<213> ORGANISM: Petraea sp.

<400> SEQUENCE: 70

Arg Asp Arg Leu Met Glu Cys Phe Phe Phe Ser Phe Ile Thr Val
1               5                   10                  15

Ile Asp Asp Ile Tyr Asp Phe Ser Val Ser Phe Arg Leu Thr Asn Asp
                20                  25                  30

Leu Gly Thr Ser Thr Ala Glu Leu Glu Arg Gly Glu Thr Ala Asn Ser
            35                  40                  45

Ile Tyr Gln His Gly Asp Gly His
    50                  55

<210> SEQ ID NO 71
<211> LENGTH: 56
<212> TYPE: PRT
<213> ORGANISM: Fragaria vesca

<400> SEQUENCE: 71

Lys Asp Arg Leu Met Glu Cys Phe Phe Trp Ser Ala Leu Ile Ser Thr
1               5                   10                  15

Val Asp Asp Val Tyr Asp Phe Ser Ala Ser Phe Arg Leu Thr Asn Asp
                20                  25                  30

Leu Ala Thr Ser Glu Ala Glu Leu Gly Arg Gly Glu Thr Ala Asn Ser
            35                  40                  45

Ile Tyr Gln Tyr Gly Asp Gly Ile
    50                  55

<210> SEQ ID NO 72
<211> LENGTH: 56
<212> TYPE: PRT
<213> ORGANISM: Morus notabilis

<400> SEQUENCE: 72

Arg Asp Arg Leu Met Glu Ser Phe Phe Trp Val Ala Phe Ile Thr Val
1               5                   10                  15

Ile Asp Asp Val Tyr Asp Phe Ser Ser Ser Phe Arg Leu Val Asn Asp
                20                  25                  30

Leu Ala Thr Ser Thr Ala Glu Leu Glu Arg Gly Glu Thr Asn Asn Ser
            35                  40                  45

Ile Tyr Gln His Gly Asp Gly His
    50                  55

<210> SEQ ID NO 73
<211> LENGTH: 56
<212> TYPE: PRT
<213> ORGANISM: Elaeocarpus sp.

<400> SEQUENCE: 73

Arg Asp Arg Leu Met Glu Ser Phe Phe Trp Phe Ala Leu Ile Thr Thr
1               5                   10                  15

Ile Asp Asp Val Tyr Asp Phe Ser Val Ser Phe Arg Leu Cys Asn Asp
                20                  25                  30

Leu Gly Thr Ser Ser Ala Glu Leu Glu Arg Gly Glu Leu Ala Asn Ser
            35                  40                  45

Ile Tyr Gln Tyr Gly Asp Ala His
    50                  55

<210> SEQ ID NO 74
<211> LENGTH: 56
<212> TYPE: PRT
<213> ORGANISM: Elaeocarpus photiniifolius

<400> SEQUENCE: 74

Arg Asp Arg Leu Met Glu Ser Phe Phe Trp Phe Ala Leu Ile Thr Thr
1               5                   10                  15

Ile Asp Asp Val Tyr Asp Phe Ser Val Ser Phe Arg Leu Cys Asn Asp
                20                  25                  30

Leu Gly Thr Ser Ser Ala Glu Leu Glu Arg Gly Glu Leu Ala Asn Ser
            35                  40                  45

Ile Tyr Gln Tyr Gly Asp Ala His
    50                  55

<210> SEQ ID NO 75
<211> LENGTH: 56
<212> TYPE: PRT
<213> ORGANISM: Populus trichocarpa

<400> SEQUENCE: 75

Arg Asp Arg Leu Met Glu Cys Phe Phe Trp Thr Ser Phe Ile Thr Thr
1               5                   10                  15

Ile Asp Asp Val Tyr Asp Phe Ser Val Ser Phe Arg Leu Ser Asn Asp
                20                  25                  30

Leu Ala Thr Ser Ser Ala Glu Ile Ala Arg Gly Glu Thr Ala Asn Ser
            35                  40                  45

Ile Tyr Gln His Gly Asp Gly His
    50                  55

<210> SEQ ID NO 76
<211> LENGTH: 56
<212> TYPE: PRT
<213> ORGANISM: Vitis vinifera

<400> SEQUENCE: 76

Arg Asp Arg Leu Met Glu Cys Phe Phe Trp Thr Ser Phe Ile Thr Thr
1               5                   10                  15

Ile Asp Asp Val Tyr Asp Phe Ser Val Ser Phe Arg Leu Cys Asn Asp
                20                  25                  30

Leu Ala Thr Ser Lys Ala Glu Leu Glu Arg Gly Glu Ser Ala Asn Ser
            35                  40                  45

Ile Tyr Gln Tyr Gly Asp Ser His
    50                  55

<210> SEQ ID NO 77
<211> LENGTH: 56
<212> TYPE: PRT
<213> ORGANISM: Populus alba

<400> SEQUENCE: 77

Arg Asp Arg Leu Ile Glu Ser Phe Tyr Trp Phe Ser Phe Val Thr Ile
1               5                   10                  15

Ile Asp Asp Ile Tyr Asp Phe Ser Ser Ser Phe Arg Leu Cys Asn Asp
            20                  25                  30

Leu Ala Ser Ala Ser Ala Glu Ile Ala Arg Gly Glu Thr Ala Asn Ser
        35                  40                  45

Val Tyr His Asn Gly Asp Ala His
    50                  55

<210> SEQ ID NO 78
<211> LENGTH: 56
<212> TYPE: PRT
<213> ORGANISM: Populus canescens

<400> SEQUENCE: 78

Lys Asp Arg Leu Ile Glu Ser Phe Tyr Trp Phe Ser Phe Val Thr Ile
1               5                   10                  15

Ile Asp Asp Ile Tyr Asp Phe Ser Ser Ser Phe Arg Leu Cys Asn Asp
            20                  25                  30

Leu Ala Ser Ala Ser Ala Glu Ile Ala Arg Gly Glu Thr Ala Asn Ser
        35                  40                  45

Val Tyr His Asn Gly Asp Ala His
    50                  55

<210> SEQ ID NO 79
<211> LENGTH: 56
<212> TYPE: PRT
<213> ORGANISM: Salix sp.

<400> SEQUENCE: 79

Arg Asp Arg Leu Ile Glu Ser Phe Tyr Trp Phe Ser Phe Val Thr Ile
1               5                   10                  15

Ile Asp Asp Ile Tyr Asp Phe Ser Ser Ser Phe Arg Leu Cys Asn Asp
            20                  25                  30

Leu Ala Ser Ala Ser Ala Glu Ile Ala Arg Gly Glu Thr Ala Asn Ser
        35                  40                  45

Val Tyr His Asn Gly Asp Ala His
    50                  55

<210> SEQ ID NO 80
<211> LENGTH: 56
<212> TYPE: PRT
<213> ORGANISM: Malternifolia sp.

<400> SEQUENCE: 80

Arg Asp Arg Leu Met Glu Cys Phe Phe Trp Phe Ser Leu Ile Leu Val
1               5                   10                  15

Leu Asp Asp Val Tyr Asp Phe Ser Ser Ser Phe Arg Leu Thr Asn Asp
            20                  25                  30

Leu Ala Thr Ser Ser Ala Glu Leu Gly Arg Gly Glu Thr Thr Asn Ser
        35                  40                  45

Ile Tyr Gln Asp Gly Asp Ala Ile
    50                  55

<210> SEQ ID NO 81
<211> LENGTH: 56
<212> TYPE: PRT

```
<213> ORGANISM: Eglobulus sp.

<400> SEQUENCE: 81

Arg Asp Arg Leu Ile Glu Cys Phe Phe Trp Phe Ala Leu Ile Leu Val
1               5                   10                  15

Leu Asp Asp Val Tyr Asp Phe Ser Ser Ser Phe Arg Leu Thr Asn Asp
            20                  25                  30

Ile Ala Ser Ser Ser Ala Glu Leu Glu Arg Gly Glu Thr Thr Asn Ser
        35                  40                  45

Ile Tyr Gln Asp Gly Asp Ala Ile
    50                  55

<210> SEQ ID NO 82
<211> LENGTH: 56
<212> TYPE: PRT
<213> ORGANISM: Eucalyptus grandis

<400> SEQUENCE: 82

Arg Asp Arg Leu Thr Glu Cys Phe Phe Trp Thr Ser Leu Ile Thr Ile
1               5                   10                  15

Met Asp Asp Val Tyr Asp Phe Ser Ser Ser Phe Arg Leu Thr Asn Asp
            20                  25                  30

Leu Val Thr Leu Ser Ala Glu Leu Glu Arg Gly Glu Thr Thr Asn Ser
        35                  40                  45

Ile Tyr Gln Asp Gly Asp Ala His
    50                  55

<210> SEQ ID NO 83
<211> LENGTH: 56
<212> TYPE: PRT
<213> ORGANISM: Wisteria sp.

<400> SEQUENCE: 83

Arg Asp Arg Leu Met Glu Val Tyr Phe Trp Phe Gly Leu Val Thr Ile
1               5                   10                  15

Ile Asp Asp Val Tyr Asp Phe Ser Ser Ser Phe Arg Leu Cys Asn Asp
            20                  25                  30

Leu Ala Thr Ser Ala Ala Glu Leu Glu Arg Gly Glu Thr Thr Asn Ser
        35                  40                  45

Ile Tyr Gln His Gly Asp Gly Leu
    50                  55

<210> SEQ ID NO 84
<211> LENGTH: 56
<212> TYPE: PRT
<213> ORGANISM: Robinia pseudoacacia

<400> SEQUENCE: 84

Arg Asp Arg Leu Val Glu Val Tyr Phe Trp Phe Gly Leu Val Thr Ile
1               5                   10                  15

Ile Asp Asp Val Tyr Asp Phe Ser Ser Ser Phe Arg Leu Cys Asn Asp
            20                  25                  30

Leu Ala Thr Ser Ala Ala Glu Leu Glu Arg Gly Glu Thr Thr Asn Ser
        35                  40                  45

Ile Tyr Gln Tyr Gly Asp Gly Leu
    50                  55

<210> SEQ ID NO 85
<211> LENGTH: 56
```

```
<212> TYPE: PRT
<213> ORGANISM: Arachis hypogaea

<400> SEQUENCE: 85

Arg Asp Arg Leu Met Glu Val Tyr Phe Trp Phe Gly Leu Val Thr Ile
1               5                   10                  15

Ile Asp Asp Val Tyr Asp Phe Ser Ser Ser Phe Arg Leu Cys Asn Asp
            20                  25                  30

Leu Ala Thr Ser Ala Ala Glu Leu Glu Arg Gly Glu Thr Thr Asn Ser
        35                  40                  45

Ile Tyr Gln Tyr Gly Asp Gly Leu
    50                  55

<210> SEQ ID NO 86
<211> LENGTH: 56
<212> TYPE: PRT
<213> ORGANISM: Glycine max

<400> SEQUENCE: 86

Arg Asp Arg Leu Met Glu Val Tyr Phe Trp Phe Gly Leu Val Thr Ile
1               5                   10                  15

Ile Asp Asp Val Tyr Asp Phe Ser Ser Ser Phe Arg Leu Cys Asn Asp
            20                  25                  30

Leu Thr Thr Ser Ala Ala Glu Leu Glu Arg Gly Glu Thr Thr Asn Ser
        35                  40                  45

Ile Tyr Gln Tyr Gly Asp Gly Leu
    50                  55

<210> SEQ ID NO 87
<211> LENGTH: 56
<212> TYPE: PRT
<213> ORGANISM: Pueraria montana var. lobata

<400> SEQUENCE: 87

Arg Asp Arg Leu Met Glu Val Tyr Phe Trp Phe Gly Leu Val Thr Ile
1               5                   10                  15

Ile Asp Asp Val Tyr Asp Phe Ser Ser Ser Phe Arg Leu Cys Asn Asp
            20                  25                  30

Leu Ala Thr Ser Ala Ala Glu Leu Glu Arg Gly Glu Thr Thr Asn Ser
        35                  40                  45

Ile Tyr Gln Tyr Gly Asp Gly Leu
    50                  55

<210> SEQ ID NO 88
<211> LENGTH: 56
<212> TYPE: PRT
<213> ORGANISM: Mucuna pruriens

<400> SEQUENCE: 88

Arg Asp Arg Leu Met Glu Val Tyr Phe Trp Phe Gly Leu Val Thr Ile
1               5                   10                  15

Ile Asp Asp Val Tyr Asp Phe Ser Ser Ser Phe Arg Leu Cys Asn Asp
            20                  25                  30

Leu Ala Thr Ser Ala Ala Glu Leu Glu Arg Gly Glu Thr Thr Asn Ser
        35                  40                  45

Ile Tyr Gln Tyr Gly Asp Gly Leu
    50                  55

<210> SEQ ID NO 89
```

<211> LENGTH: 56
<212> TYPE: PRT
<213> ORGANISM: Glycine max

<400> SEQUENCE: 89

Arg Asp Arg Leu Met Glu Val Tyr Phe Trp Phe Ala Leu Ile Gly Ile
1               5                   10                  15

Ile Asp Asp Val Tyr Asp Phe Ser Ser Ser Phe Arg Leu Cys Asn Asp
                20                  25                  30

Leu Ala Thr Ser Ala Ala Glu Leu Glu Thr Gly Glu Thr Ala Asn Ser
            35                  40                  45

Ile Tyr Gln Tyr Glu Asp Gly Leu
    50                  55

<210> SEQ ID NO 90
<211> LENGTH: 56
<212> TYPE: PRT
<213> ORGANISM: Cajanus cajan

<400> SEQUENCE: 90

Arg Asp Arg Leu Met Glu Val Tyr Phe Trp Phe Gly Leu Val Thr Ile
1               5                   10                  15

Ile Asp Asp Val Tyr Asp Phe Ser Ser Ser Phe Arg Leu Tyr Asn Asp
                20                  25                  30

Leu Ala Thr Ser Ala Ala Glu Leu Glu Arg Asp Glu Thr Thr Asn Ser
            35                  40                  45

Met Tyr Gln His Gly Asp Gly Leu
    50                  55

<210> SEQ ID NO 91
<211> LENGTH: 56
<212> TYPE: PRT
<213> ORGANISM: Mangifera indica

<400> SEQUENCE: 91

Arg Asp Arg Leu Met Glu Cys Tyr Phe Trp Phe Ala Phe Val Thr Thr
1               5                   10                  15

Ile Asp Asp Ile Tyr Asp Phe Ser Ser Ser Phe Arg Leu Cys Asn Asp
                20                  25                  30

Leu Ser Thr Ser Lys Asp Glu Leu Glu Arg Gly Glu Thr Ala Ser Ser
            35                  40                  45

Ile Tyr Gln His Gly Asp Gly His
    50                  55

<210> SEQ ID NO 92
<211> LENGTH: 56
<212> TYPE: PRT
<213> ORGANISM: Ipomoea batatas

<400> SEQUENCE: 92

Arg Asp Arg Leu Met Glu Ser Phe Phe Trp Lys Leu Val Thr Val
1               5                   10                  15

Leu Asp Asp Val Tyr Asp Phe Ser Val Ser Phe Arg Leu Ala Asn Asp
                20                  25                  30

Leu Ser Ser Ser Lys Ala Glu Ile Glu Arg Gly Glu Thr Ala Asn Ser
            35                  40                  45

Ile Tyr Gln Tyr Gly Asp Ala His
    50                  55

```
<210> SEQ ID NO 93
<211> LENGTH: 56
<212> TYPE: PRT
<213> ORGANISM: Sesamum indicum

<400> SEQUENCE: 93

Arg Asp Arg Leu Met Glu Ser Phe Phe Trp Val Asn Leu Ile Thr Val
1               5                   10                  15

Leu Asp Asp Ile Tyr Asp Phe Ser Ser Ser Phe Arg Leu Ala Asn Asp
            20                  25                  30

Leu Ser Ser Ser Lys Asp Asp Val Gly Arg Gly Glu Thr Ala Lys Ala
        35                  40                  45

Val Tyr Gln His Gly Asp Ala His
    50                  55

<210> SEQ ID NO 94
<211> LENGTH: 56
<212> TYPE: PRT
<213> ORGANISM: Humulus lupulus

<400> SEQUENCE: 94

Arg Asp Arg Leu Met Glu Ala Phe Leu Trp Phe Val Leu Ile Thr Ile
1               5                   10                  15

Ile Asp Asp Ile Tyr Asp Tyr Ser Ile Gly Val Arg Leu Ala Asp Asp
            20                  25                  30

Phe Gly Thr Phe Ser Asp Glu Leu Asn Arg Gly Asp Val Pro Lys Ser
        35                  40                  45

Ile Tyr Gln Tyr Gly Asp Gly His
    50                  55

<210> SEQ ID NO 95
<211> LENGTH: 56
<212> TYPE: PRT
<213> ORGANISM: Matricaria recutita

<400> SEQUENCE: 95

Arg Asp Arg Leu Met Glu Cys Phe Phe Trp Ala Thr Leu Ile Thr Thr
1               5                   10                  15

Ile Asp Asp Ile Tyr Asp Phe Ser Val Ser Phe Arg Leu Tyr Asn Asp
            20                  25                  30

Leu Ala Ala Leu Ala Asp Glu Ile Asp Lys Asp Lys Ser Pro Asn Ala
        35                  40                  45

Ile Tyr Gln Tyr Gly Asp Gly Ile
    50                  55

<210> SEQ ID NO 96
<211> LENGTH: 56
<212> TYPE: PRT
<213> ORGANISM: Dahlia pinnata

<400> SEQUENCE: 96

Arg Asp Arg Leu Leu Glu Cys Phe Phe Trp Ser Thr Phe Ile Thr Ile
1               5                   10                  15

Leu Asp Asp Ile Tyr Asp Phe Ser Val Ser Phe Arg Leu Tyr Asn Asp
            20                  25                  30

Leu Ala Thr Ser Ser Ser Glu Ile Gln Arg Gly Lys Asn Val Asn Ala
        35                  40                  45

Val Tyr Gln Tyr Gly Asp Gly His
    50                  55
```